(12) United States Patent
Diaz et al.

(10) Patent No.: US 11,964,141 B2
(45) Date of Patent: *Apr. 23, 2024

(54) SYSTEM AND METHOD FOR SAFETY SYRINGE

(71) Applicant: Credence Medsystems, Inc., Menlo Park, CA (US)

(72) Inventors: Stephen H. Diaz, Palo Alto, CA (US); Alan E. Shluzas, San Carlos, CA (US)

(73) Assignee: Credence MedSystems, Inc., Menlo Park, CA (US)

( * ) Notice: Subject to any disclaimer, the term of this patent is extended or adjusted under 35 U.S.C. 154(b) by 206 days.

This patent is subject to a terminal disclaimer.

(21) Appl. No.: 17/403,095

(22) Filed: Aug. 16, 2021

(65) Prior Publication Data
US 2022/0031964 A1 Feb. 3, 2022

Related U.S. Application Data

(63) Continuation of application No. 16/011,453, filed on Jun. 18, 2018, now Pat. No. 11,090,445.
(Continued)

(51) Int. Cl.
*A61M 5/36* (2006.01)
*A61F 9/00* (2006.01)
(Continued)

(52) U.S. Cl.
CPC .............. *A61M 5/36* (2013.01); *A61F 9/0017* (2013.01); *A61M 5/3135* (2013.01);
(Continued)

(58) Field of Classification Search
CPC .... A61M 5/36; A61M 5/3135; A61M 5/3137; A61M 5/3146; A61M 5/31505;
(Continued)

(56) References Cited

U.S. PATENT DOCUMENTS 827,693 A 7/1906 Korb
2,648,334 A 8/1953 Brown et al.
(Continued)

FOREIGN PATENT DOCUMENTS

EP 0074842 3/1983
EP 0904792 3/1999
(Continued)

OTHER PUBLICATIONS

PCT International Search Report for PCT/US2021/037946, Applicant Credence Medsystems Inc., dated Oct. 6, 2021.
(Continued)

*Primary Examiner* — Robert J Utama
*Assistant Examiner* — Justin L Zamory
(74) *Attorney, Agent, or Firm* — Vista IP Law Group LLP

(57) ABSTRACT

A system for injecting includes a syringe body having proximal and distal ends, a syringe interior, and a syringe flange at the proximal end thereof. The system also includes a stopper member disposed in the syringe interior. The system further includes a plunger member coupled to the stopper member. The plunger member includes a rotatable member configured to insert the stopper member distally in the syringe interior relative to the syringe body with rotation of the rotatable member. The plunger member further includes a proximal portion proximal of the rotatable member configured to be moved distally to also insert the stopper member distally in the syringe interior relative to the syringe body to eject about microliters of fluid from the syringe interior.

20 Claims, 52 Drawing Sheets

Related U.S. Application Data

(60) Provisional application No. 62/639,614, filed on Mar. 7, 2018, provisional application No. 62/521,252, filed on Jun. 16, 2017.

(51) Int. Cl.
*A61M 5/31* (2006.01)
*A61M 5/315* (2006.01)
*A61M 5/34* (2006.01)

(52) U.S. Cl.
CPC ........ *A61M 5/3137* (2013.01); *A61M 5/3146* (2013.01); *A61M 5/31505* (2013.01); *A61M 5/31511* (2013.01); *A61M 5/31515* (2013.01); *A61M 5/31531* (2013.01); *A61M 5/3157* (2013.01); *A61M 5/347* (2013.01); *A61M 2005/3143* (2013.01); *A61M 2205/0216* (2013.01); *A61M 2205/581* (2013.01); *A61M 2205/582* (2013.01); *A61M 2205/583* (2013.01); *A61M 2205/584* (2013.01)

(58) Field of Classification Search
CPC .......... A61M 5/31511; A61M 5/31515; A61M 5/31531; A61M 5/3157; A61M 5/347; A61M 2005/31508; A61M 2005/3143; A61M 2005/3139; A61M 2205/581; A61M 2205/582; A61M 2205/583; A61M 2205/584
See application file for complete search history.

(56) References Cited

U.S. PATENT DOCUMENTS

| | | | |
|---|---|---|---|
| 2,771,217 | A | 11/1956 | Brown et al. |
| 2,933,087 | A | 4/1960 | Hamilton |
| 3,153,496 | A | 10/1964 | Johnson |
| 3,216,616 | A | 11/1965 | Blankenship, Jr. |
| 3,770,026 | A | 11/1973 | Isenberg |
| 3,815,785 | A | 6/1974 | Gilmont |
| 3,921,864 | A | 11/1975 | Dawes |
| 3,923,207 | A | 12/1975 | Kyogoku |
| 4,073,321 | A | 2/1978 | Moskowitz |
| 4,194,505 | A | 3/1980 | Schmitz |
| 4,370,982 | A | 2/1983 | Reilly |
| 4,384,581 | A | 5/1983 | Conway |
| 4,563,178 | A | 1/1986 | Santeramo |
| 4,973,318 | A | 11/1990 | Holm et al. |
| 5,271,527 | A | 12/1993 | Haber et al. |
| 5,304,152 | A | 4/1994 | Sams |
| 5,433,352 | A | 7/1995 | Ronvig |
| 5,667,495 | A | 9/1997 | Bitdinger et al. |
| 5,743,889 | A | 4/1998 | Sams |
| 5,833,669 | A | 11/1998 | Wyrick |
| 5,961,495 | A | 10/1999 | Walters et al. |
| 6,126,644 | A | 10/2000 | Naganuma |
| 7,329,241 | B2 | 2/2008 | Horvath et al. |
| 7,678,084 | B2 | 3/2010 | Judson et al. |
| 8,361,036 | B2 | 1/2013 | Moller et al. |
| 8,529,521 | B2 | 9/2013 | Erickson et al. |
| 9,220,631 | B2 | 12/2015 | Sigg et al. |
| 9,345,842 | B2 | 5/2016 | Chanoch et al. |
| 9,566,387 | B2 | 2/2017 | Verhoeven et al. |
| 11,090,445 | B2 * | 8/2021 | Diaz ..................... A61M 5/347 |
| 2003/0032928 | A1 * | 2/2003 | Sudo ..................... A61M 5/315 604/220 |
| 2006/0129108 | A1 | 6/2006 | Vetter et al. |
| 2006/0200077 | A1 | 9/2006 | Righi et al. |
| 2006/0206057 | A1 | 9/2006 | Deruntz et al. |
| 2007/0265579 | A1 | 11/2007 | Kleyman et al. |
| 2008/0221530 | A1 | 9/2008 | Glejbol et al. |
| 2008/0262435 | A1 | 10/2008 | Erickson et al. |
| 2010/0175779 | A1 | 7/2010 | Ogawa et al. |
| 2011/0046559 | A1 | 2/2011 | Lum et al. |
| 2013/0226091 | A1 | 8/2013 | Nzike et al. |
| 2016/0220761 | A1 | 8/2016 | Shetty et al. |
| 2016/0228643 | A1 | 8/2016 | Oberdorfer et al. |
| 2016/0263329 | A1 | 9/2016 | Young et al. |
| 2016/0293329 | A1 | 9/2016 | Young et al. |
| 2017/0216524 | A1 | 8/2017 | Haider et al. |
| 2018/0126085 | A1 | 5/2018 | Bowman et al. |
| 2018/0250474 | A1 | 9/2018 | Wei |
| 2019/0015597 | A1 | 1/2019 | Holmqvist et al. |
| 2020/0306453 | A1 | 10/2020 | Langley et al. |
| 2020/0324054 | A1 | 10/2020 | Helmer et al. |

FOREIGN PATENT DOCUMENTS

| | | |
|---|---|---|
| EP | 1260241 | 11/2002 |
| EP | 2328639 B1 | 6/2011 |
| EP | 2397173 A2 | 12/2011 |
| JP | H08-294533 | 11/1996 |
| JP | 2006-506166 | 2/2006 |
| JP | 2012-231932 | 11/2012 |
| JP | 2015-500095 | 1/2015 |
| JP | 2016-537108 | 12/2016 |
| WO | WO 96/26754 | 9/1996 |
| WO | WO 2012/149040 A2 | 11/2012 |
| WO | WO 2015/073991 A1 | 5/2015 |
| WO | WO 2017/062304 A1 | 4/2017 |
| WO | WO 2017/168287 | 10/2017 |
| WO | WO 2017/1804787 | 10/2017 |
| WO | WO 2017/204787 | 11/2017 |
| WO | WO 2018146589 | 8/2018 |

OTHER PUBLICATIONS

Foreign OA for JP Patent Appln. No. 2019-569308 dated Jul. 20, 2021.
Notice of Allowance for U.S. Appl. No. 16/011,453 dated Apr. 14, 2021.
Non-Final Office Action for U.S. Appl. No. 16/683,126 dated Jul. 27, 2021.
Amendment Response to NFOA for U.S. Appl. No. 16/683,126 dated Oct. 27, 2021.
Non-Final Office Action for U.S. Appl. No. 16/011,453 dated Oct. 1, 2020.
Amendment Response to NFOA for U.S. Appl. No. 16/011,453 dated Jan. 4, 2021.
PCT International Search Report for PCT/US2018/038098, Applicant: Credence Medsystems, Inc., Form PCT/ISA/210 and 220, dated Nov. 6, 2018 (9pages).
PCT Written Opinion of the International Search Authority for PCT/US2018/038098, Applicant: Credence Medsystems, Inc., Form PCT/ISA/237, dated Nov. 6, 2018 (10pages).
PCT International Search Report and Written Opinion for International Appln. No. PCT/US2019/061310 dated Jun. 22, 2020.
Foreign Response for JP Patent Appln. No. 2019-569308 dated Oct. 18, 2021.
Foreign OA for JP Patent Appln. No. 2019-569308 dated Jan. 18, 2022.
Notice of Allowance for U.S. Appl. No. 16/683,126 dated Apr. 13, 2022.
Foreign Response for JP Patent Appln. No. 2019-569308 dated Apr. 12, 2022.
Foreign NOA for JP Patent Appln. No. 2019-569308 dated Apr. 18, 2022 (with English translation).
Foreign OA for JP Patent Appln. No. 2022-100018 dated Aug. 8, 2023 (with English translation).
Foreign OA for JP Patent Appln. No. 2021-525106 dated Feb. 7, 2023 (with English translation).
Foreign Response for JP Patent Appln. No. 2021-525106 dated Jul. 7, 2023.
Ex Parte Quaye Action for U.S. Appl. No. 17/351,006 dated Jun. 16, 2023.
Amendment Response to Ex Parte Quayle for U.S. Appl. No. 17/351,006 dated Aug. 15, 2023.

(56) References Cited

OTHER PUBLICATIONS

Notice of Allowance for U.S. Appl. No. 17/351,006 dated Aug. 23, 2023.
Notice of Allowance for U.S. Appl. No. 17/351,006 dated Sep. 13, 2023.
Foreign Response to JP Patent Appln. No. 2022-100018 dated Oct. 3, 2023.
Examination Report for Appln No. 18738167.8 dated Nov. 15, 2022.
Response to Examination Report for Appln No. 18738167.8 dated Mar. 27, 2023.
Foreign OA for JP Patent Appln. No. 2021-525106 dated Sep. 26, 2023 (with English translation).
Foreign OA to JP Patent Appln. No. 2022-100018 dated Jan. 12, 2024 (with English translation).
Foreign OA Response for JP Patent Appln. No. 2021-525106 dated Dec. 26, 2023 (with English Amended Claims).
Foreign Voluntary Amendment for CA Patent Appln. No. 3119277 dated Dec. 21, 2023.
Foreign NOA for CA Patent Appln. No. 3119277 dated Jan. 25, 2024.

* cited by examiner

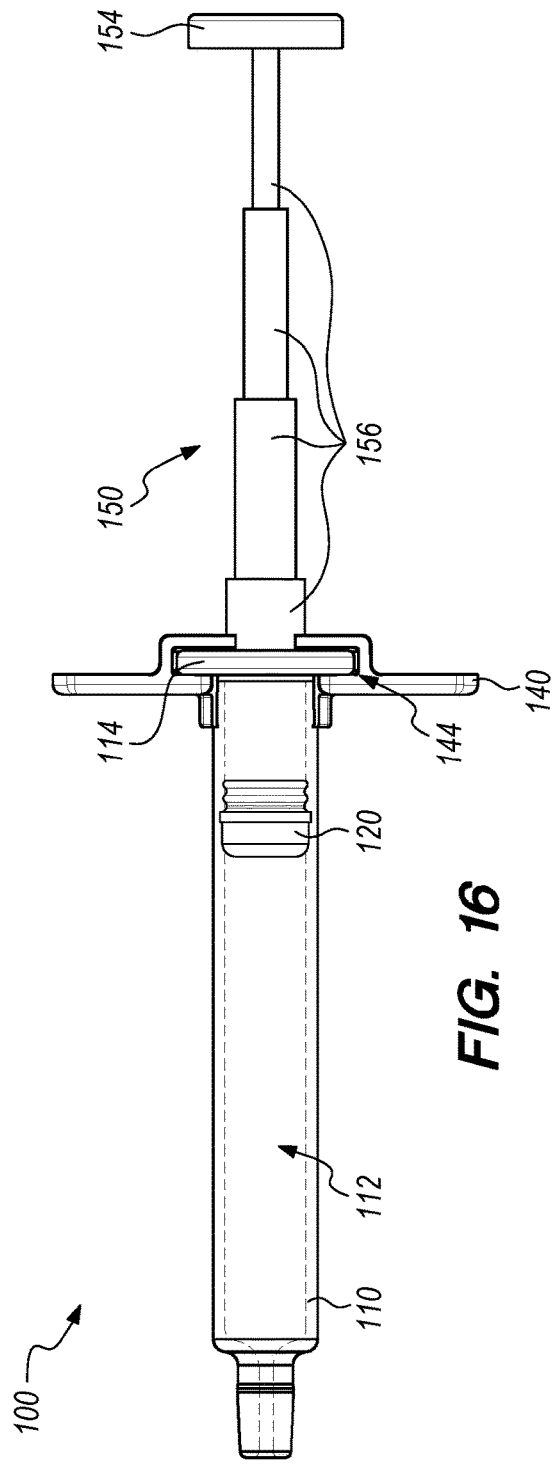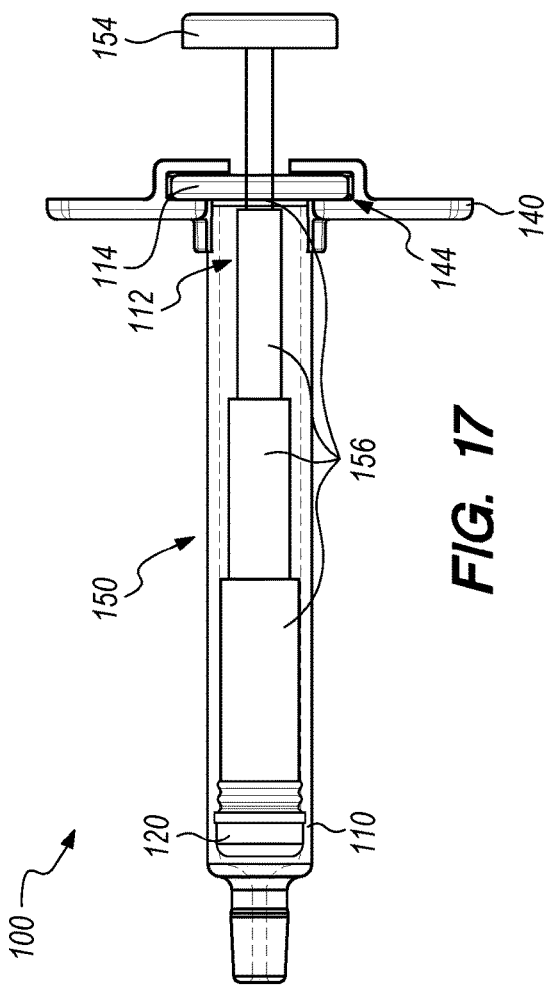

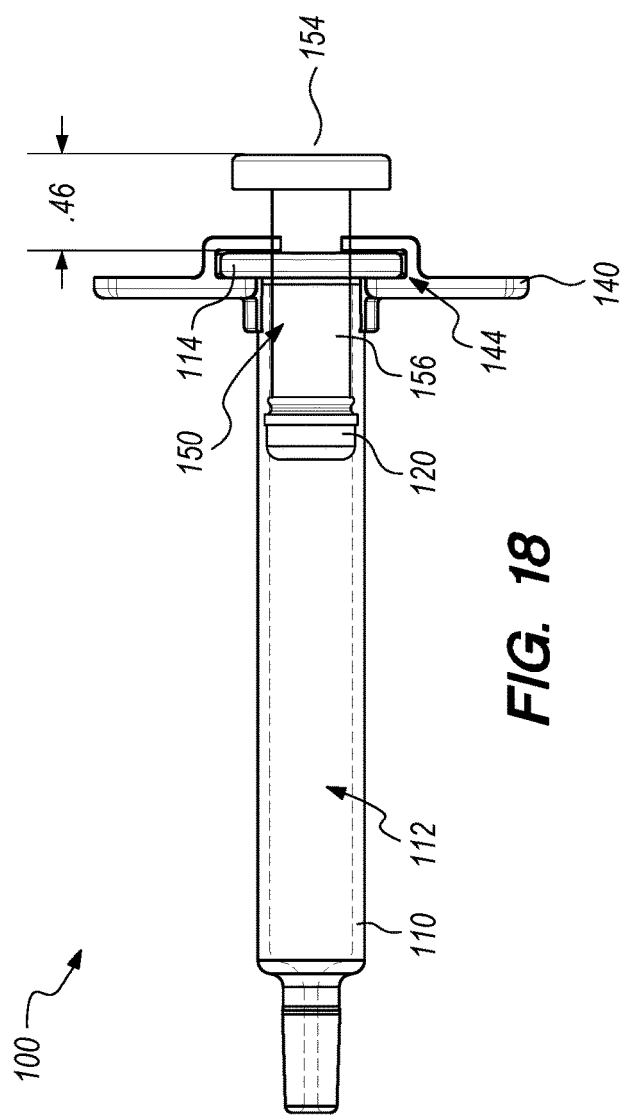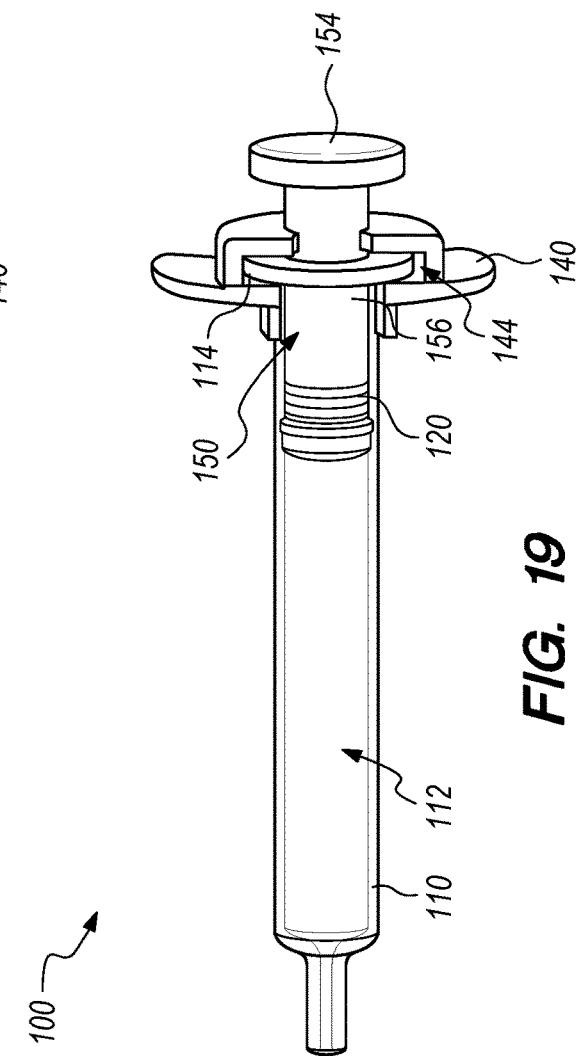

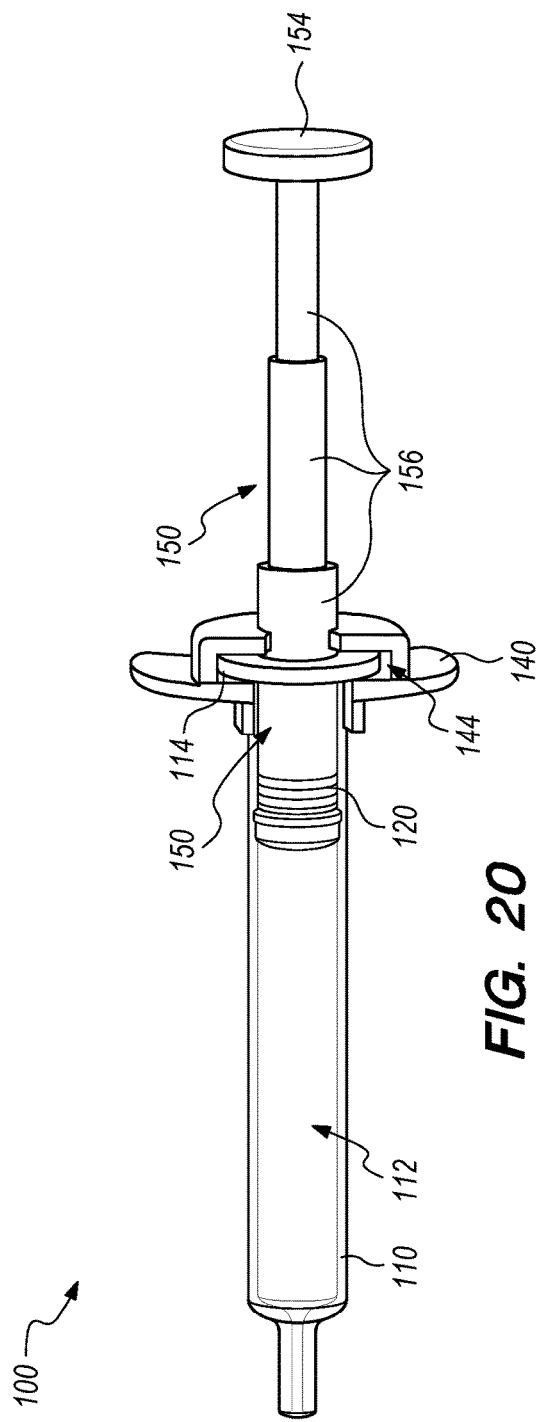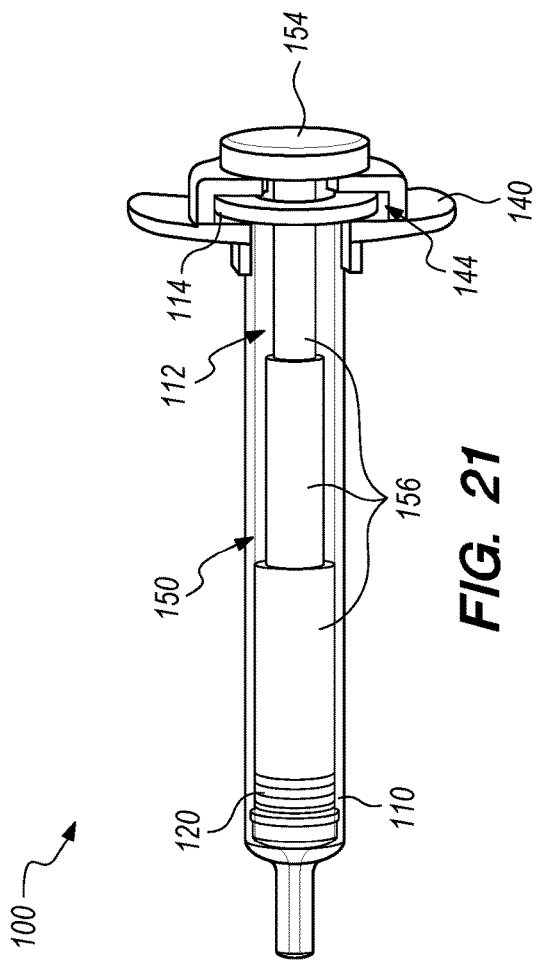

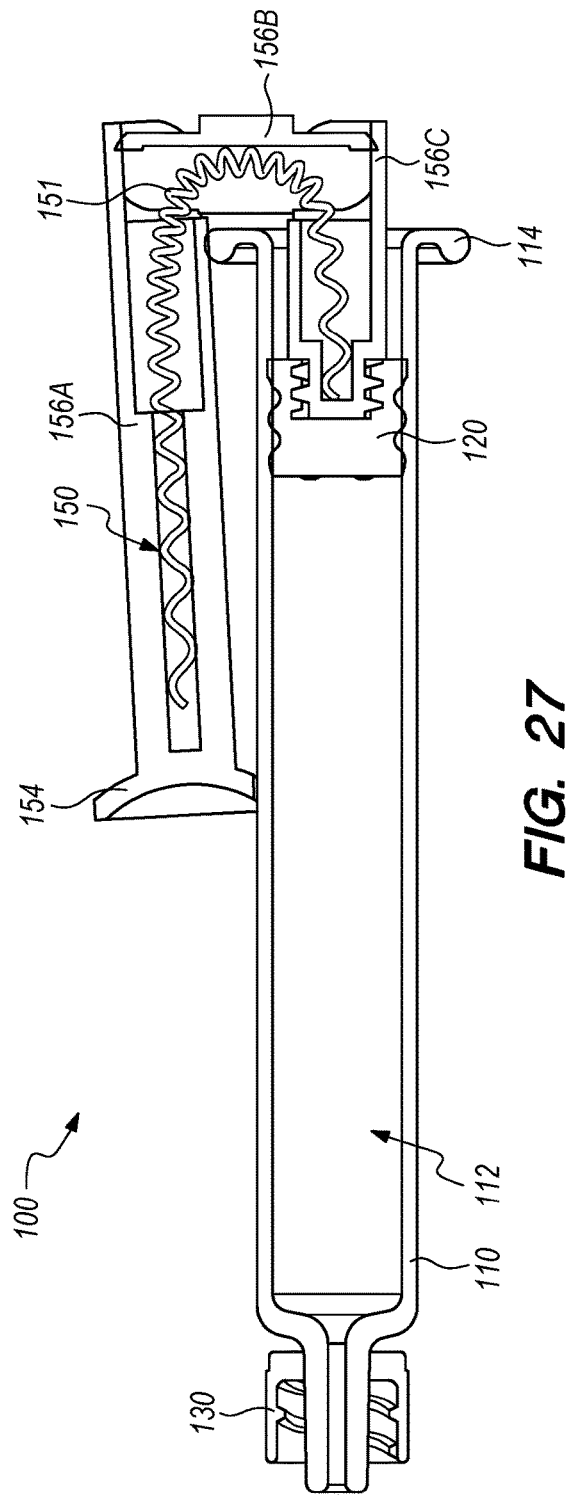
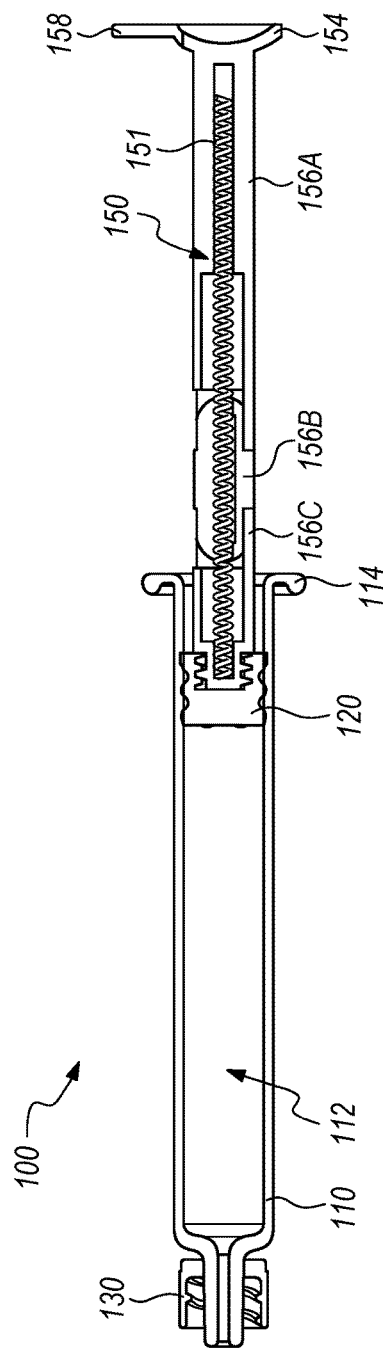
FIG. 27
FIG. 28

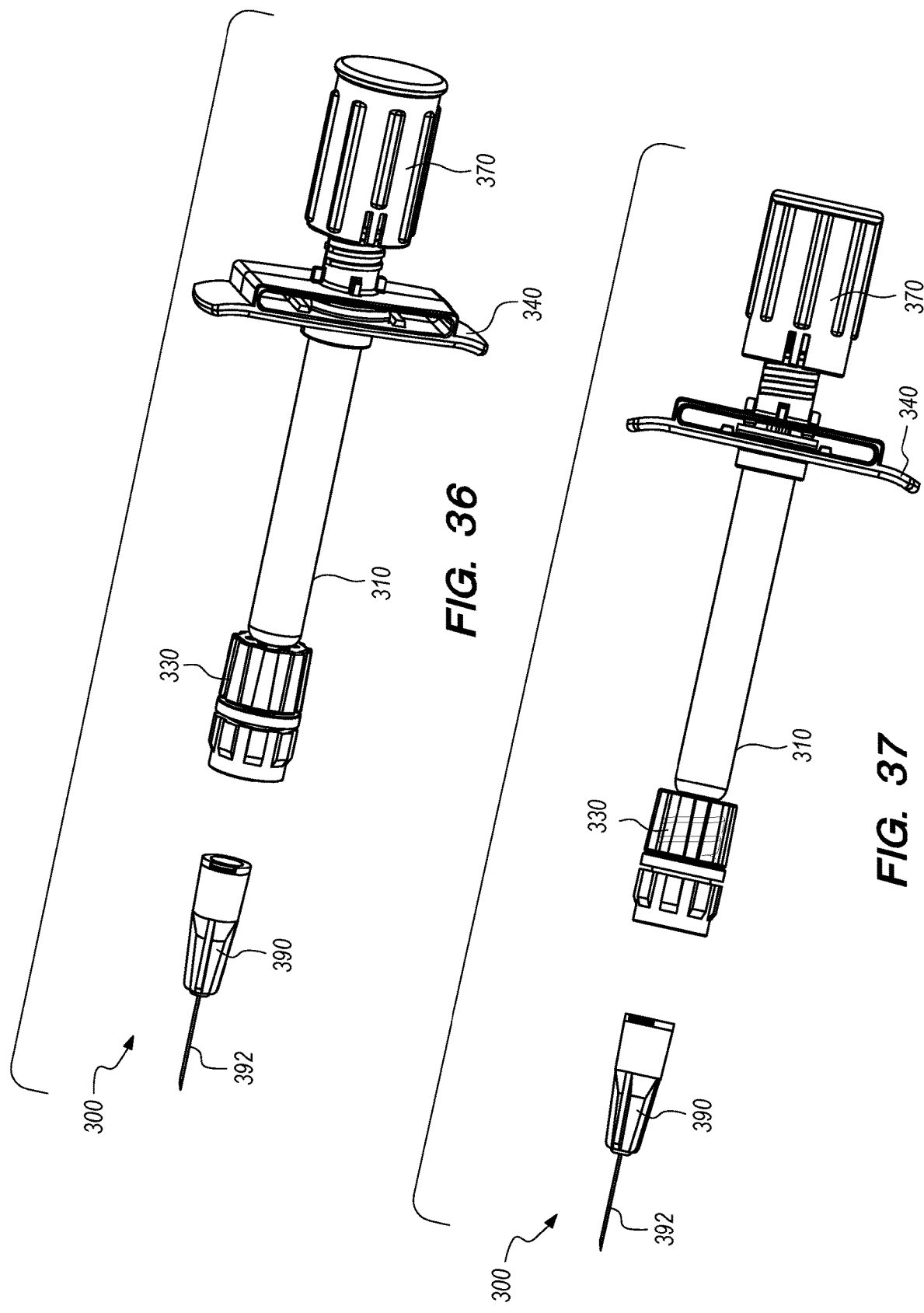

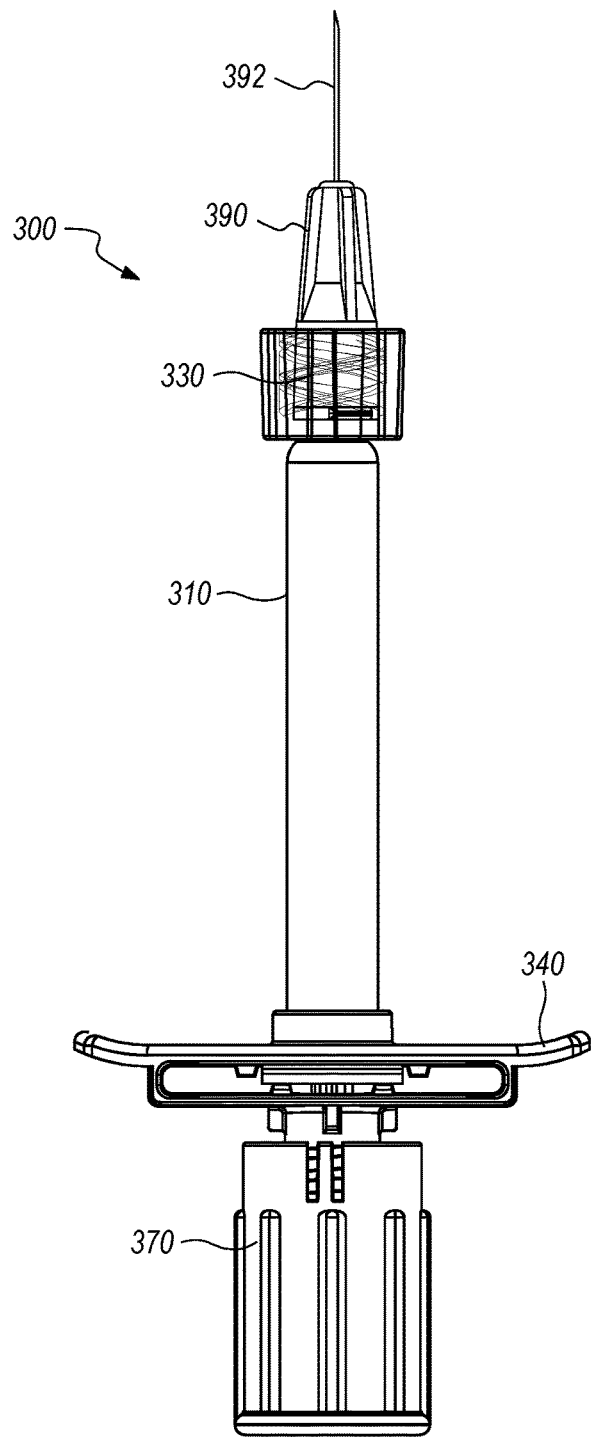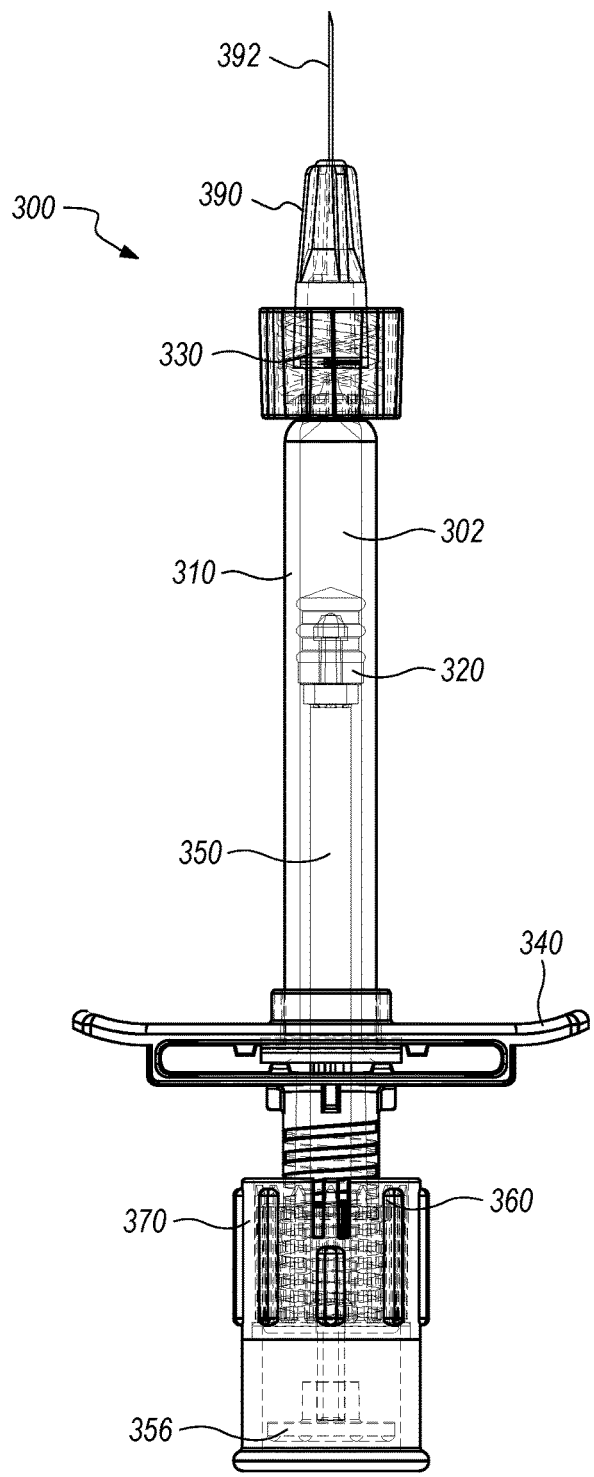
FIG. 42
FIG. 43

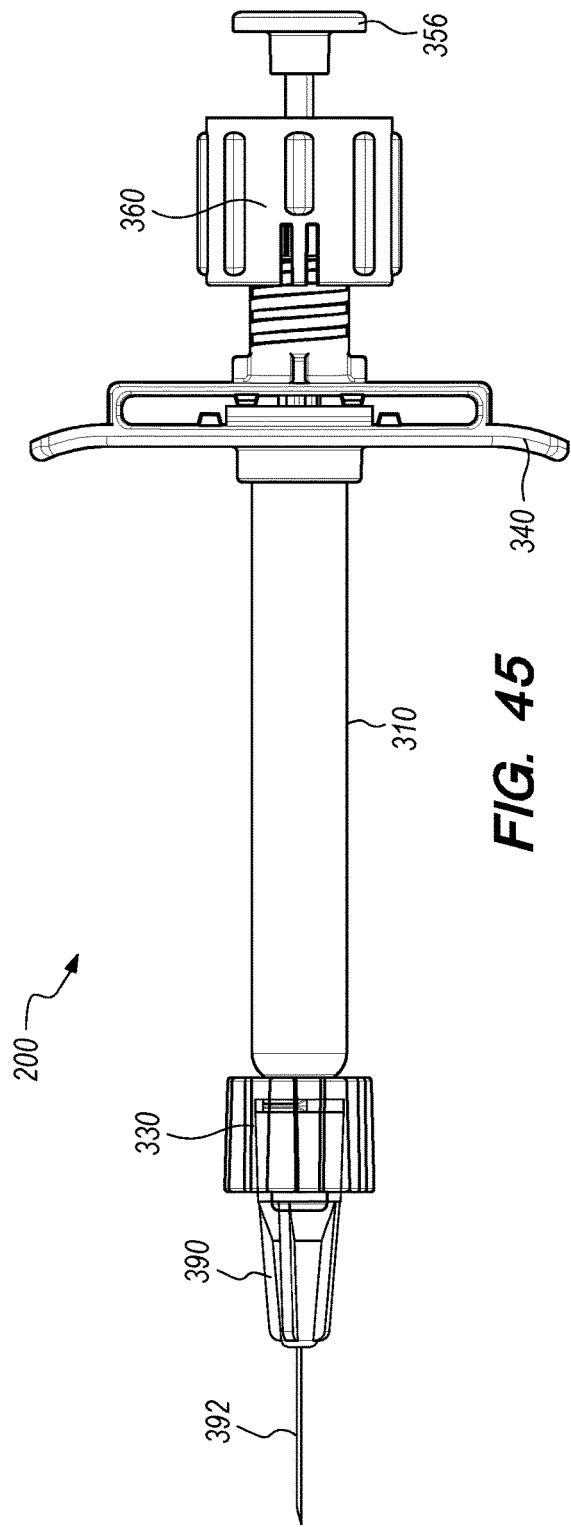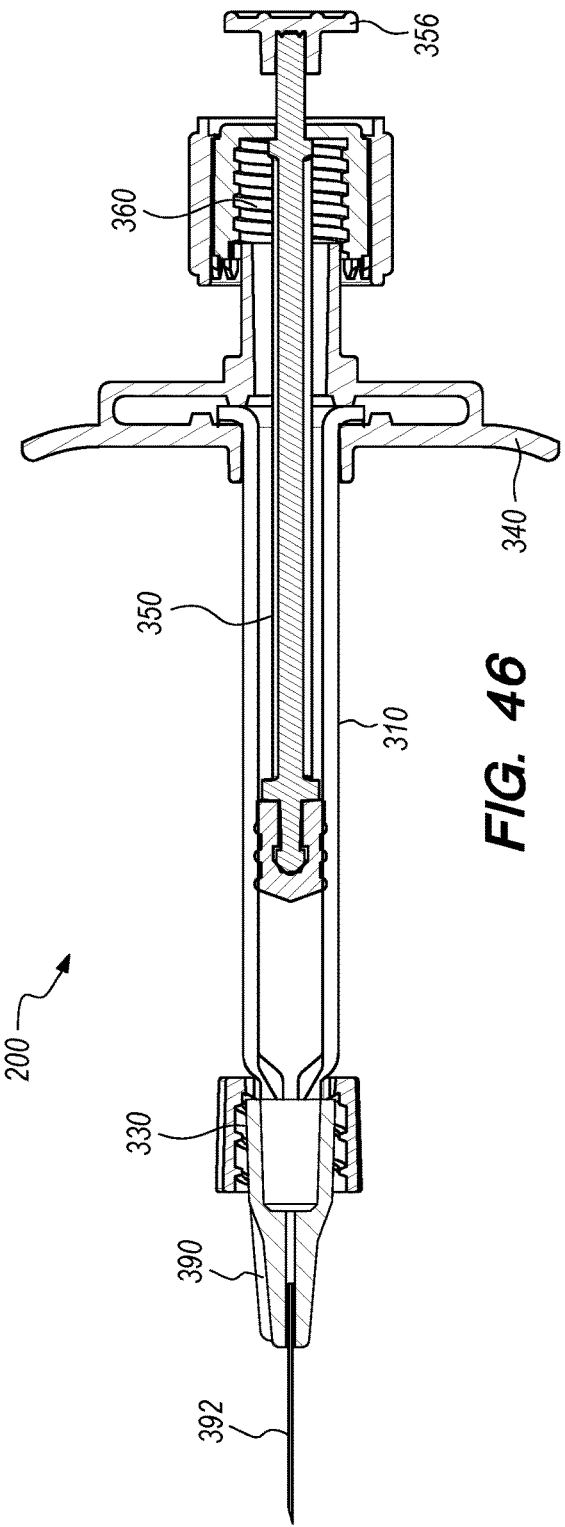

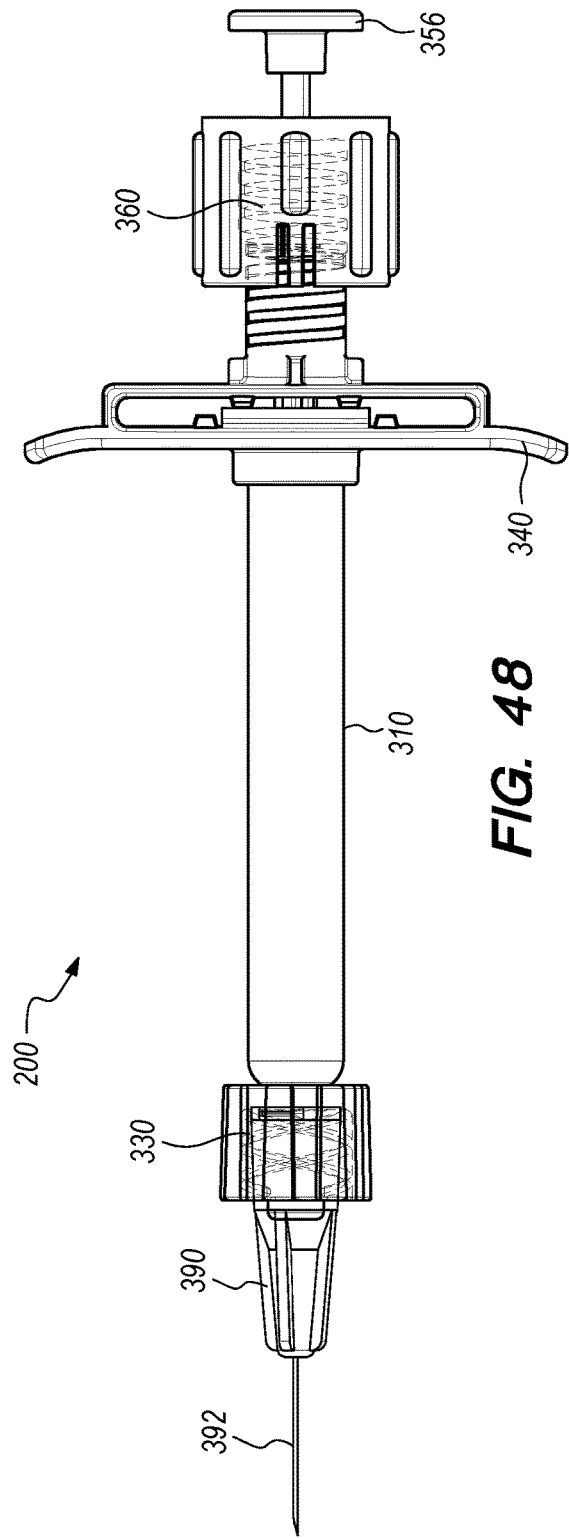
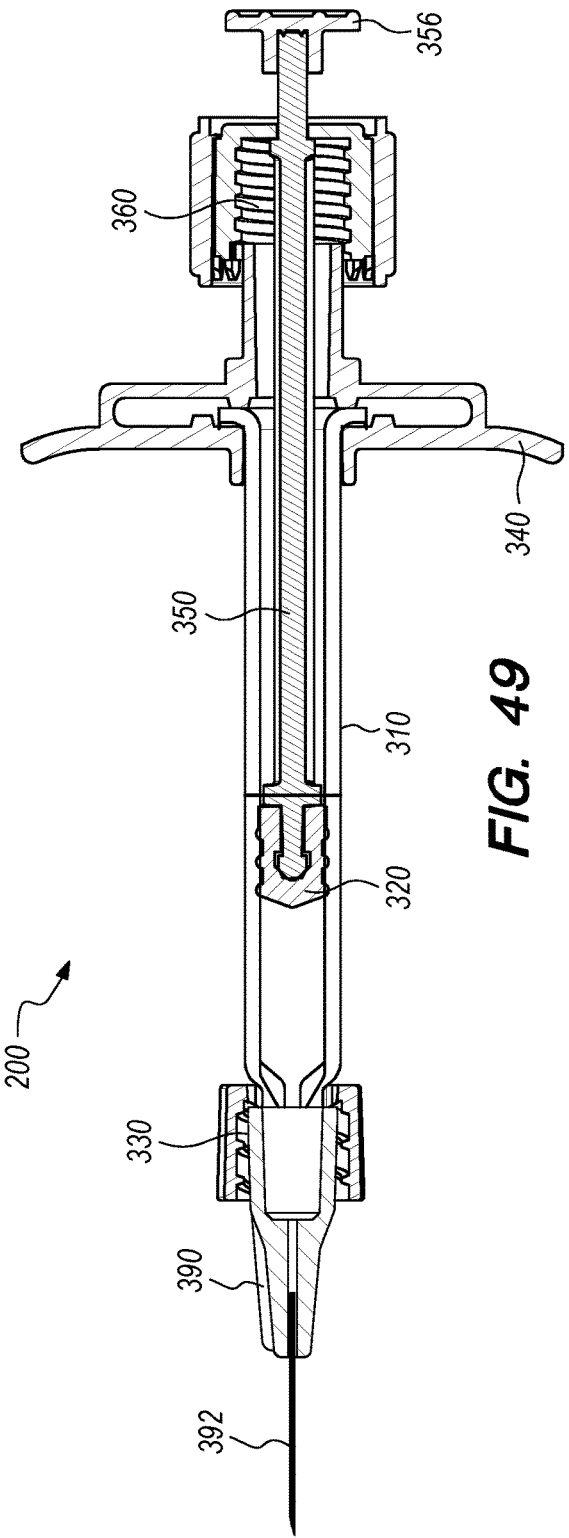

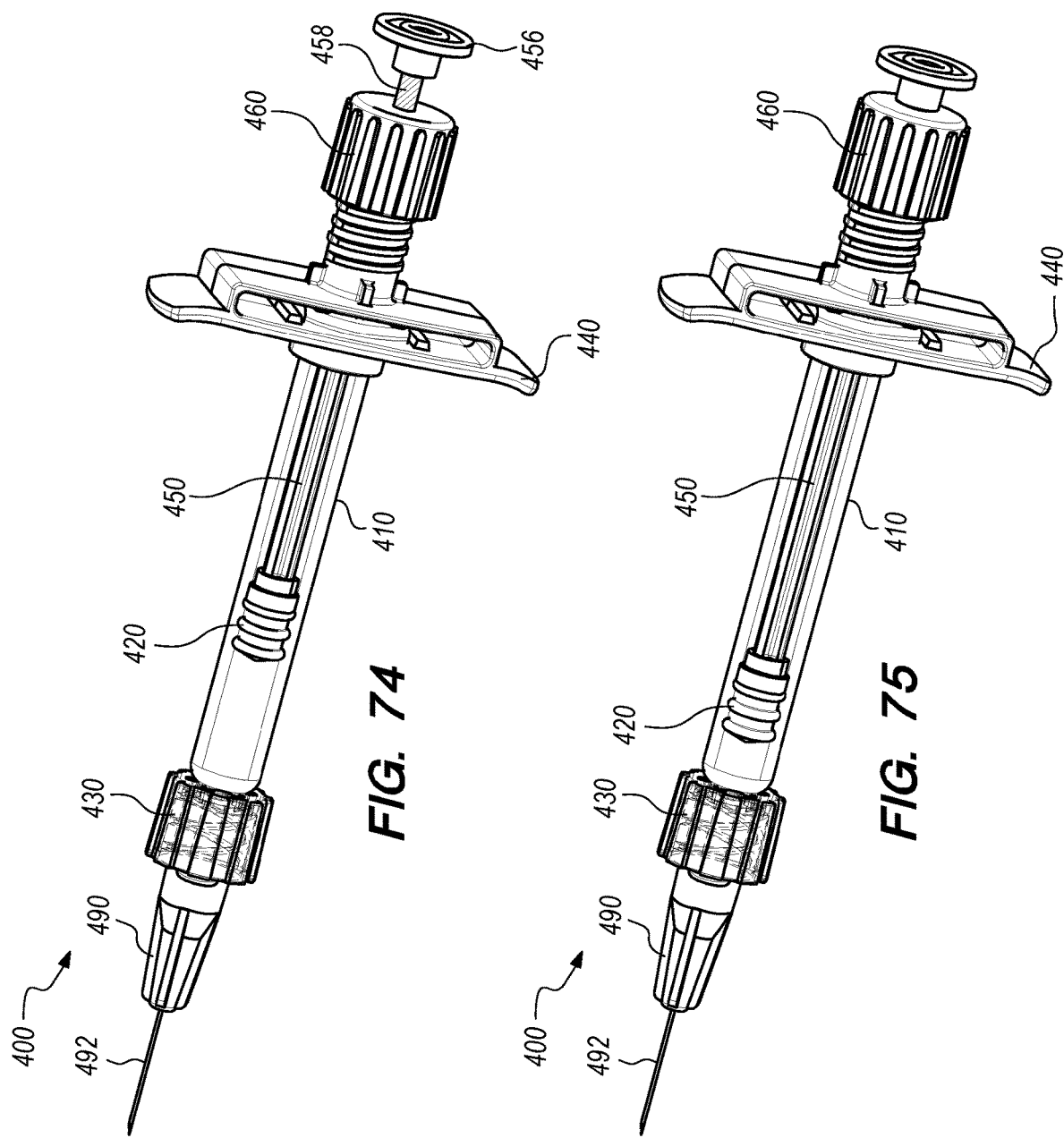

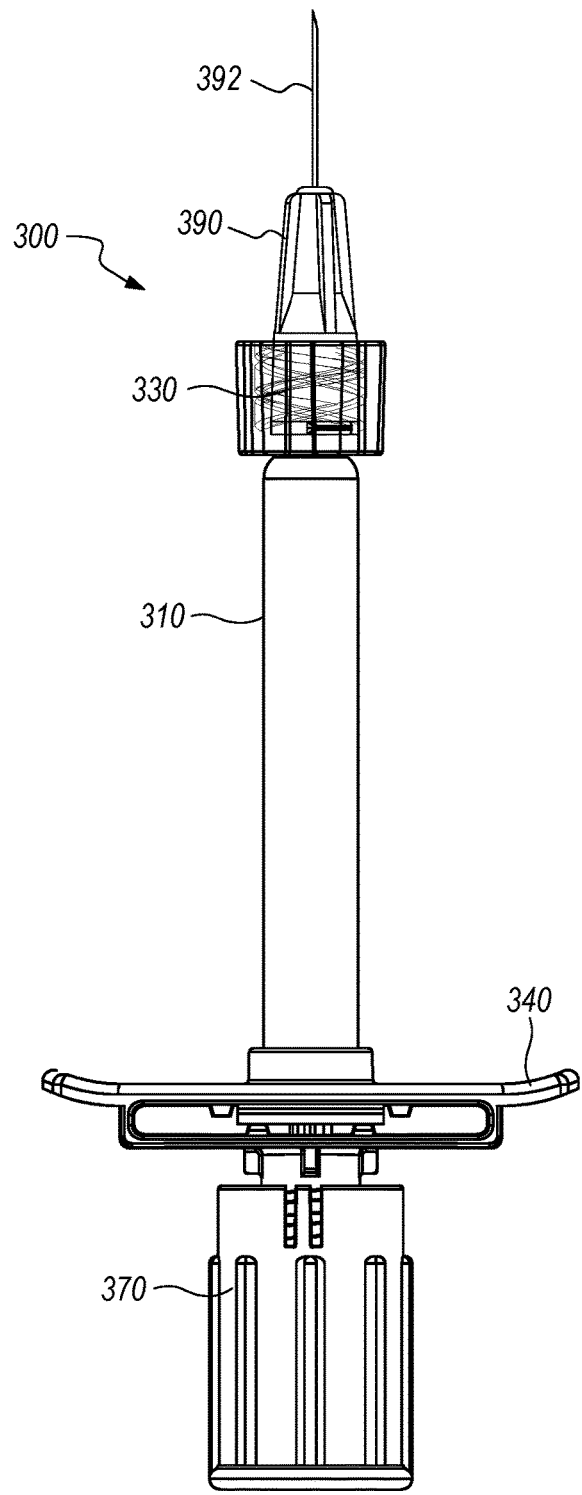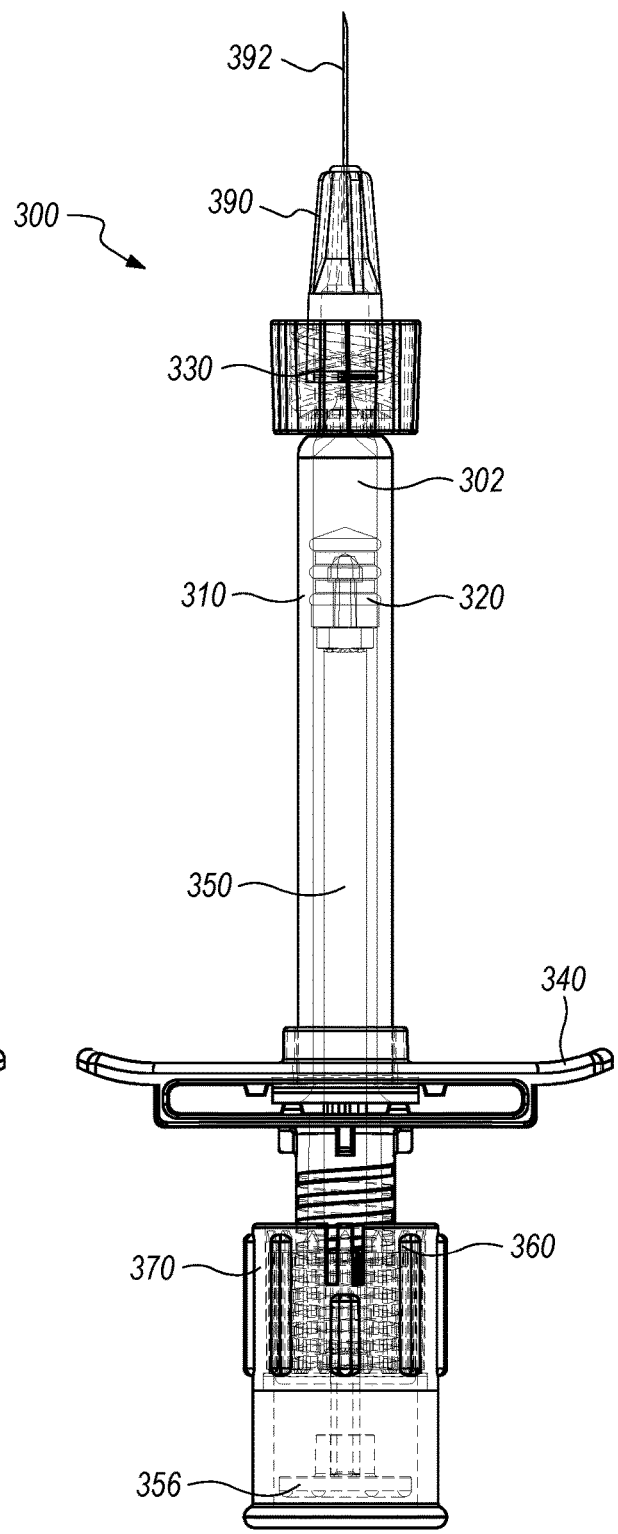
FIG. 76
FIG. 77

SYSTEM AND METHOD FOR SAFETY SYRINGE

The present application is a continuation of U.S. patent application Ser. No. 16/011,453 filed on Jun. 16, 2018 entitled "SYSTEM AND METHOD FOR SAFETY SYRINGE" which claims priority to U.S. Provisional Patent Application Ser. No. 62/521,252, filed on Jun. 16, 2017 and entitled "SYSTEM AND METHOD FOR SAFETY SYRINGE" and U.S. Provisional Patent Application Ser. No. 62/639,614, filed on Mar. 7, 2018 and entitled "SYSTEM AND METHOD FOR MICRODOSE INJECTION." This application includes subject matter similar to the subject matter described in the following co-owned U.S. patent applications: (1) Ser. No. 14/696,342, filed Apr. 24, 2015, entitled "SYSTEM AND METHOD FOR SAFETY SYRINGE"; (2) Ser. No. 14/543,787, filed Nov. 17, 2014, entitled "SYSTEM AND METHOD FOR DRUG DELIVERY WITH A SAFETY SYRINGE"; (3) Ser. No. 14/321,706, filed Jul. 1, 2014, entitled "SAFETY SYRINGE"; and (4) Ser. No. 62/416,102, filed Nov. 1, 2016, entitled "SYSTEM AND METHOD FOR SAFETY SYRINGE"; (5) Ser. No. 62/431,382, filed Dec. 7, 2016, entitled "SYSTEM AND METHOD FOR SAFETY SYRINGE"; (6) Ser. No. 62/480,276, filed Mar. 31, 2017, entitled "SYSTEM AND METHOD FOR SAFETY SYRINGE; (7) Ser. No. 62/508,508, filed May 19, 2017, entitled "SYSTEM AND METHOD FOR COLLECTING INJECTION INFORMATION"; (8) Ser. No. 62/542,230, filed Aug. 7, 2017, entitled "CARTRIDGE SAFETY INJECTION SYSTEM AND METHODS"; (9) Ser. No. 15/801,239, filed Nov. 1, 2017, entitled "SYSTEM AND METHOD FOR SAFETY SYRINGE"; (10) Ser. No. 15/801,259, filed Nov. 1, 2017, entitled "SYSTEM AND METHOD FOR SAFETY SYRINGE"; (11) Ser. No. 15/801,281, filed Nov. 1, 2017, entitled "CARTRIDGE SAFETY INJECTION SYSTEM AND METHODS"; and (12) Ser. No. 15/801,304, filed Nov. 1, 2017, entitled "SYSTEM AND METHOD FOR SAFETY SYRINGE". The contents of the above-mentioned applications are fully incorporated herein by reference as though set forth in full.

FIELD OF THE INVENTION

The present invention relates generally to injection systems, devices, and processes for facilitating various levels of control over fluid infusion, and more particularly to systems and methods related to syringes for delivery microliter range doses of fluids in healthcare environments. The present invention also relates to injection systems, devices, and processes with lower delivery and storage profiles/footprints.

BACKGROUND

Millions of syringes, such as that depicted in FIG. 1A (2), are consumed in healthcare environments every day. A typical syringe (2) includes a tubular body (4), a plunger (6), and an injection needle (8). As shown in FIG. 1B, such a syringe (2) may be utilized not only to inject fluid into a patient, but also to withdraw or expel fluid out of or into a container such as a medicine bottle, vial, bag, or other drug containment system (10). Indeed, due to regulatory constraints in some countries such as the United States as well as sterility maintenance concerns, upon use of a medicine bottle (10) with a syringe (2) as shown in a particular patient's environment, such medicine bottle may only be utilized with a single patient and then must be disposed of—causing significant medical waste from bottle and remaining medicine disposal, and even contributing to periodic shortages of certain critical drugs.

Referring to FIG. 2A, three Luer-type syringes (12) are depicted, each having a Luer fitting geometry (14) disposed distally, so that they may be coupled with other devices having similar mating geometry, such as the Luer manifold assembly (16) depicted in FIG. 2B. The Luer manifold assembly of FIG. 2B may be used to administer liquid drugs to the patient intravenously with or without the use of an intravenous infusion bag. The Luer fittings (14) of the syringes of FIG. 2A may be termed the "male" Luer fittings, while those of FIG. 2B (18) may be termed the "female" Luer fittings; one of the Luer interfaces may be threaded (in which case the configuration may be referred to as a "Luer lock" configuration) so that the two sides may be coupled by relative rotation, which may be combined with compressive loading. In other words, in one Luer lock embodiment, rotation, possibly along with compression, may be utilized to engage threads within the male fitting (14) which are configured to engage a flange on the female fitting (18) and bring the devices together into a fluid-sealed coupling. In another embodiment, tapered interfacing geometries may be utilized to provide for a Luer engagement using compression without threads or rotation (such a configuration may be referred to as a "slip-on" or "conical" Luer configuration). While such Luer couplings are perceived to be relatively safe for operators, there is risk of medicine spilling/leaking and parts breakage during the loading to provide a Luer coupling. The use of needle injection configurations, on the other hand, carries with it the risk of a sharp needle contacting or poking a person or structure that is not desired. For this reason, so called "safety syringes" have been developed.

One embodiment of a safety syringe (20) is shown in FIG. 3, wherein a tubular shield member (22) is spring biased to cover the needle (8) when released from a locked position relative to the syringe body (4). Another embodiment of a safety syringe (24) is shown in FIGS. 4A-4B. With such a configuration, after full insertion of the plunger (6) relative to the syringe body (4), the retractable needle (26) is configured to retract (28, 26) back to a safe position within the tubular body (4), as shown in FIG. 4B. Such a configuration which is configured to collapse upon itself may be associated with blood spatter/aerosolization problems, the safe storage of pre-loaded energy which may possible malfunction and activate before desirable, loss of accuracy in giving full-dose injections due to residual dead space within the spring compression volume, and/or loss of retraction velocity control which may be associated with pain and patient anxiety.

Further complicating the syringe marketplace is an increasing demand for pre-filled syringe assemblies such as those depicted in FIGS. 5A and 5B, which generally include a syringe body, or "drug enclosure containment delivery system", (34), a plunger tip, plug, or stopper (36), and a distal seal or cap (35) which may be fitted over a Luer type interface (FIG. 5A shows the cap 35 in place; FIG. 5B has the cap removed to illustrate the Luer interface (14). Liquid medicine may reside in the volume, or medicine reservoir, (40) between the distal seal (35) and the distal end (37) of the stopper member (36). The stopper member (36) may include a standard butyl rubber material and may be coated, such as with a biocompatible lubricious coating (e.g., polytetrafluoroethylene ("PTFE")), to facilitate preferred sealing and relative motion characteristics against the associated syringe body (34) structure and material. The proximal end of the syringe body (34) in FIG. 5B includes a conventional integral syringe flange (38), which is formed integral to the material of the syringe body (34). The flange (38) is configured to extend radially from the syringe body (34) and may be configured to be a full circumference, or a partial circumference around the syringe body (34). A partial flange is known as a "clipped flange" while the other is known as a "full flange." The flange is used to grasp the syringe with the fingers to provide support for pushing on the plunger to give the injection. The syringe body (34) preferably includes a translucent material such as a glass or polymer. To form a contained volume within the medicine chamber or reservoir (40), and to assist with expulsion of the associated fluid through the needle, a stopper member (36) may be positioned within the syringe body (34). The syringe body may define a substantially cylindrical shape (i.e., so that a plunger tip 36 having a circular cross sectional shape may establish a seal against the syringe body), or be configured to have other cross sectional shapes, such as an ellipse.

Such assemblies are desirable because they may be standardized and produced with precision in volume by the few manufacturers in the world who can afford to meet all of the continually changing regulations of the world for filling, packaging, and medicine/drug interfacing materials selection and component use. Such simple configurations, however, generally will not meet the new world standards for single-use, safety, auto-disabling, and anti-needle-stick. Thus certain suppliers have moved to more "vertical" solutions, such as that (41) featured in FIG. 5C, which attempts to meet all of the standards, or at least a portion thereof, with one solution; as a result of trying to meet these standards for many different scenarios, such products may have significant limitations (including some of those described above in reference to FIGS. 3-4B) and relatively high inventory and utilization expenses.

Moreover, many pre-filled syringe assemblies include pre-filled cartridges that are used in injection systems. Assembling pre-filled cartridges with needle hub assemblies presents challenges for meeting safety, auto-disabling, and anti-needle-stick standards. For instance, some safe needle retraction systems require more precise positioning of components during assembly, which may not be compatible with various tolerances of existing pre-filled cartridges.

There is a need for injection systems which address shortcomings of currently-available configurations. In particular, there is a need for injection systems (e.g., pre-filled) that have lower shipping and storage profiles. Such low-profile storage injection systems reduce the space requirements for shipping and storage (e.g., refrigeration). Low-profile storage injection systems can also be used with patient specific automated medication dispensing and management systems. There is a further need for injection systems that perform accurately in the microliter range. It is also desirable that such syringe assemblies may utilize the existing and relatively well-controlled supply chain of conventionally delivered pre-filled cartridges and other off-the-shelf components, and the corresponding assembly machinery and personnel. Further, there is a need for injections systems that facilitate both injection and withdrawal of fluid in the microliter range.

SUMMARY

Embodiments are directed to injection systems. In particular, the embodiments are directed to low-profile storage injection systems and microliter range injection systems that include at least some off-the-shelf syringe components.

In one embodiment, a system for injecting includes a syringe body having proximal and distal ends, a syringe interior, and a syringe flange at the proximal end thereof. The system also includes a stopper member disposed in the syringe interior. The system further includes a latching member disposed in the stopper member. Moreover, the system includes a plunger member having a notch at a distal end thereof configured to engage the latching member, thereby directly coupling the stopper member to the plunger member. The plunger member, when directly coupled to the stopper member, is configured to be manipulated to insert the stopper member distally in the syringe interior relative to the syringe body.

In one or more embodiments, the system also includes a finger flange coupled to the syringe flange, where the finger flange is configured to removably couple the plunger member to the syringe body when the plunger member is not directly coupled to the stopper member. The finger flange may include a side opening configured to allow the syringe flange to pass at least partially therethrough and at least partially into an interior of the finger flange. The finger flange may include a proximally facing opening configured to receive the distal end of the plunger member. The finger flange may also include a proximally opening funnel disposed around the proximally facing opening and configured to direct the distal end of the plunger member into the proximally facing opening.

In one or more embodiments, the system also includes a Luer connector coupled to the distal end of the syringe body. The stopper member may include a proximally opening funnel at a proximal end thereof, where the proximally opening funnel is configured to direct the distal end of the plunger member into the stopper member.

In one or more embodiments, the notch is a recessed ring around the distal end of the plunger member. The latching member may include an arm extending distally and radially inward to prevent proximal movement of the plunger member, when the plunger member is directly coupled to the stopper member.

In another embodiment, a method for injection includes providing an injection system. The injection system includes a syringe body having proximal and distal ends, a syringe interior, and a syringe flange at the proximal end thereof. The system also includes a stopper member disposed in the syringe interior. The system further includes a latching member disposed in the stopper member. Moreover, the system includes a finger flange coupled to the syringe flange. In addition, the system includes a plunger member removably coupled to the syringe body by the finger flange, the plunger member having a notch at a distal end thereof. The method also includes removing the plunger member from the finger flange. The method further includes inserting the plunger member at least partially into the syringe interior and the stopper member such that the latching member engages the notch to couple the plunger member to the stopper member. In addition, the method includes manipulating the plunger member to insert the stopper member distally in the syringe interior relative to the syringe body.

In one or more embodiments, the finger flange includes a proximally facing opening, where inserting the plunger member at least partially into the syringe interior and the stopper member includes inserting the plunger member at least partially through the proximally facing opening. The finger flange may also include a proximally opening funnel disposed around the proximally facing opening. The method also includes the proximally opening funnel directing the distal end of the plunger member into the proximally facing opening. The injection system may also include a Luer connector coupled to the distal end of the syringe body. The method also includes coupling a needle to the syringe body using the Luer connector. The stopper member may include a proximally opening funnel at a proximal end thereof. The method may also include the proximally opening funnel directing the distal end of the plunger member into the stopper member.

In one or more embodiments, the notch includes a recessed ring around the distal end of the plunger member. The latching member may also include an arm extending distally and radially inward to prevent proximal movement of the plunger member, when the plunger member is directly coupled to the stopper member.

In still another embodiment, a system for injecting includes a syringe body having proximal and distal ends, a syringe interior, and a syringe flange at the proximal end thereof. The system also includes a stopper member disposed in the syringe interior. The system further includes a plunger member coupled to the stopper member and configured to be manipulated to insert the stopper member distally in the syringe interior relative to the syringe body. The plunger member includes a plurality of segments of increasing diameter. The segments are configured to nest within each other in a collapsed configuration.

In one or more embodiments, the segments are configured to telescope from each other and lock in an extended configuration. The plunger may include three or four segments.

In yet another embodiment, a method for injecting includes providing an injection system. The injection system includes a syringe body having proximal and distal ends, a syringe interior, and a syringe flange at the proximal end thereof. The system also includes a stopper member disposed in the syringe interior. The system further includes a plunger member coupled to the stopper member and including a proximal end pad and a plurality of segments of increasing diameter. The segments are nested within each other in a collapsed configuration. The method also includes moving the proximal end pad of the plunger member proximally relative to the syringe body to telescope the segments from each other and to lock the segments in an extended configuration. The method further includes manipulating the plunger member, with the segments in the extended configuration, to insert the stopper member distally in the syringe interior relative to the syringe body.

In one or more embodiments, the plunger includes three or four segments.

In another embodiment, a system for injecting includes a syringe body having proximal and distal ends, a syringe interior, and a syringe flange at the proximal end thereof. The system also includes a stopper member disposed in the syringe interior. The system further includes a plunger member coupled to the stopper member and configured to be manipulated to insert the stopper member distally in the syringe interior relative to the syringe body. The plunger member includes a plurality of segments coupled to each other with an elastic member. Moreover, the system includes a restraining member to hold the segments in a non-aligned configuration with the elastic member in an expanded state.

In one or more embodiments, the elastic member is biased to move from the expanded state to a contracted state, when the restraining member is removed, thereby moving the segments to an aligned configuration. The restraining member may be a wrapper for the system.

In still another embodiment, a method for injecting includes providing an injection system. The injection system includes a syringe body having proximal and distal ends, a syringe interior, and a syringe flange at the proximal end thereof. The system also includes a stopper member disposed in the syringe interior. The system further includes a plunger member coupled to the stopper member and including a plurality of segments coupled to each other with an elastic member. The segments are held in a non-aligned configuration with the elastic member in an expanded state by a restraining member. The method also includes removing the restraining member to allow the elastic member to move from the expanded state to a contracted state, thereby moving the segments to an aligned configuration. The method further includes manipulating the plunger member, with the segments in the aligned configuration, to insert the stopper member distally in the syringe interior relative to the syringe body.

In one or more embodiments, the restraining member is a wrapper for the system.

In yet another embodiment, a system for injecting includes a syringe body having proximal and distal ends, a syringe interior, and a syringe flange at the proximal end thereof. The system also includes a stopper member disposed in the syringe interior. The system further includes a plunger member coupled to the stopper member and configured to be manipulated to insert the stopper member distally in the syringe interior relative to the syringe body. The plunger member includes a plurality of segments. The plunger member is configured to be folded such that a first segment of the plurality of segments is adjacent a second segment of the plurality of segments when the plunger member is in a folded configuration.

In one or more embodiments, the plunger member also includes a latching member configured to removably couple the first segment to the syringe body when the plunger member is in the folded configuration. The system may also include a biasing member configured to move the plunger member from the folded configuration into a straight configuration.

In another embodiment, a method for injecting includes providing an injection system. The injection system includes a syringe body having proximal and distal ends, a syringe interior, and a syringe flange at the proximal end thereof. The system also includes a stopper member disposed in the syringe interior. The system further includes a plunger member coupled to the stopper member, and including a plurality of segments. The plunger member is folded in a folded configuration such that a first segment of the plurality of segments is adjacent a second segment of the plurality of segments. The method also includes allowing the plunger member to move from the folded configuration to a straight configuration. The method further includes manipulating the plunger member, with the segments in the straight configuration, to insert the stopper member distally in the syringe interior relative to the syringe body.

In one or more embodiments, allowing the plunger member to move from the folded configuration to the straight configuration includes manually moving the plunger member from the folded configuration to the straight configuration. The system may also include a biasing member. Allowing the plunger member to move from the folded configuration to the straight configuration may include removing a restraining member from the injection system. The restraining member may be a wrapper for the system.

In still another embodiment, a system for injecting includes a syringe body having proximal and distal ends, a syringe interior, and a syringe flange at the proximal end thereof. The system also includes a stopper member disposed in the syringe interior. The system further includes a plunger member coupled to the stopper member. The plunger member includes a rotatable member configured to insert the stopper member distally in the syringe interior relative to the syringe body with rotation of the rotatable member. The plunger member further includes a proximal portion proximal of the rotatable member configured to be moved distally to also insert the stopper member distally in the syringe interior relative to the syringe body.

In one or more embodiments, moving the proximal portion distally to also insert the stopper member distally in the syringe interior relative to the syringe body ejects about 50 microliters of fluid from the syringe interior. The system may also include a safety member removably coupled to the proximal portion of the plunger member to prevent distal movement thereof. The system may also include a finger flange coupled to the syringe flange.

In yet another embodiment, a method for injecting includes providing an injection system. The injection system includes a syringe body having proximal and distal ends, a syringe interior, and a syringe flange at the proximal end thereof. The system also includes a stopper member disposed in the syringe interior. The system further includes a plunger member coupled to the stopper member. The plunger member includes a rotatable member, and a proximal portion proximal of the rotatable. The method also includes rotating the rotatable member with the syringe body in a vertical position to insert the stopper member distally in the syringe interior relative to the syringe body and eject air bubbles from the syringe interior and/or eject air from a needle interior The method further includes moving the proximal portion distally to also insert the stopper member distally in the syringe interior relative to the syringe body.

In one or more embodiments, moving the proximal portion distally to also insert the stopper member distally in the syringe interior relative to the syringe body ejects about 50 microliters of fluid from the syringe interior. The system may also include a safety member removably coupled to the proximal portion of the plunger member to prevent distal movement thereof. The method may also include removing the safety member from the proximal portion before moving the proximal portion distally.

In one embodiment, a system for injecting includes a syringe body having proximal and distal ends, a syringe interior, and a syringe flange at the proximal end thereof. The system also includes a stopper member disposed in the syringe interior. The system further includes a plunger member coupled to the stopper member. Moreover, the system includes a finger flange removably coupled to the syringe flange, the finger flange including a proximally directed screw. In addition, the system includes a rotatable member disposed on the proximally directed screw, the rotatable member having an opening through which the plunger member is disposed. The rotatable member is configured to insert the plunger member and the stopper member coupled thereto distally in the syringe interior relative to the syringe body with rotation of the rotatable member relative to the proximally directed screw.

In one or more embodiments, the plunger member may include an external stop proximal of the rotatable member configured to be moved distally relative to the rotatable member to further insert the plunger member and the stopper member coupled distally in the syringe interior relative to the syringe body. Moving the external stop distally to further insert the stopper member distally in the syringe interior relative to the syringe body may eject about 50 microliters of fluid from the syringe interior.

In one or more embodiments, the system also includes a plunger cap removably coupled to the rotatable member and configured to prevent distal movement of the external stop relative to the rotatable member. The plunger cap may define an opening through which a proximal end of the plunger member is visible from outside of the plunger cap. The opening may be sized and shaped to prevent manual manipulation of the proximal end of the plunger member from outside of the plunger cap. The plunger cap may include a transparent portion through which a proximal end of the plunger member is visible from outside of the plunger cap. The plunger cap may include a proximal end pointed feature. The plunger cap may include a retention feature to removably couple the plunger cap to the rotatable member. The plunger cap may include a first plurality of splines configured to cooperate with a corresponding second plurality of spline on the rotatable member to rotate the rotatable member. The plunger cap may include a knurled outer surface to facilitate manual rotation of the plunger cap.

In one or more embodiments, the finger flange includes an internal surface projection configured to secure the finger flange on the syringe flange. The finger flange may be elastically deformable to secure the finger flange on the syringe flange.

In one or more embodiments, the rotatable member is configured to insert the plunger member and the stopper member coupled thereto distally in the syringe interior relative to the syringe body with rotation of the rotatable member relative to the proximally directed screw in a first direction. The rotatable member may include a ratcheting mechanism to prevent rotation of the rotatable member relative to the proximally directed screw in a second direction opposite to the first direction.

In one or more embodiments, the plunger member includes an internal stop disposed distal of the opening in the rotatable member and sized to prevent passage of the internal stop through the opening, such that the internal stop limits proximal movement of the plunger member. The plunger member may include a visual injection indicator.

In another embodiment, a method for injecting includes providing an injection system. The injection system includes a syringe body having proximal and distal ends, a syringe interior, and a syringe flange at the proximal end thereof. The injection system also includes a fluid disposed in the syringe interior. The injection system further includes a stopper member disposed in the syringe interior. Moreover, the injection system includes a plunger member coupled to the stopper member. In addition, the injection system includes a finger flange removably coupled to the syringe flange, the finger flange including a proximally directed screw. The injection system also includes a rotatable member disposed on the proximally directed screw, the rotatable member having an opening through which the plunger member is disposed. The plunger member includes an external stop proximal of the rotatable member. The injection system further includes a needle assembly with a needle having a needle interior. The method also includes rotating the rotatable member relative to the proximally directed screw with the syringe body in a vertical position to insert the stopper member distally in the syringe interior relative to the syringe body and eject air bubbles from the syringe interior and/or eject air from a needle interior. The method further includes moving the external stop distally relative to the rotatable member to further insert the plunger member and the stopper member coupled thereto distally in the syringe interior relative to the syringe body, thereby ejecting the fluid from the syringe interior.

In one or more embodiments, moving the external stop distally to further insert the stopper member distally in the syringe interior relative to the syringe body ejects about 50 microliters of the fluid from the syringe interior.

In one or more embodiments, the system also includes a plunger cap removably coupled to the rotatable member to prevent distal movement of the external stop relative to the rotatable member. The method also includes rotating the rotatable member relative to the proximally directed screw by rotating the plunger cap relative to the proximally directed screw. The method further includes removing the plunger cap from the rotatable member before moving the external stop distally relative to the rotatable member.

In one or more embodiments, the plunger cap defines an opening. The method also includes the opening in the plunger cap allowing a proximal end of the plunger member to be visible from outside of the plunger cap. The method may include the plunger cap preventing manual manipulation of the proximal end of the plunger member from outside of the plunger cap. The plunger cap may include a transparent portion. The method may include the transparent portion of the plunger cap allowing a proximal end of the plunger member to be visible from outside of the plunger cap. The plunger cap may include a proximal end pointed feature.

In one or more embodiments, the method also includes elastically deforming the finger flange to secure the finger flange on the syringe flange. The method may include rotating the rotatable member relative to the proximally directed screw in a first direction, and preventing rotation of the rotatable member relative to the proximally directed screw in a second direction opposite to the first direction.

In one or more embodiments, the plunger member includes an internal stop disposed distal of the opening in the rotatable member. The method also includes the internal stop preventing proximal movement of the plunger member such that the internal stop moves proximally through the opening. The method may include the external stop proximally relative to the rotatable member after moving the external stop distally relative to the rotatable member to withdraw the plunger member and the stopper member coupled thereto proximally in the syringe interior relative to the syringe body, thereby pulling a second fluid into the syringe interior. The external stop may be moved proximally relative to the rotatable member about a same distance that the external stop is moved distally relative to the rotatable member to place the internal stop in contact with a distally facing surface of the rotatable member.

In one or more embodiments, the method also includes rotating the rotatable member relative to the proximally directed screw to a distal end position before moving the external stop distally relative to the rotatable member to further insert the plunger member and the stopper member coupled thereto distally in the syringe interior relative to the syringe body. The method may also include moving the external stop distally relative to the rotatable member to insert the plunger member to a distal end of the syringe interior.

In still another embodiment, a system for injecting includes a syringe body having proximal and distal ends, a syringe interior, and a syringe flange at the proximal end thereof. The system also includes stopper member disposed in the syringe interior. The system further includes plunger member coupled to the stopper member. Moreover, the system includes finger flange removably coupled to the syringe flange, the finger flange including a proximally directed screw; and. In addition, the system includes rotatable member disposed on the proximally directed screw, the rotatable member having an opening through which the plunger member is disposed. The plunger member includes internal and external stops disposed of distal and proximal the rotatable member respectively. The internal and external stops are respectively sized to prevent passage of the internal and external stops through the opening in the rotatable member, such that the internal and external stops respectively limit proximal and distal movement of the plunger member. When the plunger member is positioned such that the internal stop is in contact with a distally facing surface of the rotatable member, a length of the plunger member between a proximally facing surface of the rotatable member and the external stop defines a gap. The rotatable member is configured to insert the plunger member and the stopper member coupled thereto distally in the syringe interior relative to the syringe body with rotation of the rotatable member relative to the proximally directed screw.

In one or more embodiments, the external stop is configured to be moved distally relative to the rotatable member to further insert the plunger member and the stopper member coupled distally in the syringe interior relative to the syringe body. Moving the external stop distally to further insert the stopper member distally in the syringe interior relative to the syringe body may close the gap to inject a predetermined volume of medicine from the syringe interior into a patient. The predetermined volume of medicine injected may be between about 5 microliters and about 250 microliters. The predetermined volume of medicine injected may be about 50 microliters.

In one or more embodiments, the system also includes a plunger cap removably coupled to the rotatable member and configured to prevent distal movement of the external stop relative to the rotatable member. The plunger cap may be sized and shaped to prevent a syringe operator from prematurely closing the gap between the plunger rod external stop and the rotatable member. The plunger cap may define an opening through which a proximal end of the plunger member is visible from outside of the plunger cap. The opening may be sized and shaped to prevent manual manipulation of the proximal end of the plunger member from outside of the plunger cap. The plunger cap may include a transparent portion through which a proximal end of the plunger member is visible from outside of the plunger cap. The plunger cap may include a proximal end pointed feature. The plunger cap may include a retention feature to removably couple the plunger cap to the rotatable member. The plunger cap may include a first plurality of splines configured to cooperate with a corresponding second plurality of spline on the rotatable member to rotate the rotatable member. The plunger cap may include a knurled outer surface to facilitate manual rotation of the plunger cap. The plunger cap may surround at least a portion of the gap.

In one or more embodiments, the finger flange includes an internal surface projection configured to secure the finger flange on the syringe flange. The finger flange may be elastically deformable to secure the finger flange on the syringe flange.

In one or more embodiments, the rotatable member is configured to insert the plunger member and the stopper member coupled thereto distally in the syringe interior relative to the syringe body with rotation of the rotatable member relative to the proximally directed screw in a first direction. The rotatable member may include a ratcheting mechanism to prevent rotation of the rotatable member relative to the proximally directed screw in a second direction opposite to the first direction.

In one or more embodiments, the plunger member including a visual injection indicator. The rotatable member may include at least one deflectable spring arm, where upon full insertion of the plunger member, the at least one deflectable spring arm snaps over a notch formed on the plunger member, thereby causing a mechanical click to be felt and/or heard by a user to provide tactile and/or audible feedback after a dose is given.

In yet another embodiment, a system for injecting includes a syringe body having proximal and distal ends, a syringe interior, and a syringe flange at the proximal end thereof. The system also includes a stopper member disposed in the syringe interior. The system further includes a plunger member coupled to the stopper member. Moreover, the system includes a finger flange removably coupled to the syringe flange, the finger flange including a proximally directed screw. In addition, the system includes a rotatable member disposed on the proximally directed screw, the rotatable member having an opening through which the plunger member is disposed. The rotatable member is configured to insert the plunger member and the stopper member coupled thereto distally in the syringe interior relative to the syringe body with rotation of the rotatable member relative to the proximally directed screw.

In one or more embodiments, the plunger member may include an external stop proximal of the rotatable member configured to be moved distally relative to the rotatable member to further insert the plunger member and the stopper member coupled distally in the syringe interior relative to the syringe body. Moving the external stop distally to further insert the stopper member distally in the syringe interior relative to the syringe body may eject about 50 microliters of fluid from the syringe interior.

In one or more embodiments, the system also includes a plunger cap removably coupled to the rotatable member and configured to prevent distal movement of the external stop relative to the rotatable member. The plunger cap may define an opening through which a proximal end of the plunger member is visible from outside of the plunger cap. The opening may be sized and shaped to prevent manual manipulation of the proximal end of the plunger member from outside of the plunger cap. The plunger cap may include a transparent portion through which a proximal end of the plunger member is visible from outside of the plunger cap. The plunger cap may include a proximal end pointed feature. The plunger cap may include a retention feature to removably couple the plunger cap to the rotatable member. The plunger cap may include a first plurality of splines configured to cooperate with a corresponding second plurality of spline on the rotatable member to rotate the rotatable member. The plunger cap may include a knurled outer surface to facilitate manual rotation of the plunger cap.

In one or more embodiments, the finger flange includes an internal surface projection configured to secure the finger flange on the syringe flange. The finger flange may be elastically deformable to secure the finger flange on the syringe flange.

In one or more embodiments, the rotatable member is configured to insert the plunger member and the stopper member coupled thereto distally in the syringe interior relative to the syringe body with rotation of the rotatable member relative to the proximally directed screw in a first direction. The rotatable member may include a ratcheting mechanism to prevent rotation of the rotatable member relative to the proximally directed screw in a second direction opposite to the first direction.

In one or more embodiments, the plunger member includes an internal stop disposed distal of the opening in the rotatable member and sized to prevent passage of the internal stop through the opening, such that the internal stop limits proximal movement of the plunger member. The plunger member may include a visual injection indicator.

In another embodiment, a method for injecting includes providing an injection system. The injection system includes a syringe body having proximal and distal ends, a syringe interior, and a syringe flange at the proximal end thereof. The injection system also includes a fluid disposed in the syringe interior. The injection system further includes a stopper member disposed in the syringe interior. Moreover, the injection system includes a plunger member coupled to the stopper member. In addition, the injection system includes a finger flange removably coupled to the syringe flange, the finger flange including a proximally directed screw. The injection system also includes a rotatable member disposed on the proximally directed screw, the rotatable member having an opening through which the plunger member is disposed. The plunger member includes an external stop proximal of the rotatable member. The injection system further includes a needle assembly with a needle having a needle interior. The method also includes rotating the rotatable member relative to the proximally directed screw with the syringe body in a vertical position to insert the stopper member distally in the syringe interior relative to the syringe body and eject air bubbles from the syringe interior and/or eject air from a needle interior. The method further includes moving the external stop distally relative to the rotatable member to further insert the plunger member and the stopper member coupled thereto distally in the syringe interior relative to the syringe body, thereby ejecting the fluid from the syringe interior.

In one or more embodiments, moving the external stop distally to further insert the stopper member distally in the syringe interior relative to the syringe body ejects about 50 microliters of the fluid from the syringe interior.

In one or more embodiments, the system also includes a plunger cap removably coupled to the rotatable member to prevent distal movement of the external stop relative to the rotatable member. The method also includes rotating the rotatable member relative to the proximally directed screw by rotating the plunger cap relative to the proximally directed screw. The method further includes removing the plunger cap from the rotatable member before moving the external stop distally relative to the rotatable member.

In one or more embodiments, the plunger cap defines an opening. The method also includes the opening in the plunger cap allowing a proximal end of the plunger member to be visible from outside of the plunger cap. The method may include the plunger cap preventing manual manipulation of the proximal end of the plunger member from outside of the plunger cap. The plunger cap may include a transparent portion. The method may include the transparent portion of the plunger cap allowing a proximal end of the plunger member to be visible from outside of the plunger cap. The plunger cap may include a proximal end pointed feature.

In one or more embodiments, the method also includes elastically deforming the finger flange to secure the finger flange on the syringe flange. The method may include rotating the rotatable member relative to the proximally directed screw in a first direction, and preventing rotation of the rotatable member relative to the proximally directed screw in a second direction opposite to the first direction.

In one or more embodiments, the plunger member includes an internal stop disposed distal of the opening in the rotatable member. The method also includes the internal stop preventing proximal movement of the plunger member such that the internal stop moves proximally through the opening. The method may include the external stop proximally relative to the rotatable member after moving the external stop distally relative to the rotatable member to withdraw the plunger member and the stopper member coupled thereto proximally in the syringe interior relative to the syringe body, thereby pulling a second fluid into the syringe interior. The external stop may be moved proximally relative to the rotatable member about a same distance that the external stop is moved distally relative to the rotatable member to place the internal stop in contact with a distally facing surface of the rotatable member.

In one or more embodiments, the method also includes rotating the rotatable member relative to the proximally directed screw to a distal end position before moving the external stop distally relative to the rotatable member to further insert the plunger member and the stopper member coupled thereto distally in the syringe interior relative to the syringe body. The method may also include moving the external stop distally relative to the rotatable member to insert the plunger member to a distal end of the syringe interior.

In still another embodiment, a system for injecting includes a syringe body having proximal and distal ends, a syringe interior, and a syringe flange at the proximal end thereof. The system also includes stopper member disposed in the syringe interior. The system further includes plunger member coupled to the stopper member. Moreover, the system includes finger flange removably coupled to the syringe flange, the finger flange including a proximally directed screw; and. In addition, the system includes rotatable member disposed on the proximally directed screw, the rotatable member having an opening through which the plunger member is disposed. The plunger member includes internal and external stops disposed of distal and proximal the rotatable member respectively. The internal and external stops are respectively sized to prevent passage of the internal and external stops through the opening in the rotatable member, such that the internal and external stops respectively limit proximal and distal movement of the plunger member. When the plunger member is positioned such that the internal stop is in contact with a distally facing surface of the rotatable member, a length of the plunger member between a proximally facing surface of the rotatable member and the external stop defines a gap. The rotatable member is configured to insert the plunger member and the stopper member coupled thereto distally in the syringe interior relative to the syringe body with rotation of the rotatable member relative to the proximally directed screw.

In one or more embodiments, the external stop is configured to be moved distally relative to the rotatable member to further insert the plunger member and the stopper member coupled distally in the syringe interior relative to the syringe body. Moving the external stop distally to further insert the stopper member distally in the syringe interior relative to the syringe body may close the gap to inject a predetermined volume of medicine from the syringe interior into a patient. The predetermined volume of medicine injected may be between about 5 microliters and about 250 microliters. The predetermined volume of medicine injected may be about 50 microliters.

In one or more embodiments, the system also includes a plunger cap removably coupled to the rotatable member and configured to prevent distal movement of the external stop relative to the rotatable member. The plunger cap may be sized and shaped to prevent a syringe operator from prematurely closing the gap between the plunger rod external stop and the rotatable member. The plunger cap may define an opening through which a proximal end of the plunger member is visible from outside of the plunger cap. The opening may be sized and shaped to prevent manual manipulation of the proximal end of the plunger member from outside of the plunger cap. The plunger cap may include a transparent portion through which a proximal end of the plunger member is visible from outside of the plunger cap. The plunger cap may include a proximal end pointed feature. The plunger cap may include a retention feature to removably couple the plunger cap to the rotatable member. The plunger cap may include a first plurality of splines configured to cooperate with a corresponding second plurality of spline on the rotatable member to rotate the rotatable member. The plunger cap may include a knurled outer surface to facilitate manual rotation of the plunger cap. The plunger cap may surround at least a portion of the gap.

In one or more embodiments, the finger flange includes an internal surface projection configured to secure the finger flange on the syringe flange. The finger flange may be elastically deformable to secure the finger flange on the syringe flange.

In one or more embodiments, the rotatable member is configured to insert the plunger member and the stopper member coupled thereto distally in the syringe interior relative to the syringe body with rotation of the rotatable member relative to the proximally directed screw in a first direction. The rotatable member may include a ratcheting mechanism to prevent rotation of the rotatable member relative to the proximally directed screw in a second direction opposite to the first direction.

In one or more embodiments, the plunger member including a visual injection indicator. The rotatable member may include at least one deflectable spring arm, where upon full insertion of the plunger member, the at least one deflectable spring arm snaps over a notch formed on the plunger member, thereby causing a mechanical click to be felt and/or heard by a user to provide tactile and/or audible feedback after a dose is given.

In one or more embodiments, after an injection has been administered, the plunger member may be withdrawn, while the needle is still inserted in an injection site, to extract a volume of body fluid substantially equal to a volume of medicine which has been injected. For example, the gap between the thumbpad and the finger flange that was closed to inject 50 ml of medicine is opened by pulling proximally on the thumbpad to withdraw the plunger rod to extract 50 ml of fluid from the body. This extraction of liquid is used to minimize changes to the fluid pressure inside a fluid filled organ of the body (e.g., the eye).

The aforementioned and other embodiments of the invention are described in the Detailed Description which follows.

BRIEF DESCRIPTION OF THE DRAWINGS

The foregoing and other aspects of embodiments are described in further detail with reference to the accompanying drawings, in which the same elements in different figures are referred to by common reference numerals, wherein:

FIGS. 15-17 illustrate various aspects of a low-profile storage injection system according to another embodiment.

FIGS. 18-21 illustrate various aspects of a low-profile storage injection system according to another embodiment.

FIGS. 25-30 illustrate various aspects of a low-profile storage injection system according to another embodiment.

FIGS. 36-50 illustrate various aspects of a microdose injection system and a microdose injection method according to two embodiments.

FIGS. 74-75 illustrate various aspects of a microdose injection system according to one embodiment.

FIGS. 76-84 illustrate various aspects of a microdose injection method according to one embodiment.

Figure 1A:
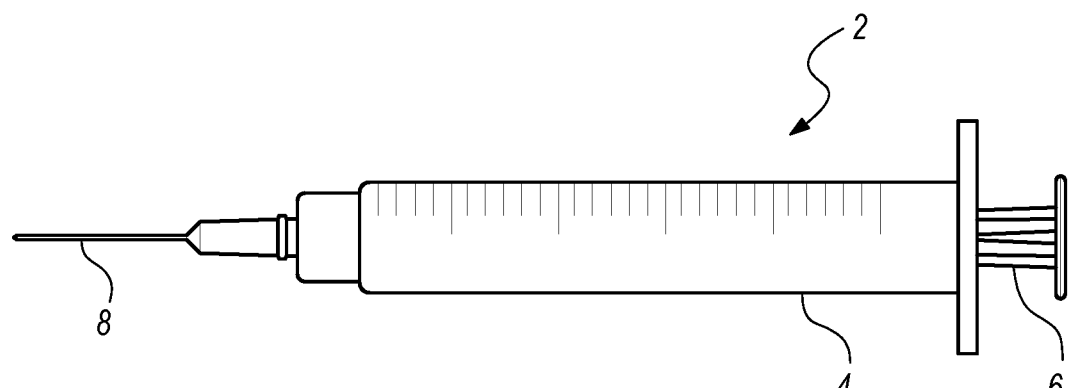
FIGS. 1A-5C illustrate various aspects of conventional injection syringe configurations.
Figure 1B:
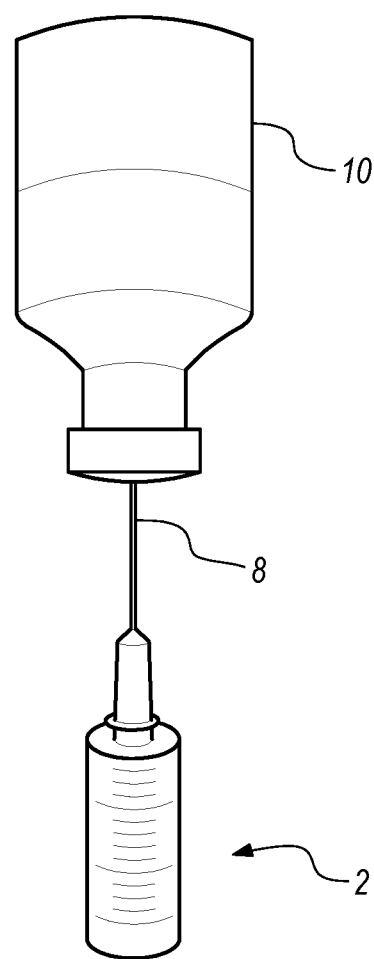
Figure 2A:
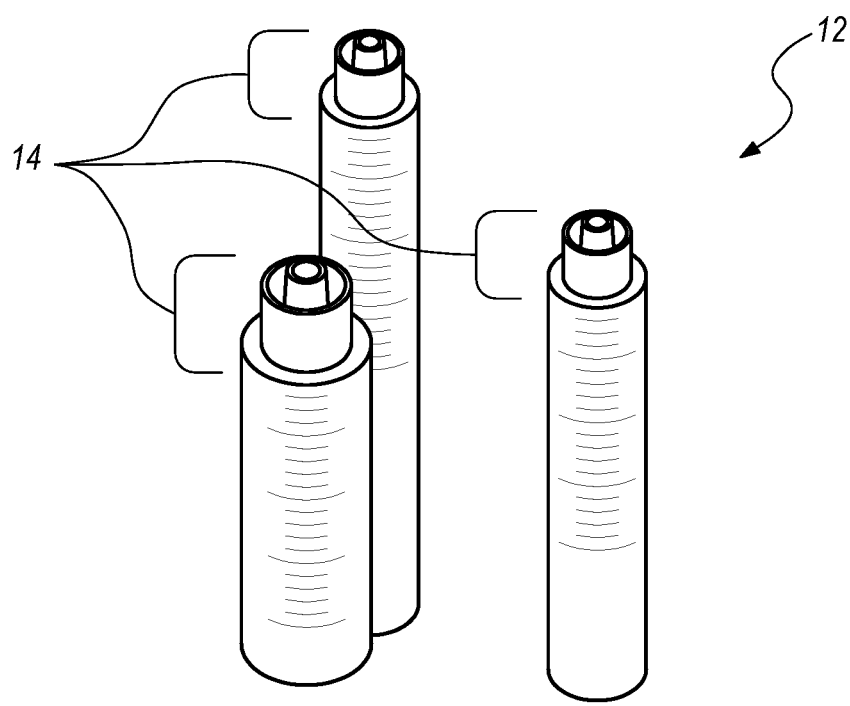
Figure 2B:
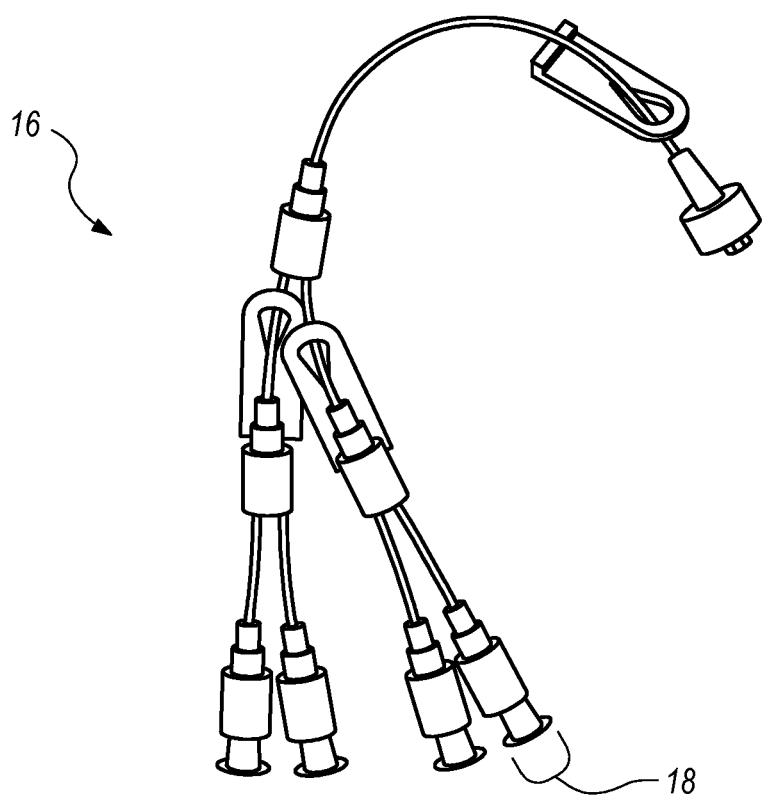
Figure 3:
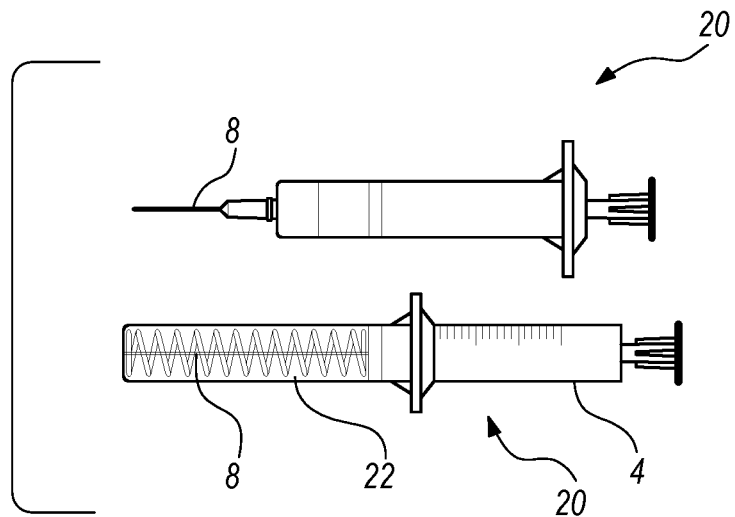
Figure 4A:
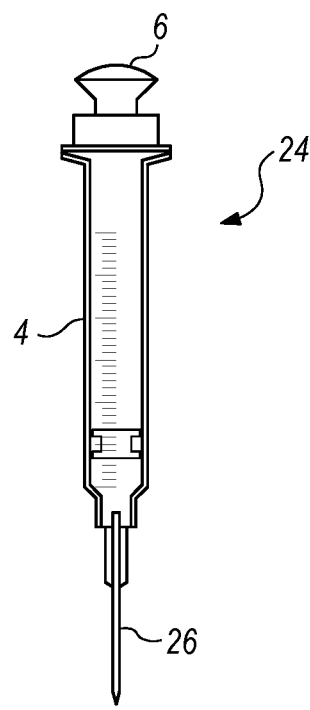
Figure 4B:
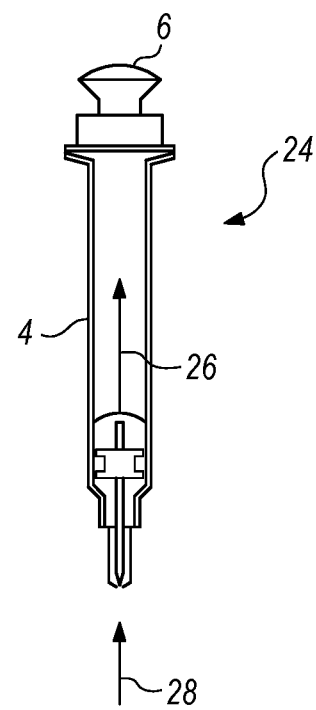
Figure 5A:
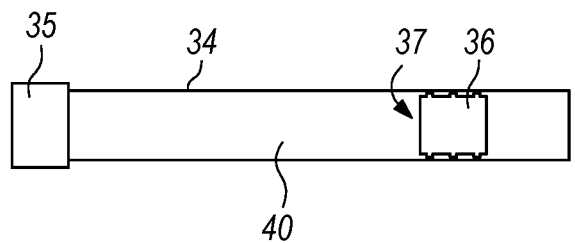
Figure 5B:
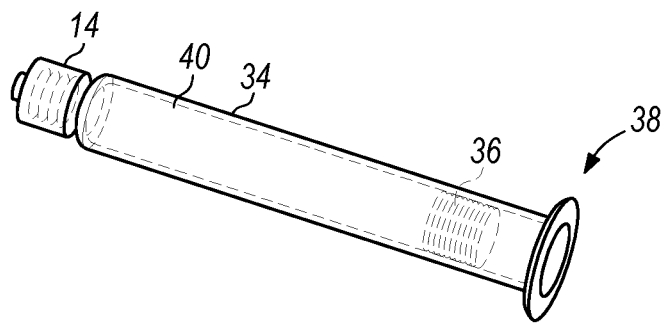
Figure 5C:
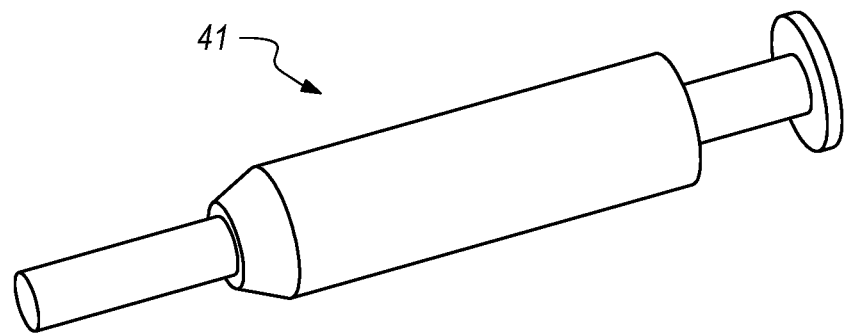

In order to better appreciate how to obtain the above-recited and other advantages and objects of various embodiments, a more detailed description of embodiments is provided with reference to the accompanying drawings. It should be noted that the drawings are not drawn to scale and that elements of similar structures or functions are represented by like reference numerals throughout. It will be understood that these drawings depict only certain illustrated embodiments and are not therefore to be considered limiting of scope of embodiments.

DETAILED DESCRIPTION OF ILLUSTRATED EMBODIMENTS

Low-Profile Storage Injection Systems

Figure 6:
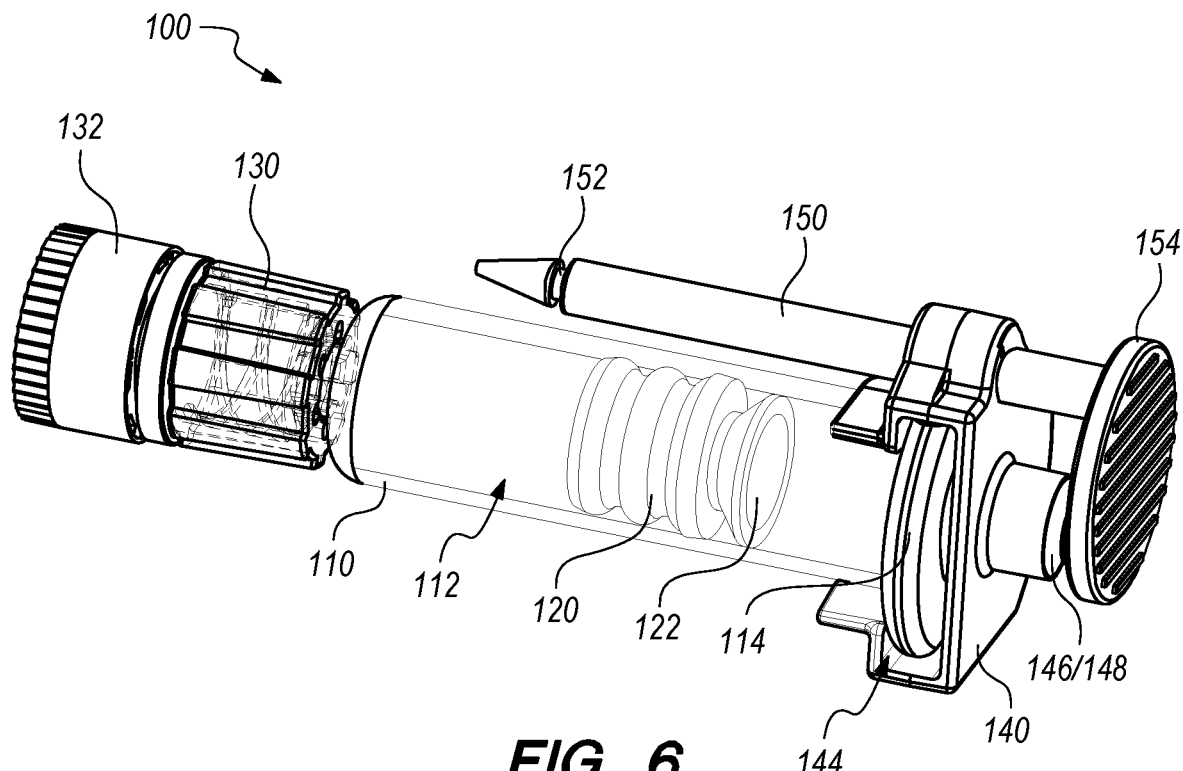
FIGS. 6-14 illustrate various aspects of a low-profile storage injection system according to one embodiment.
Figure 7:
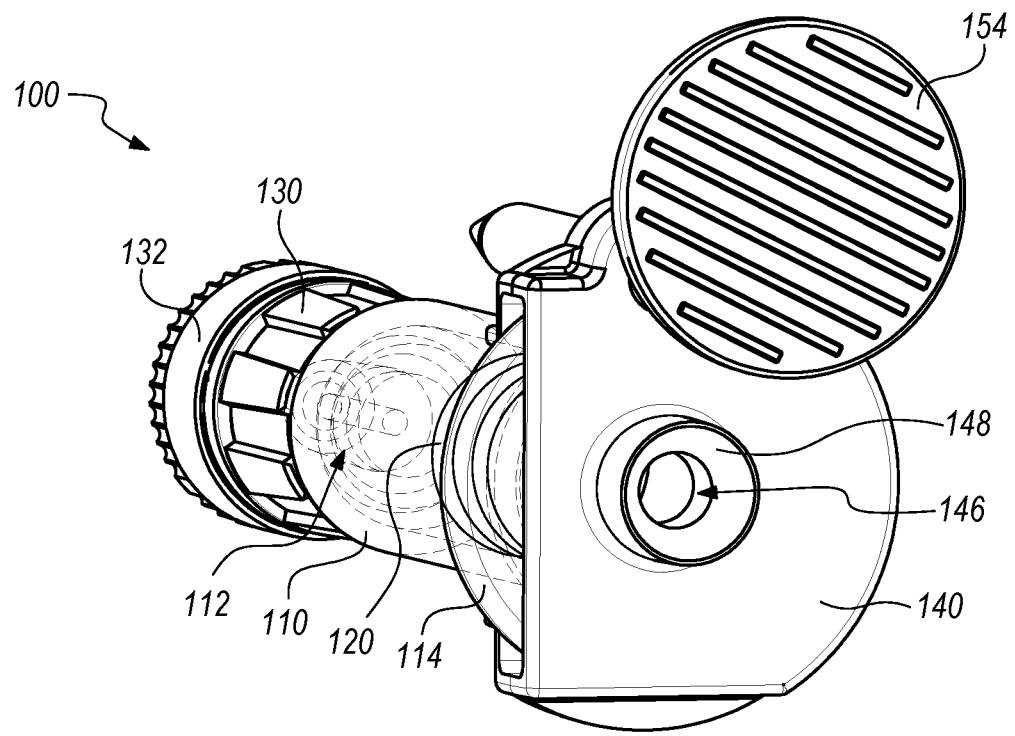

FIGS. 6-13 depict a low-profile storage injection system 100 according to one embodiment. This embodiment solves the problem of overly large storage profile by using a removable plunger member 150 in a "sidecar" configuration. FIGS. 6 and 7 depict the low-profile storage injection system 100 in its shipping/storage configuration. The system 100 includes a syringe body 110 having open proximal and distal ends and defining a syringe interior 112 and a syringe flange 114 at its proximal end. The system 100 also includes a stopper member 120 disposed in the syringe interior 112. The system 100 further includes a connection member 130 (e.g., a Luer lock connector) coupled to the distal end of the syringe body 110. In FIGS. 6 and 7, the connection member 130 also includes a removable cap 132. Moreover, the system 100 includes a finger flange 140 coupled to the syringe body 110 at the syringe flange 114. In addition, the system 100 includes a plunger member 150 configured to move the stopper member 120 distally within the syringe interior 112. In the shipping/storage configuration, the plunger member 150 is coupled to the syringe body once had by the finger flange 140. In particular, the finger flange 140 includes a plunger member storage opening 142 in which the plunger member 150 is disposed in the shipping/storage configuration. Storing the plunger member 150 unconnected from the stopper member 120 allows the stopper member 120 to be in a proximal position while maintaining a relatively lower profile (e.g., shorter length) for storage. Having the stopper member 120 in a proximal position allows storage of injectable substances (e.g., medications) in the injection system 100.

The syringe body 110 and the connection member 130 may be off-the-shelf components. The stopper member 120 may be a modified version of an off-the-shelf stopper (described below).

The finger flange 140 has a side opening 144 configured (e.g., sized and shaped) to allow the finger flange 140 to be slid over the syringe flange 114, thereby coupling the finger flange 140 to the syringe body 110. The finger flange 140 also includes a proximally facing plunger member receiving opening 146 configured (e.g., sized and shaped) to receive a distal end of the plunger member 150 during assembly of the injection system 100. As shown in FIG. 7, the finger flange 140 further includes a proximally opening funnel 148 surrounding and leading into the plunger member receiving opening 146. The funnel 148 is configured (e.g., sized and shaped) to guide the distal end of the plunger member 150 in to the plunger member receiving opening 146 during assembly.

Figure 8:
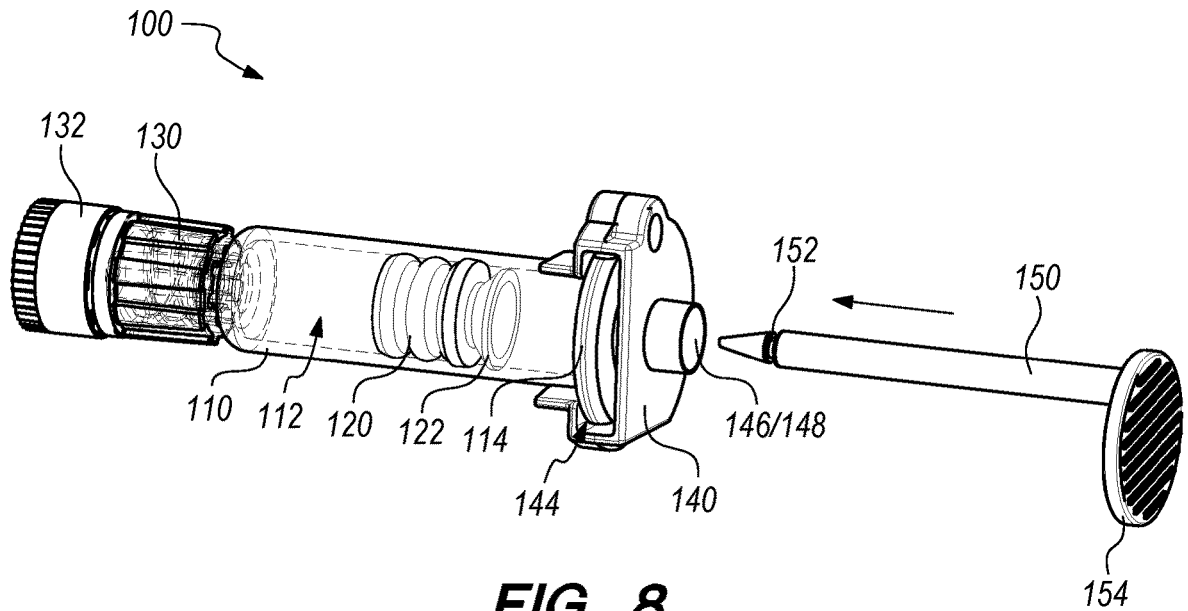

FIG. 8 depicts the next step in assembly of the injection system 100 depicted in FIGS. 6 and 7. In FIG. 8, the injection system 100 has been removed from its shipping/storage location (e.g., a limited size drawer in a patient specific automated medication dispensing and management system), and the plunger member 150 has been removed from the plunger member storage opening 142 in the finger flange 120. The plunger member 150 is aligned with the plunger member receiving opening 146 in the finger flange 140 such that the distal end of the plunger member 150 is adjacent the funnel 148 and the finger flange 140.

Figure 9:
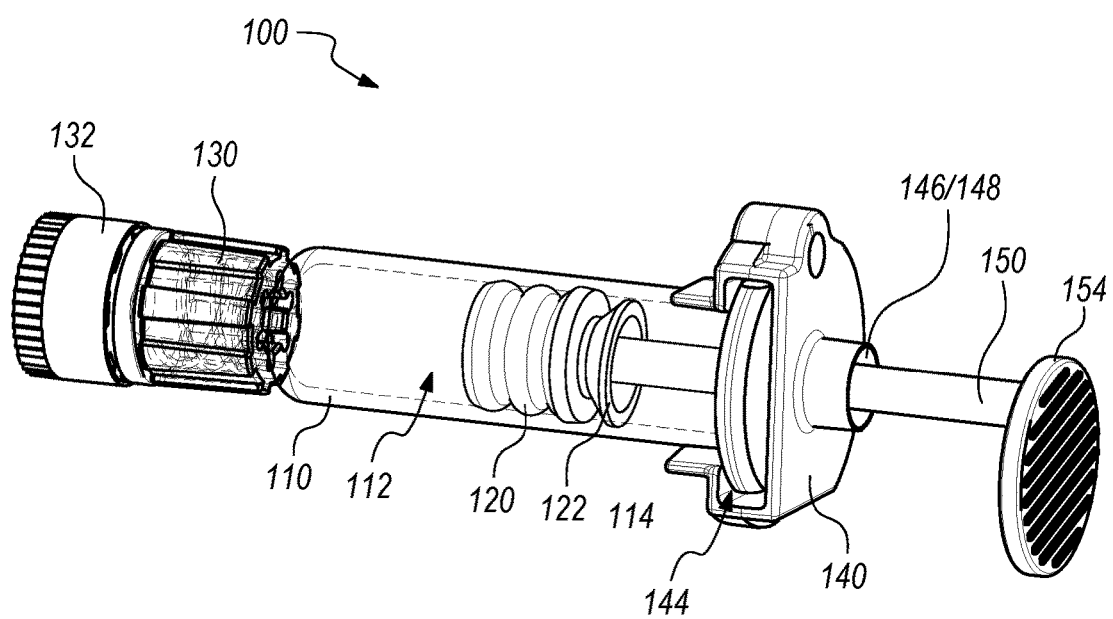

FIG. 9 depicts the next step in assembly of the injection system 100. In this step, the distal end of the plunger member 150 has been inserted into the plunger member receiving opening 146 (optionally guided by the funnel 148), through the open proximal end of the syringe body 110, and into the syringe interior 112 and the stopper member 120. The distal end of the plunger member 150 has been locked into the stopper member 120, as described below, coupling the plunger member 150 in the stopper member 120. After coupling, the plunger member 150 can be used to move the stopper member 120 both proximally and distally relative to the syringe body 110. The injection system 100 depicted in FIG. 9 is almost ready for rejection (after the removable cap 132 has been removed). A needle (not shown) may be coupled to the injection system 100 (e.g., via connection member 130) before injection, or the injection system 100 can be used to inject into a connector corresponding the connection member 130 (e.g., which may be attached to an IV bag).

Figure 10:
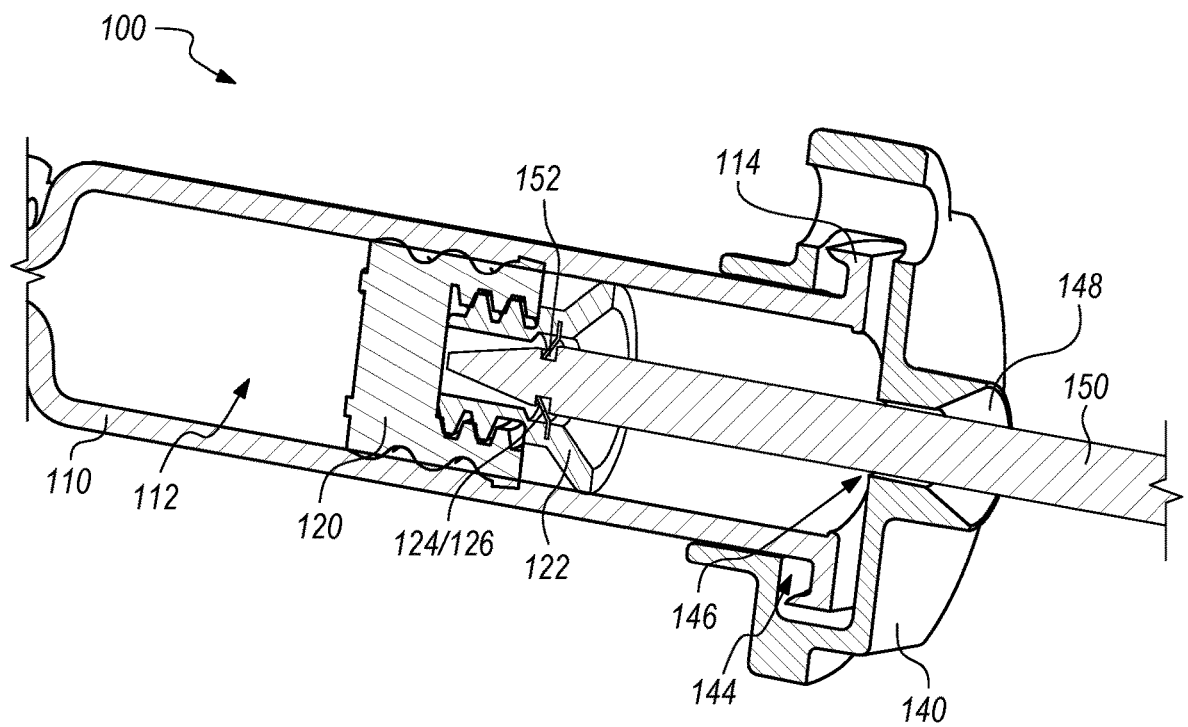
Figure 11:
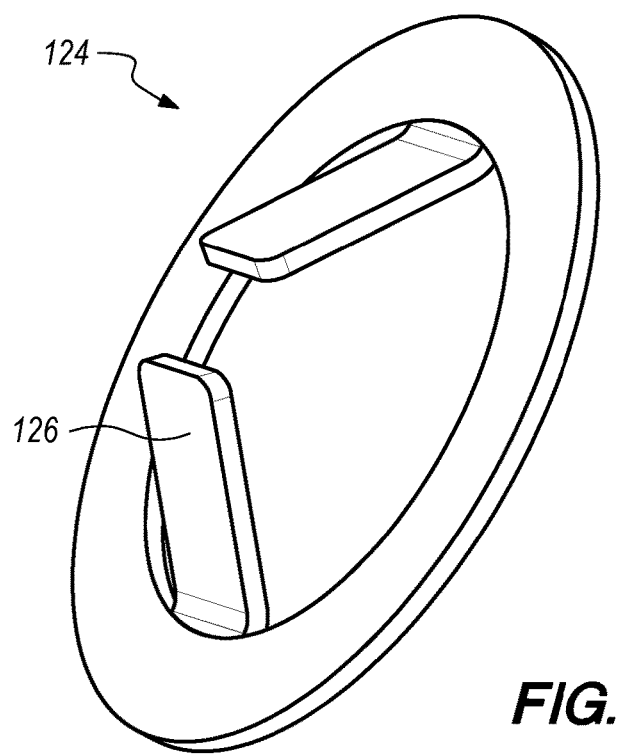
Figure 12:
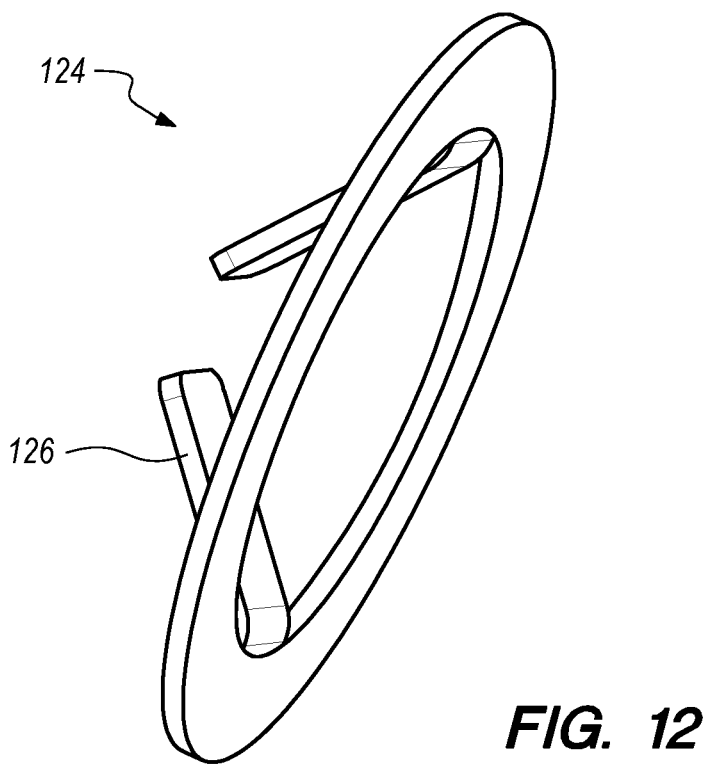

FIG. 10 depicts the injection system 100 depicted in FIGS. 6 to 9 in a detailed longitudinal cross-section view. As shown in FIG. 10, the stopper member 120 includes a proximally opening funnel member 122 configured to guide the distal end of the plunger member 150 into the stopper member 120. The funnel member 122 may be coupled to the stopper member 120 using a standard screw fit mechanism. The funnel member 122 facilitates assembly of the plunger member 150 and the stopper member 120. The stopper member 120 also includes a latching member 124 disposed in the funnel member 122. As shown in FIGS. 11 and 12, the latching member 124 includes a pair of distally and radially inward extending arms 126 configured to allow distal movement of the distal end of the plunger member 150 while preventing proximal movement thereof after assembly.

Figure 13:
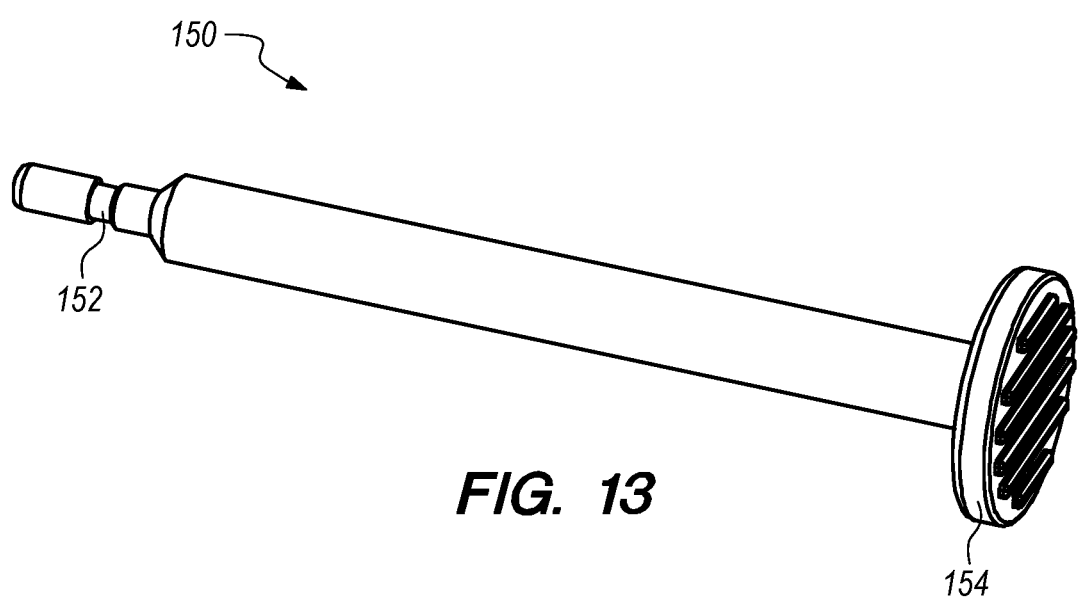

FIG. 13 depicts the plunger member 150, including a recessed ring 152 configured to interact with the arms 126 of the latching member 124 two prevent proximal movement of the plunger member 150 relative to the stopper member 120. In other embodiments, the recessed ring 152 may be one or more notches. The plunger member 150 also includes a proximal end pad 154 configured to facilitate application of distally directed force on the plunger member 150 (e.g., with a user's thumb).

Figure 14:
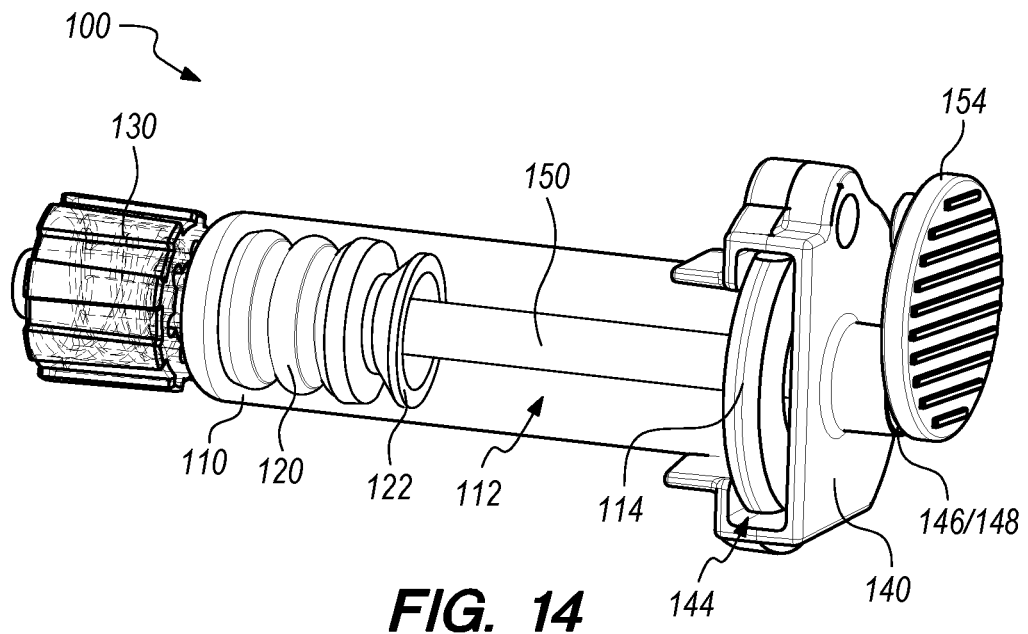

FIG. 14 depicts the injection system 100 depicted in FIGS. 6 to 13 after the removable 132 has been removed from the connection member 130 and the injection system 100 has been used to perform an injection by applying distally directed force on the plunger member 150 to move the stopper member 120 distally in (e.g., to a distal end of) the syringe interior 112.

FIGS. 15 to 21 depict low-profile storage injection systems 100 according to two other related embodiments. These embodiments solve the problem of overly large storage profile by using two similar telescoping plunger members 150. Like the embodiment depicted in FIGS. 6 to 14, these embodiments utilize off-the-shelf syringe bodies 110 and stopper members 120. They also have finger flanges 140.

Figure 15:
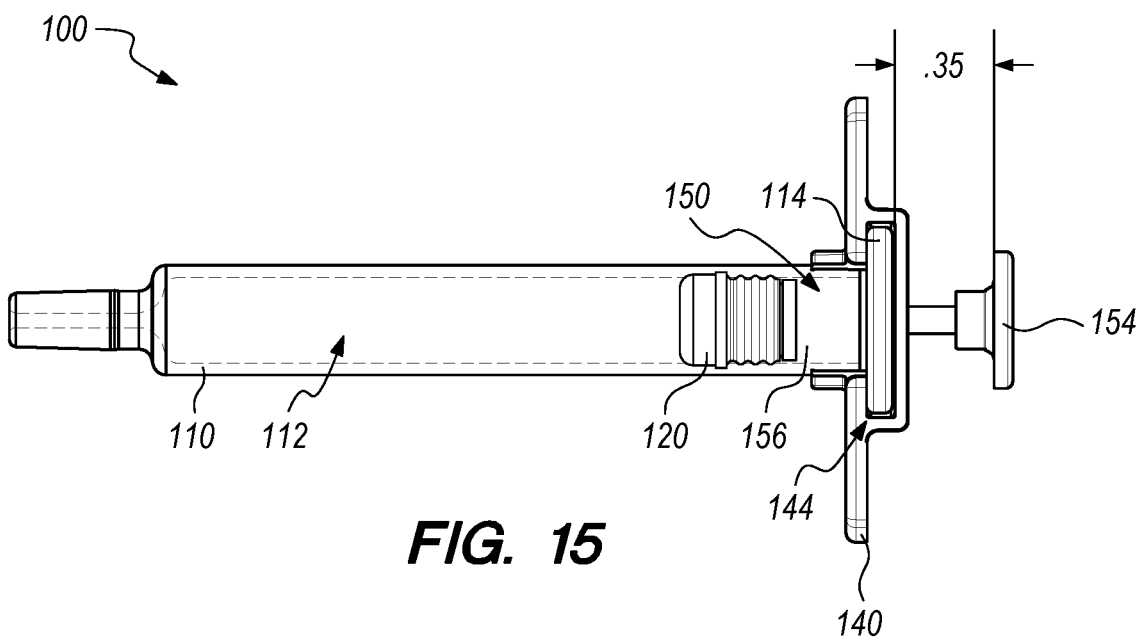

FIGS. 15, 18, and 19 depict the low-profile storage injection systems 100 in their shipping/storage configuration. In these embodiments, the shipping/storage configuration is also called the "collapsed configuration." The embodiment depicted in FIGS. 15 to 17 has a four segment telescoping plunger member 150, while the embodiment depicted in FIGS. 18 to 21 as a three segment telescoping plunger member 150. Accordingly, the embodiment depicted in FIGS. 15 to 17 extends proximally beyond the finger flange 140 by 0.35 inches, while the embodiment depicted in FIGS. 18 to 21 extends proximally beyond the finger flange 140 by 0.46 inches. However, both of these embodiments have significantly lower profiles (e.g., lengths) compared to prefilled injection systems with off-the-shelf, non-telescoping plunger members. Because the plunger members 150 are telescoping, the segments 156 forming the plunger member have different diameters so that the segments can nest within each other in the collapsed configuration.

FIGS. 16 and 20 depict the next step in use of the injection systems 100 depicted in FIGS. 15 and 18, respectively. In this step, a user grasps the proximal end pad 154 on the respective plunger members 150 and pulls proximally to proximally extend the plunger members 150 to their full-length "extended configurations."

FIGS. 17 and 21 depict the next step in and use of the injection systems 100 depicted in FIGS. 15 and 18, respectively. In this step, the user exerts distally directed force on the proximal end pad 154 on the respective plunger members 150, thereby moving the plunger members 150 and the attached stopper members 120 distally in (e.g., to a distal end of) the syringe interior 112 to give an injection.

Figure 22:
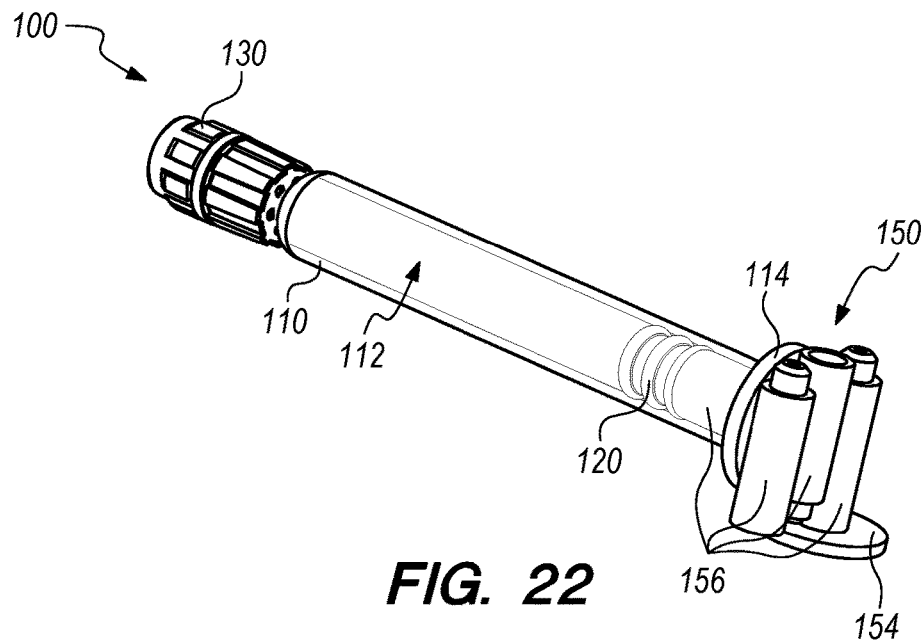
FIGS. 22-24 illustrate various aspects of a low-profile storage injection system according to another embodiment.
Figure 23:
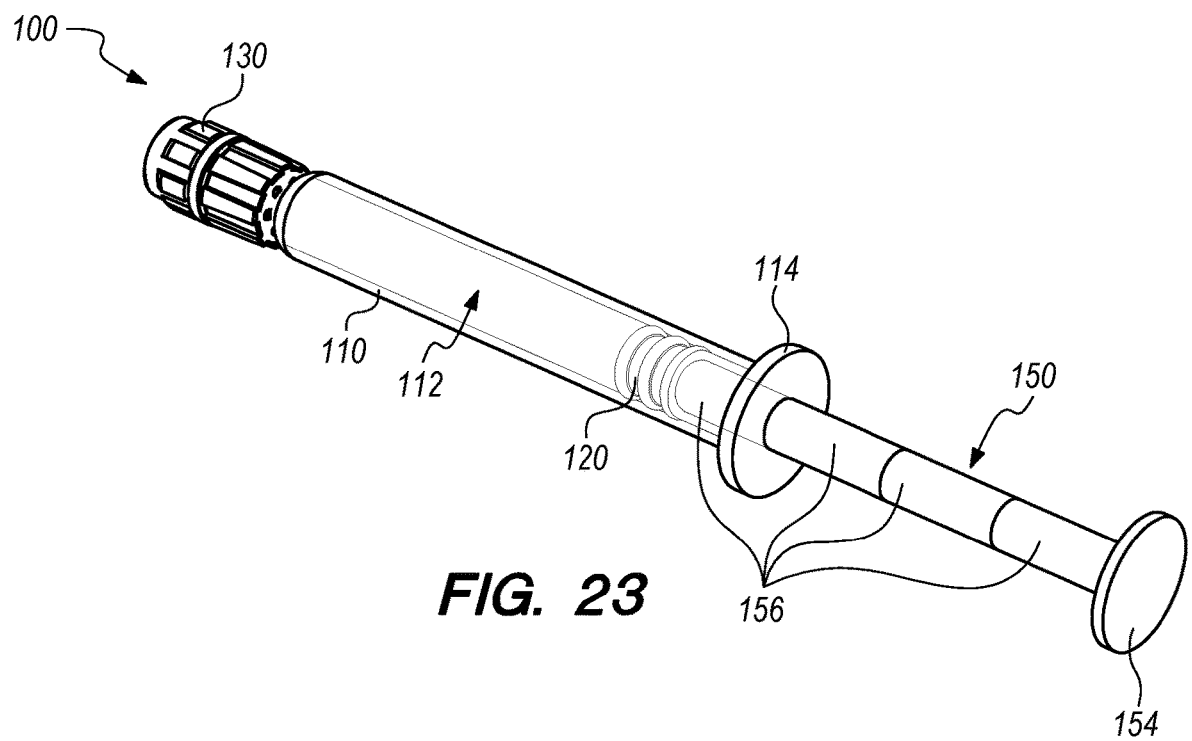
Figure 24:
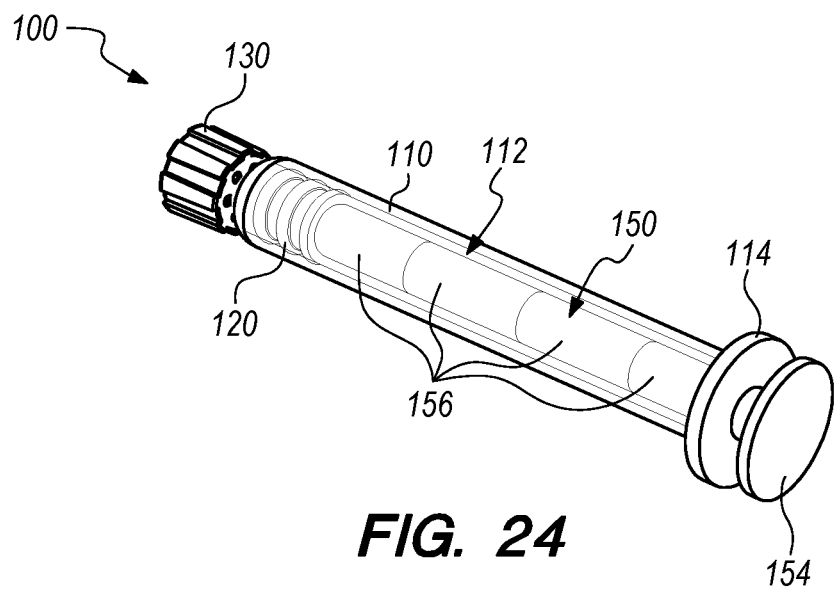

FIGS. 22 to 24 depict a low-profile storage injection system 100 according to still another embodiment. This embodiment solves the problem of overly large storage profile by using a self-erecting plunger member 150. Like the embodiments depicted in FIGS. 6 to 21, this embodiments utilizes off-the-shelf syringe bodies 110 and stopper members 120.

FIG. 22 depict the low-profile storage injection system 100 in its shipping/storage configuration, which is also called the "non-aligned configuration." In the non-aligned configuration, three of the four segments 156 forming the plunger member 150 are disassembled and packed next to each other at the proximal end of the syringe body 110. The three segments 156 are coupled to each other and the stopper member 120 by an elastic member (not shown) that is in an expanded state when the low-profile storage injection system 100 is in its nonaligned configuration for storage. The elastic member is biased to return from the expanded state to a contracted state, but it is prevented from doing so by a restraining member (not shown). In some embodiments, the restraining member may be a wrapper that holds the injection system 100 in the shipping/storage configuration.

FIG. 23 depicts the low-profile storage injection system 100 in its aligned configuration. The injection system 100 may have transitioned from the non-aligned configuration in FIG. 22 to the aligned configuration and FIG. 23 because a user has removed the restraining member (e.g., wrapper) from the injection system 100, thereby allowing the elastic member to return to its contracted state from its expanded state. Contracting the elastic member assembles/erects the plunger member 152 from the segments 156 as shown in FIG. 23. FIG. 24 depicts the low-profile storage injection system 100 after injection.

FIGS. 25 to 30 depict a low-profile storage injection system 100 according to yet another embodiment. This embodiment solves the problem of overly large storage profile by using a hinged plunger member 150. Like the embodiments depicted in FIGS. 6 to 21, this embodiments utilizes off-the-shelf syringe bodies 110, stopper members 120, and connection members 130.

Figure 25:
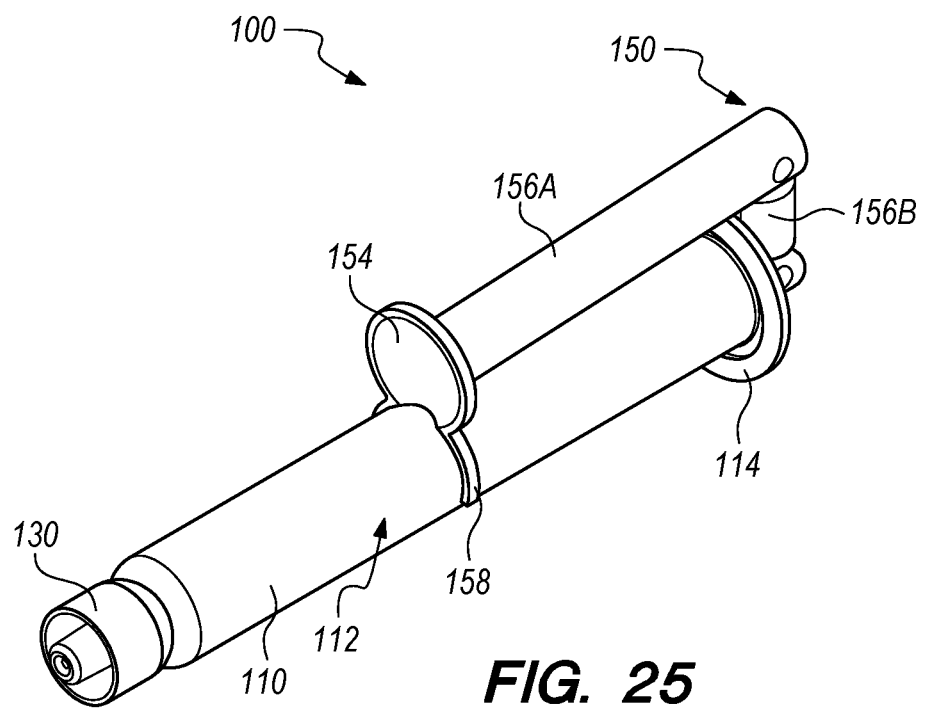
Figure 29:
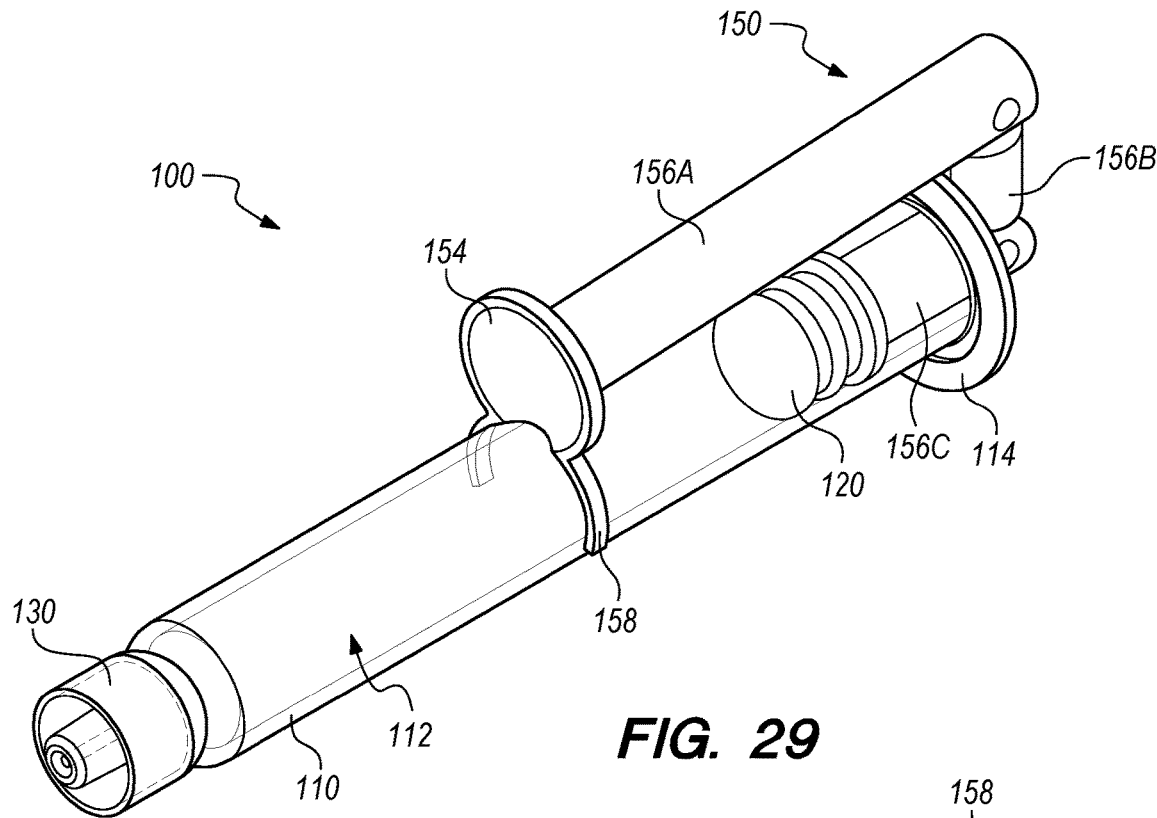

FIGS. 25, 27, and 29 depict the low-profile storage injection system 100 in its shipping/storage configuration, which is also called the "folded configuration." In the folded configuration, the proximal segment 156A of the plunger member 150 is folded back over the distal segment 156C of the plunger member 150 and approximately half (proximal) of the syringe body 110. The proximal segments 156A is folded around a double hinge formed by the middle segment 156B of the plunger member 150 and its connections with the proximal and distal segments 156A, 156C. The distal segment 156C is coupled to the stopper member 120 using a standard screw fit mechanism. In the folded configuration, the proximal thumb pad 154 also includes a latching member 158, which removably couples the proximal thumb pad 154 to the syringe body 110 with the interference fit.

Figure 26:
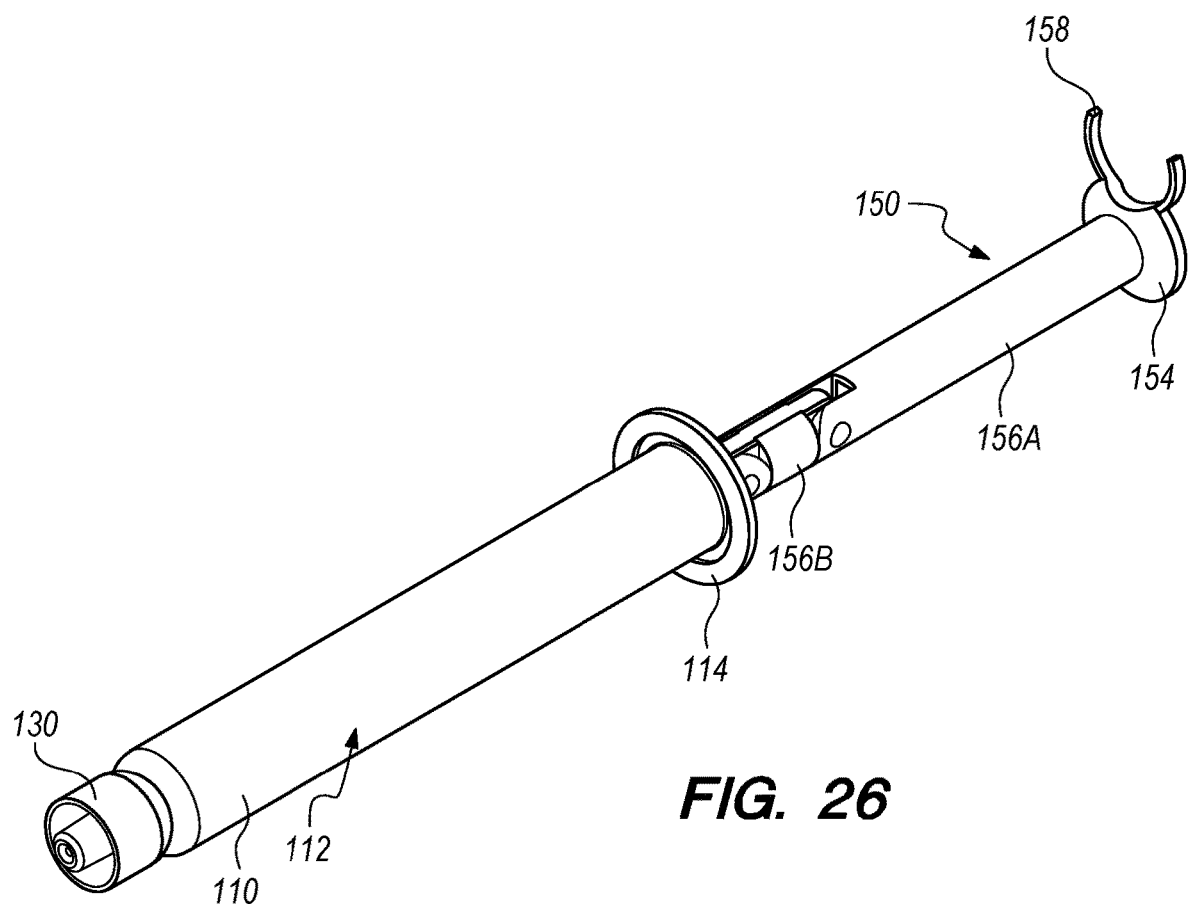
Figure 30:
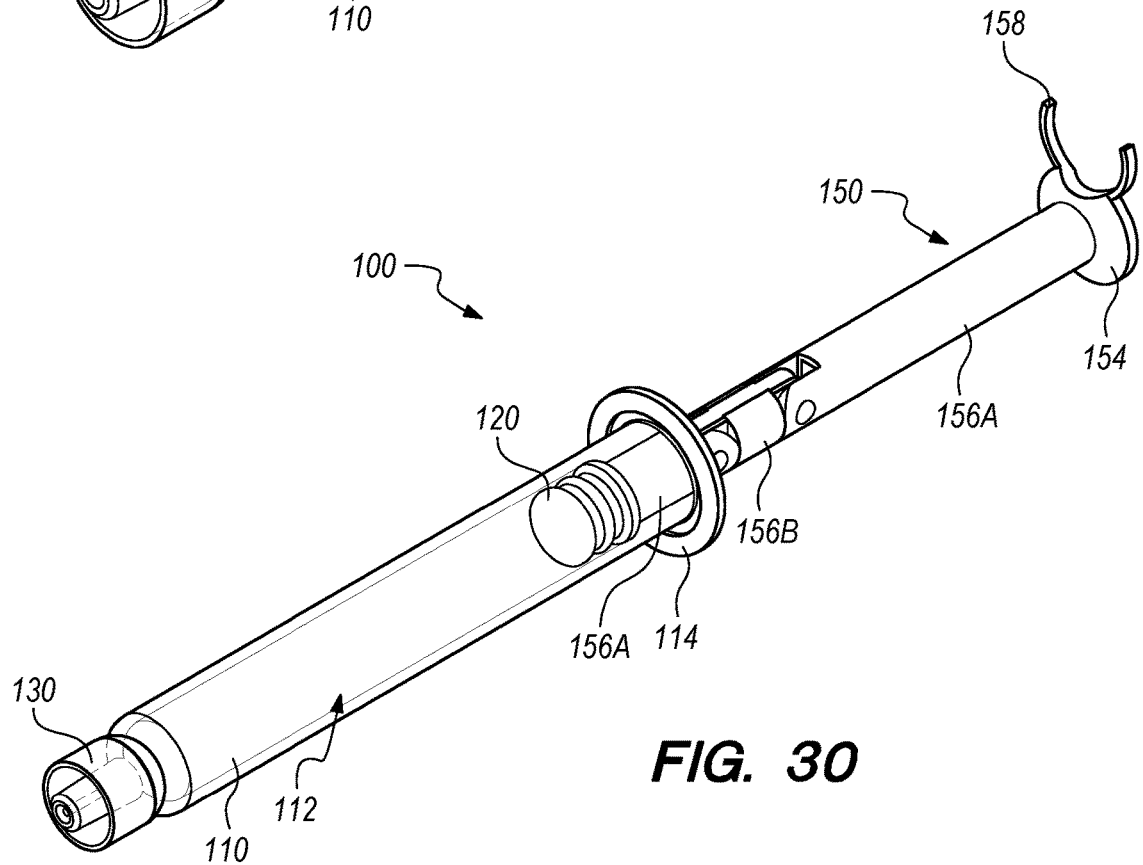
Figure 31:
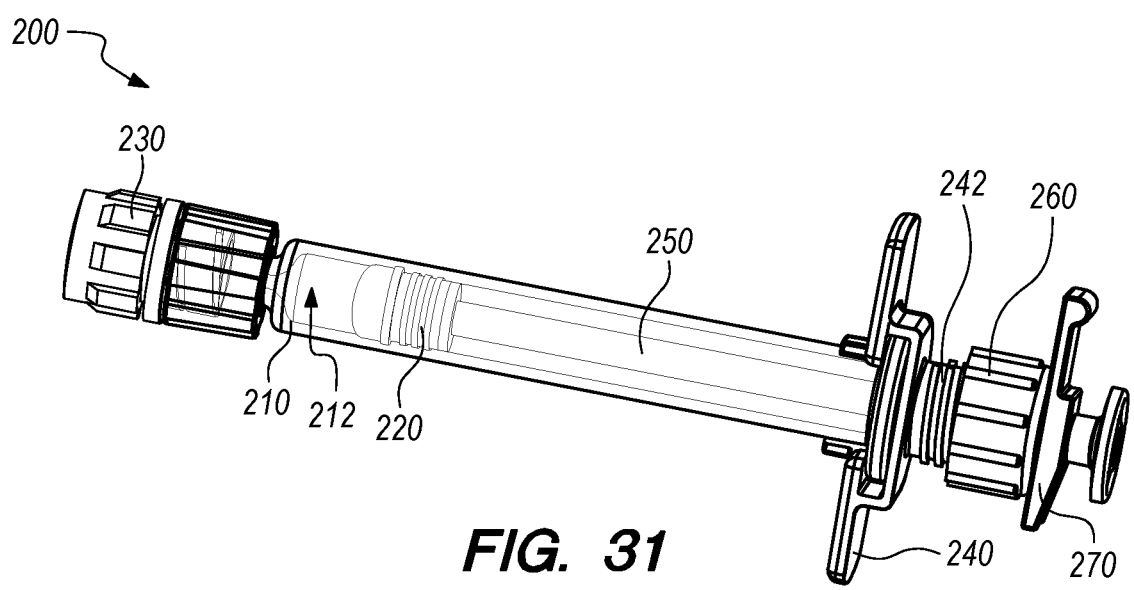
FIGS. 31-35 illustrate various aspects of a microdose injection system according to one embodiment.
Figure 32:
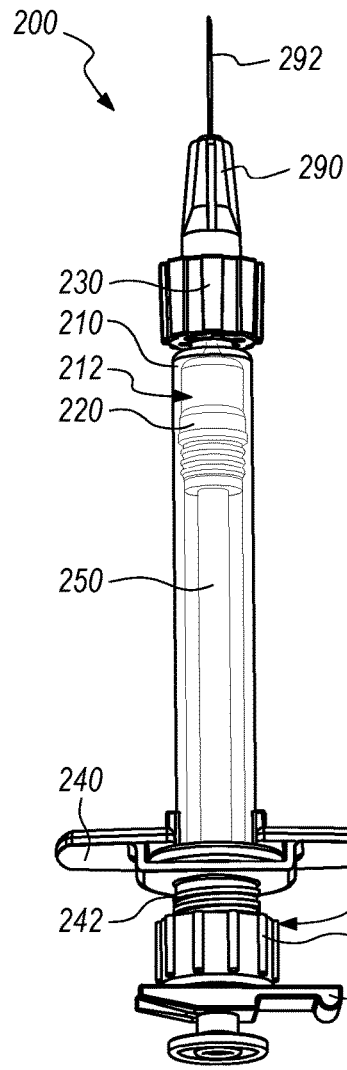
Figure 33:
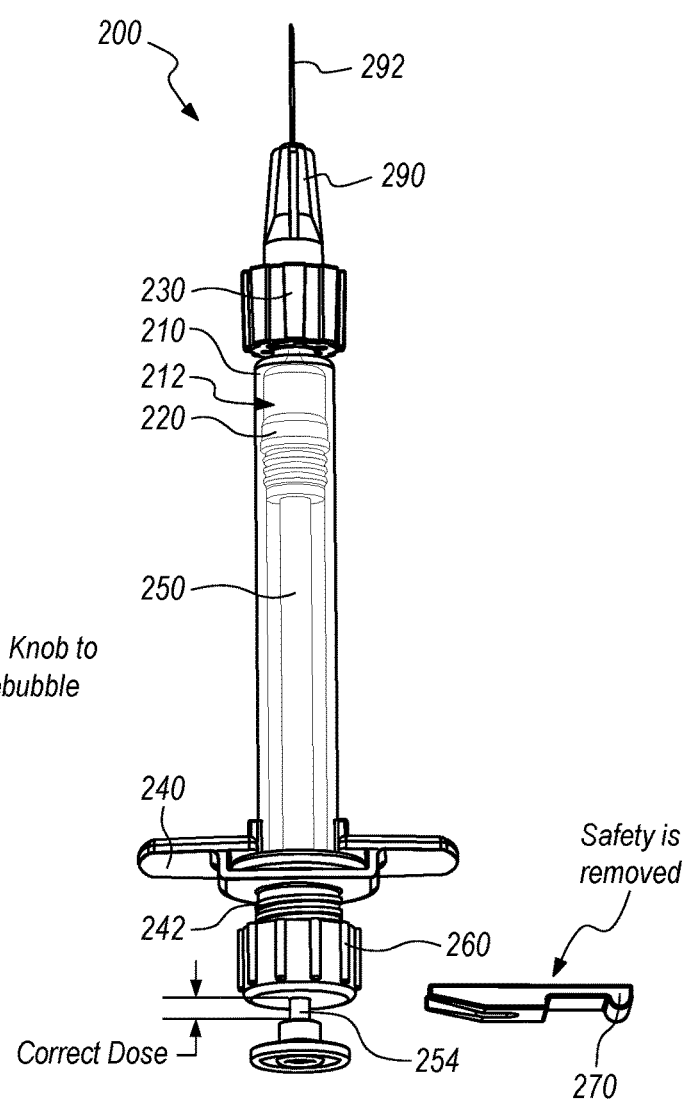

As shown in FIG. 27, the plunger member 150 can also include a spring 151, which is biased in a "straight configuration" to move the plunger member 150 into a straight configuration, as shown in FIGS. 26, 28, and 30. Alternatively, the plunger member 150 can be formed without a spring, and the folded plunger member 150 can be manually extended to the straight configuration.

Microdose Injection Systems

FIGS. 31-35 depict a microdose injection system 200 according to one embodiment. As used herein, the term "microdose" or "micro-dose" includes, but is not limited to, injections in the 1-1,000 microliter range. The microdose injection system 200 addresses the problem of injections in the microliter (e.g., 50 µL) volume range, which are difficult to accomplish with a standard injection system while maintaining precision (e.g., repeatability) and accuracy (e.g., proximity to desired volume). The microdose injection system 200 utilizes a rotatable microdose adapter/rotatable member 260 and a fixed plunger member travel distance/gap to perform microdose injections.

Figure 34:
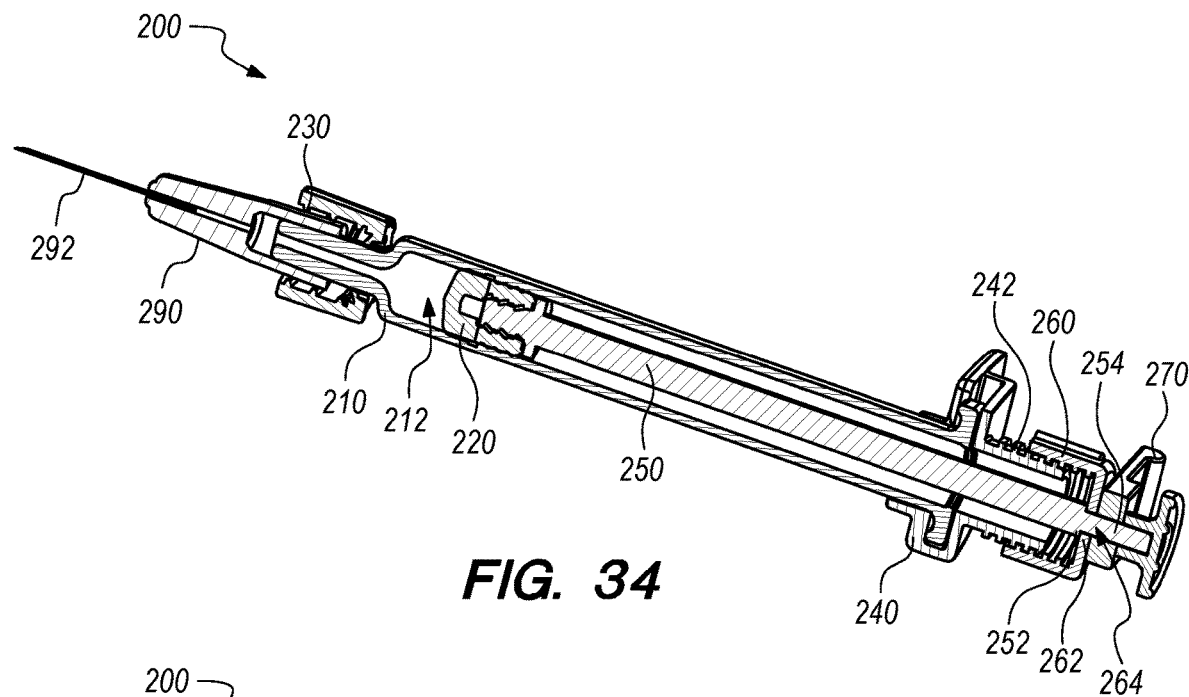
Figure 35:
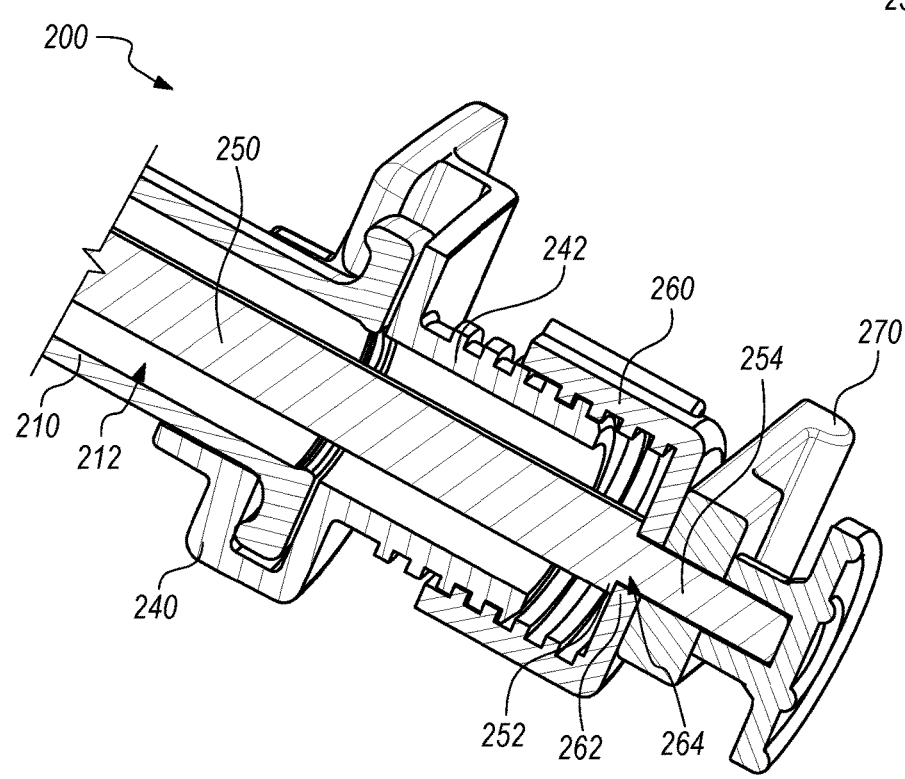

Like many of the injection systems described in co-owned U.S. patent application Ser. Nos. 62/521,252, 62/639,614, 14/696,342, 14/543,787, 14/321,706, 62/416,102, 62/431,382, 62/480,276, 62/508,508, 62/542,230, 15/801,239, 15/801,259, 15/801,281, 15/801,304, the contents of which were previously fully incorporated herein by reference as though set forth in full, the microdose injection system 200 utilizes off-the-shelf syringe bodies 210, stopper members 220, and connection members 230. Further, the microdose injection systems 200, 300, 400 described herein may use off-the-shelf needles assemblies 290, 390, 490 including needles 292, 392, 492. The finger flange 240 in the microdose injection system 200 includes a male threaded proximal section 242 configured to mate with a microdose adapter/rotatable member 260 having corresponding female threads, as shown in FIGS. 34 and 35.

The microdose adapter/rotatable member 260 includes a flange 262 configured to exert a small distal force on the shoulder/internal stop 252 formed on the plunger member 250 when the microdose adapter/rotatable member 260 is rotated clockwise onto the male threaded proximal section 242 of the finger flange 240. Rotating the microdose adapter/rotatable member 260 with the microdose injection system 200 in a vertical orientation can remove bubbles ("de-bubble" or "de-gassing") from an injectable substance in the syringe interior 212 and/or an interior of the needle assembly 290/needle 292.

Further, the plunger member 250 includes a narrow portion 254 configured to pass through an opening 264 in the microdose adapter/rotatable member 260, which is surrounded by/expands to form the shoulder/internal stop 252. The length of the narrow portion 254 can be modified to control the injection volume and travel distance/gap.

The microdose injection system 200 also includes a safety member 270 configured to couple to the narrow portion 254 of the plunger member 250 and prevent distal movement of the plunger member 250 relative to the microdose adapter/rotatable member 260. As shown in FIG. 8, after the safety member 270 is removed, the plunger member 250 can be moved distally, but only a length equal to a length of the narrow portion 254 outside of the microdose adapter/rotatable member 260, which is equal to the travel distance/gap. Therefore, the injection volume is controlled by this length of the narrow portion 254. The microdose injection system 200 can therefore give precise and accurate injections with a precision de-bubbling mechanism.

FIGS. 36-50 depict a microdose injection system 300 according to another embodiment. Like the microdose injection system 300 depicted in FIGS. 31-35, the microdose injection system 300 includes a syringe body 310, a stopper member 320, a connection member 330, a finger flange 340, a plunger member 350, a needle assembly 390, and a microdose adapter/rotatable member 360. In fact, many of these system components (e.g., syringe body 310, the stopper member 320, and the connection member 330) may be off-the-shelf components to utilize the existing and relatively well-controlled supply chain, and the corresponding assembly machinery and personnel. The syringe body 310 may be an off-the-shelf 0.50 cc syringe body 310 to improve the accuracy of the microdose injection system 300. The needle assembly 390*may be a commercially available, off-the-shelf needle assembly with a needle 392 (e.g., 20-34 gauge and length 6 mm-⅝"; in particular 32 gauge×6 mm length). The needle assembly 390 may utilize Luer lock or Luer slip configurations to attach the needle assembly 390 to the syringe body 310/connection member 330. In some embodiments, microdose injection systems 300 can achieve error rates of less than ±10 µL.

One difference between the microdose injection system 300 depicted in FIGS. 31-35 and the microdose injection system 300 depicted in FIGS. 36-50 is that the latter includes a plunger cap 370 (e.g., instead of a safety member 370). The plunger cap 370 serves a similar function to the safety member 370 in that it is configured to prevent premature injection by preventing distal movement of the plunger member 350, while allowing the microdose adapter/rotatable member 360 to rotate to the de-bubble the microdose injection system 300.

Figure 38:
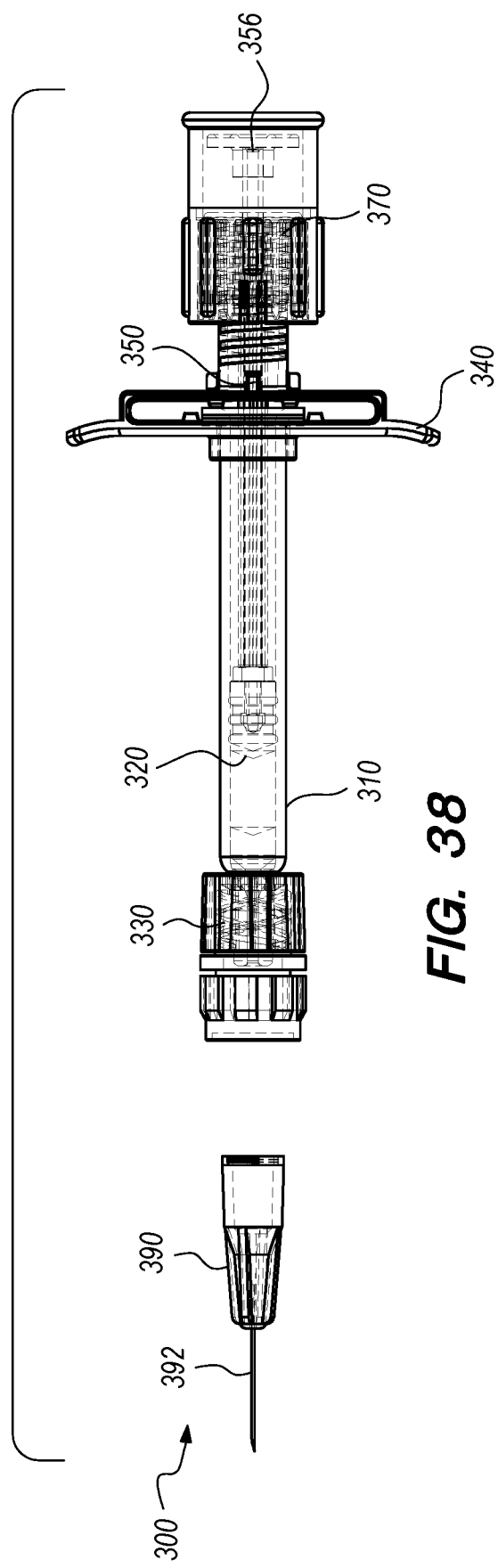

FIGS. 36-50 depict an injection process using the microdose injection system 300. FIGS. 36-38 depict the microdose injection system 300 before it is coupled to a needle using the connection member 330. In this state, the connection member 330 is capped by a connection member cover.

Figure 39:
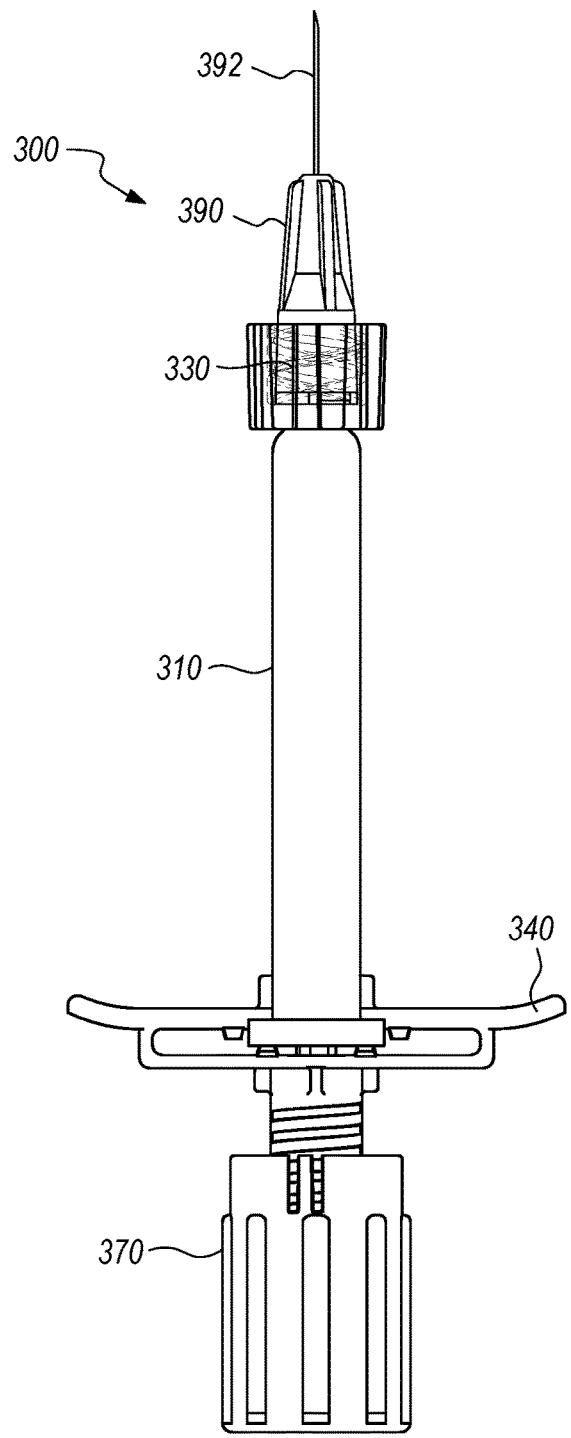
Figure 40:
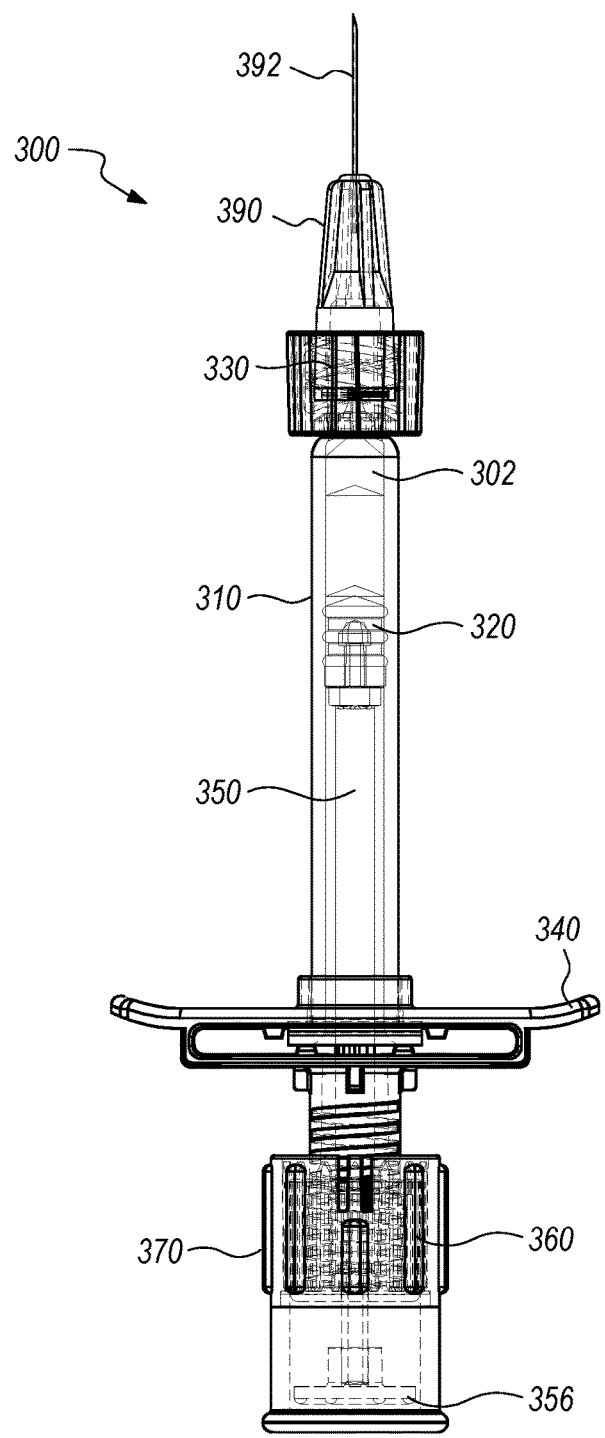
Figure 41:
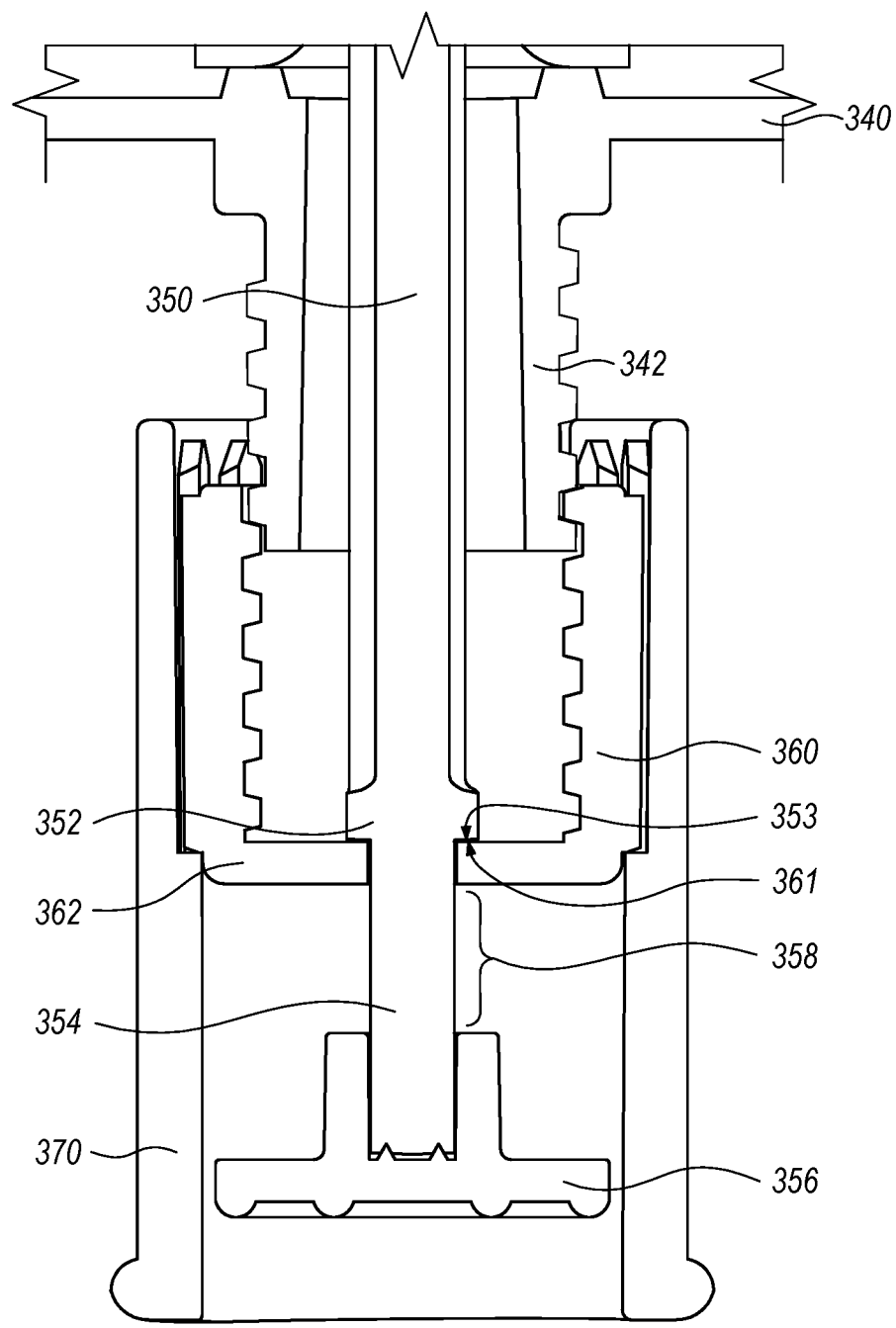

FIGS. 39-41 depict the microdose injection system 300 after the needle has been coupled to the microdose injection system 300 using the connection member 330. In this embodiment, the connection member 330 is a female Luer connector, and the corresponding connection member on the needle is a male Luer connector, resulting in a Luer lock connection, as shown in FIG. 40.

FIGS. 39-41 depict the microdose injection system 300 in a vertical position, wherein the needle is pointed generally upward. This causes any gas/air in the syringe body 310 to move to the top of the syringe body 310 as shown by the gas/air bubble 302 in FIG. 40. In this position, distal movement of the stopper member 320 will eject the gas/air bubble 302 from the syringe body 310 and/or eject air from an interior of the needle assembly 390/needle 392, thereby preparing the microdose injection system 300 for injection.

FIG. 41 depicts in detail the relative positions of the microdose adapter/rotatable member 360, the male threaded proximal section 342 of the finger flange 340, and the plunger cap 370 one the microdose injection system 300 is in the vertical, or "de-bubbling," position. The threads on the male threaded proximal section 342 of the finger flange 340 have been omitted for clarity.

Figure 44:
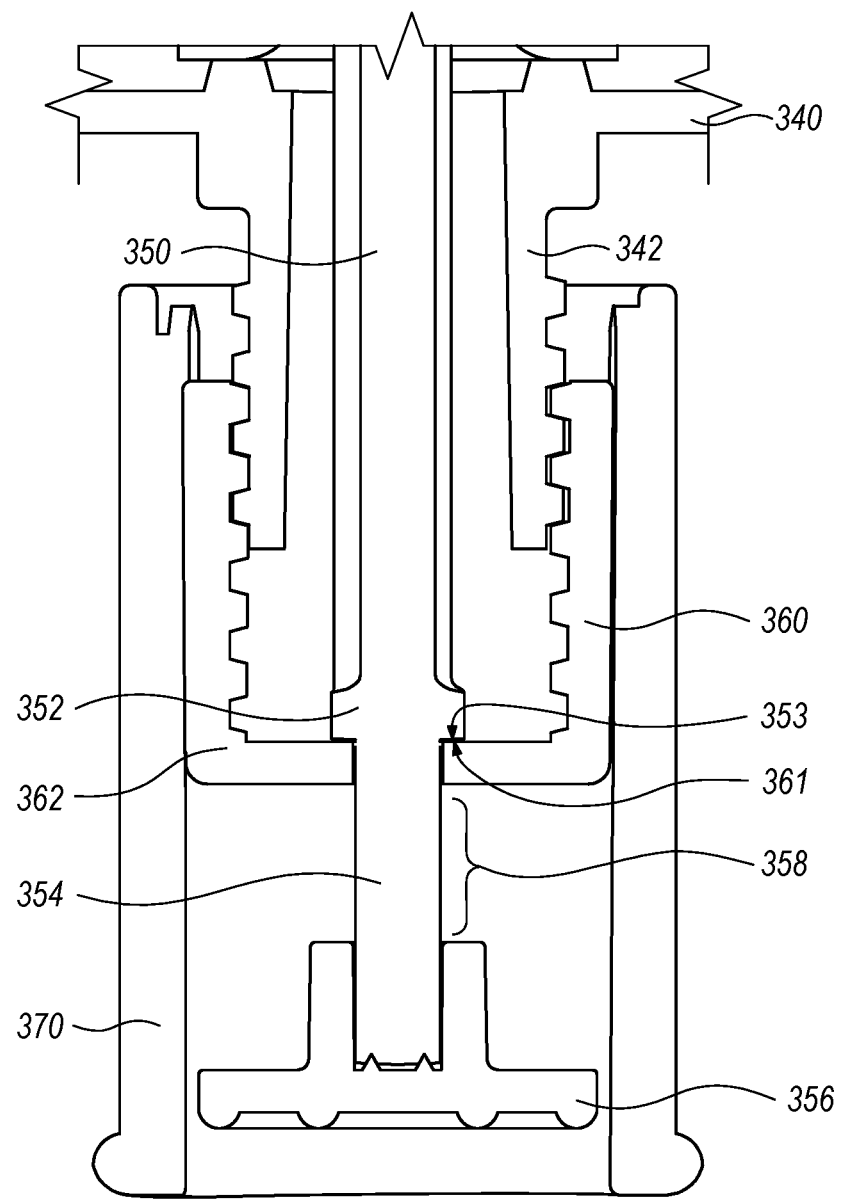

FIGS. 42-44 depict the microdose injection system 300 after the microdose injection system 300 has been de-bubbled. The de-bubbling process involves rotation of the microdose adapter/rotatable member 360 (e.g., in a clockwise position for normal threaded parts) direction with the microdose injection system 300 in the vertical de-bubbling position.

Figure 57:
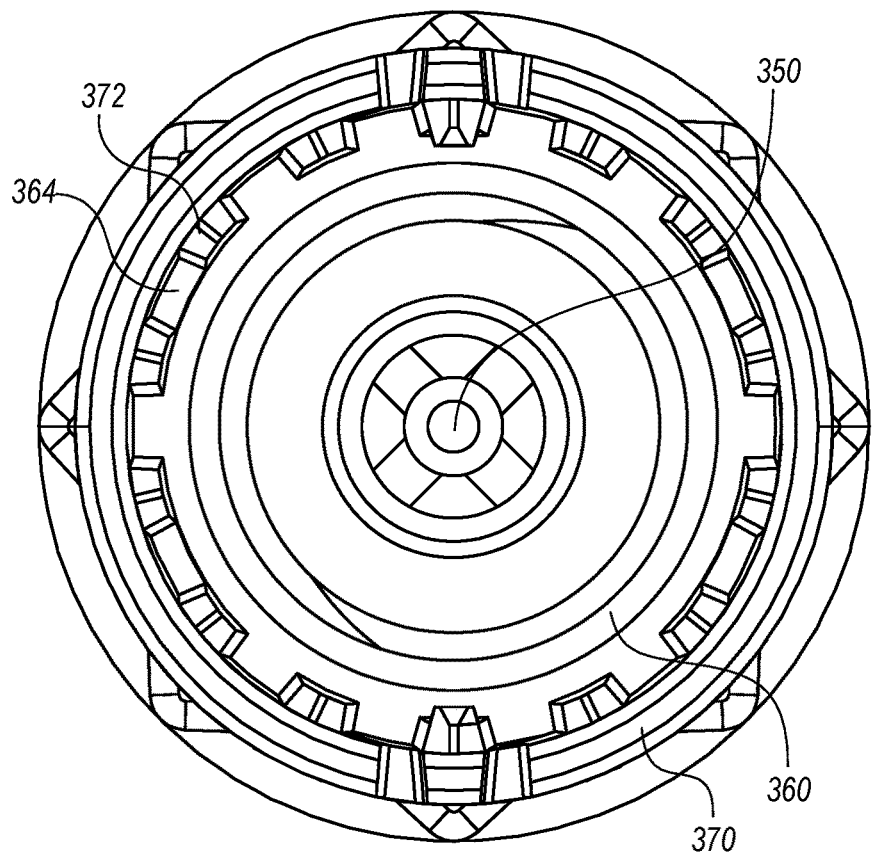
Figure 58:
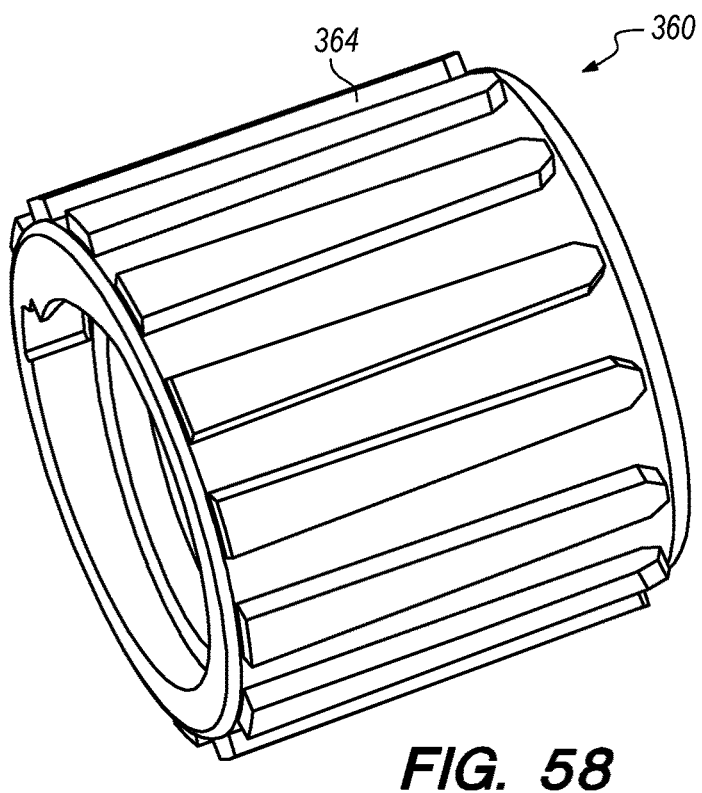
Figure 59:
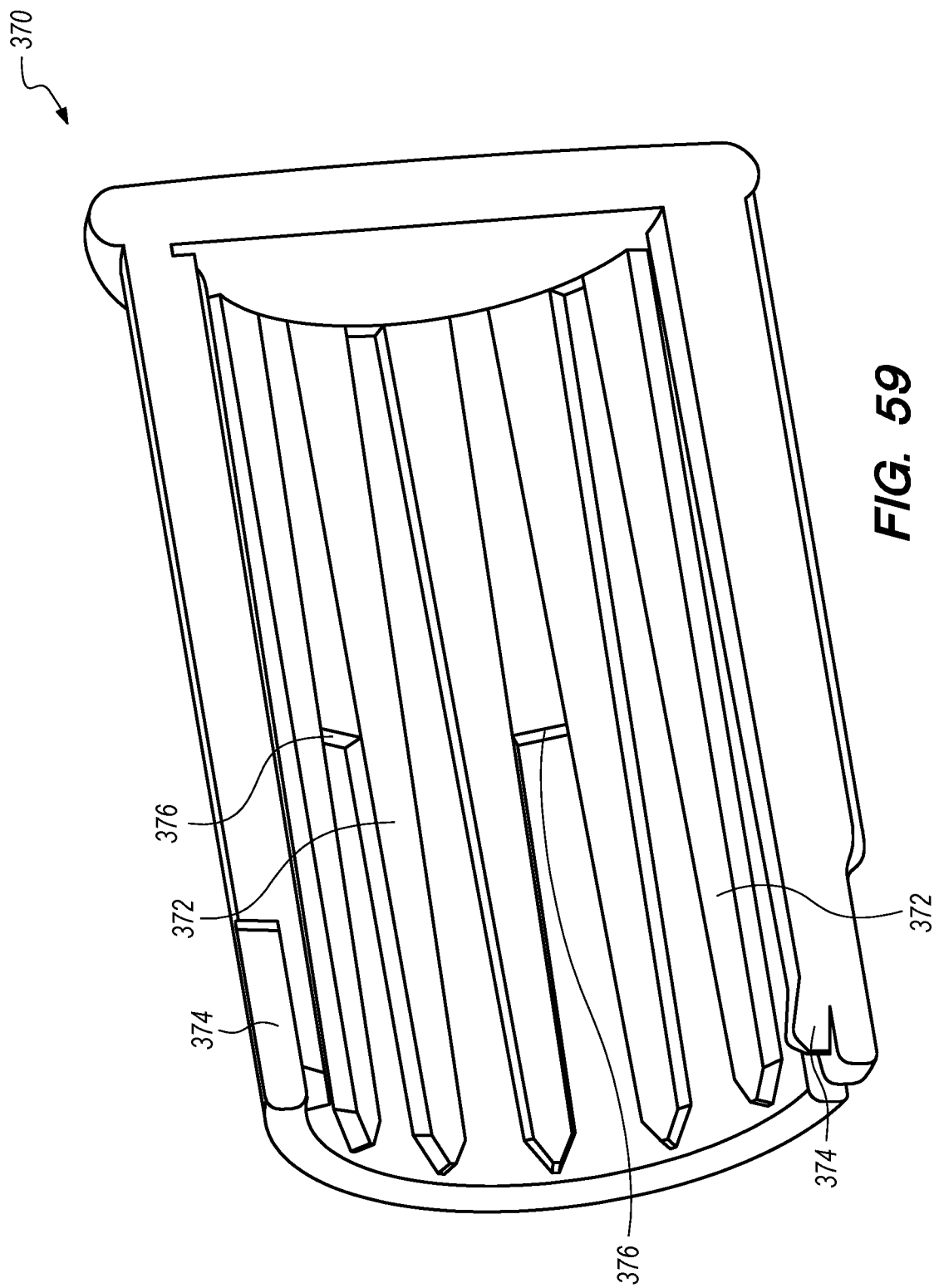

The plunger cap 370 has a plurality of internally directed splines 372 and the microdose adapter/rotatable member 360 has a corresponding plurality of externally directed splines 364, as shown in FIGS. 59 and 58, respectively. The respective pluralities of internally and externally splines (372, 364) are configured such that when the plunger cap 370 is removably coupled to the plunger microdose adapter/rotatable member 360, rotation of the plunger cap 370 causes corresponding rotation of the microdose adapter/rotatable member 360, as shown in FIGS. 56 and 57.

Rotation of the microdose adapter/rotatable member 360 moves the microdose adapter/rotatable member 360 distally on the male threaded proximal section 342 of the finger flange 340, thereby advancing the plunger member 350 and the stopper member 320 coupled thereto distally in an interior of the syringe body 310. Moving the microdose adapter/rotatable member 360 distally relative to the syringe body 310 causes a distally facing surface 361 on the adapter 360 to exert a distally directed force on a proximally facing surface 353 on a shoulder/internal stop 352 coupled to or formed on a proximal end of the plunger member 350, as shown in FIG. 44. The distally directed force is proportional to the amount of rotation of the microdose adapter/rotatable member 360 and is delivered to the stopper member 320 through the plunger member 350.

The distally directed force moves the stopper member 320 distally in the interior of the syringe body 310. Because the microdose injection system 300 is in the vertical de-bubbling position, distal movement of the stopper member 320 in the interior of the syringe body 310 ejects the gas/air bubble (see 302 in FIG. 40) from the interior of the syringe body 310 and/or eject air from an interior of the needle assembly 390/needle 392, thereby de-bubbling the microdose injection system 300.

Figure 56:
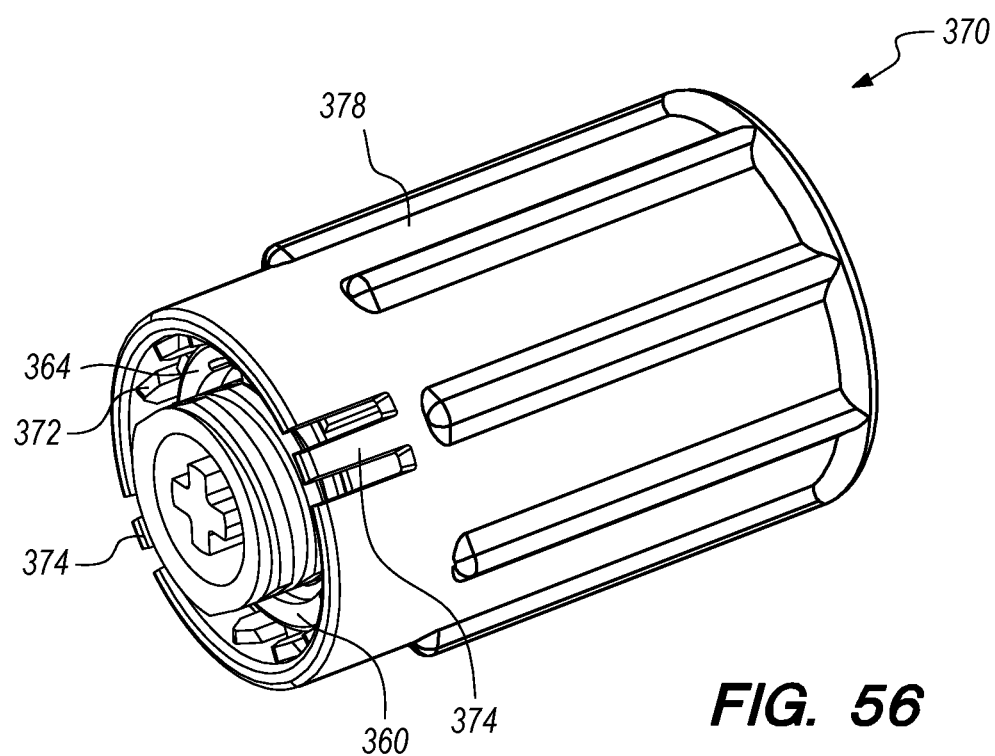

As shown in FIGS. 56 and 59, the plunger cap 370 includes a retention feature 374 configured to removably couple the plunger cap 370 to the microdose adapter/rotatable member 360. The retention member 374 includes a pair of the elastically deformable arms with hooks on the ends thereof to inhibited proximal movement of the plunger cap 370 relative to the microdose adapter/rotatable member 360 when the former is removably coupled to the latter. The elastically deformable arms are disposed on opposite sides along the circumference of the distal end of the plunger cap 370. The hooks on the elastically deformable arms wrap around the distal end of the microdose adapter/rotatable member 360, and their elasticity prevents the plunger cap 370 from moving proximally relative to the microdose adapter/rotatable member 360 until sufficient proximally directed force (e.g., 0.5 lbs.) is applied to the plunger cap 370 to overcome the elasticity of the retention members 374.

As shown in FIG. 59, the plunger cap 370 also includes a plurality of spline stops 376 configured to interfere with some (e.g., two) of the plurality of externally directed splines 364 on the microdose adapter/rotatable member 360 to prevent proximal movement of the plunger cap 370 relative to the microdose adapter/rotatable member 360. This in turn prevents distal movement of the thumb pad/external stop 356 relative to the syringe body 310 and premature injection before the plunger cap 370 is removed from the microdose adapter/rotatable member 360.

As shown in FIG. 56, the plunger cap 370 also has a knurled outer surface 378 to facilitate manual or automated rotation of the plunger cap 370.

Figure 47:
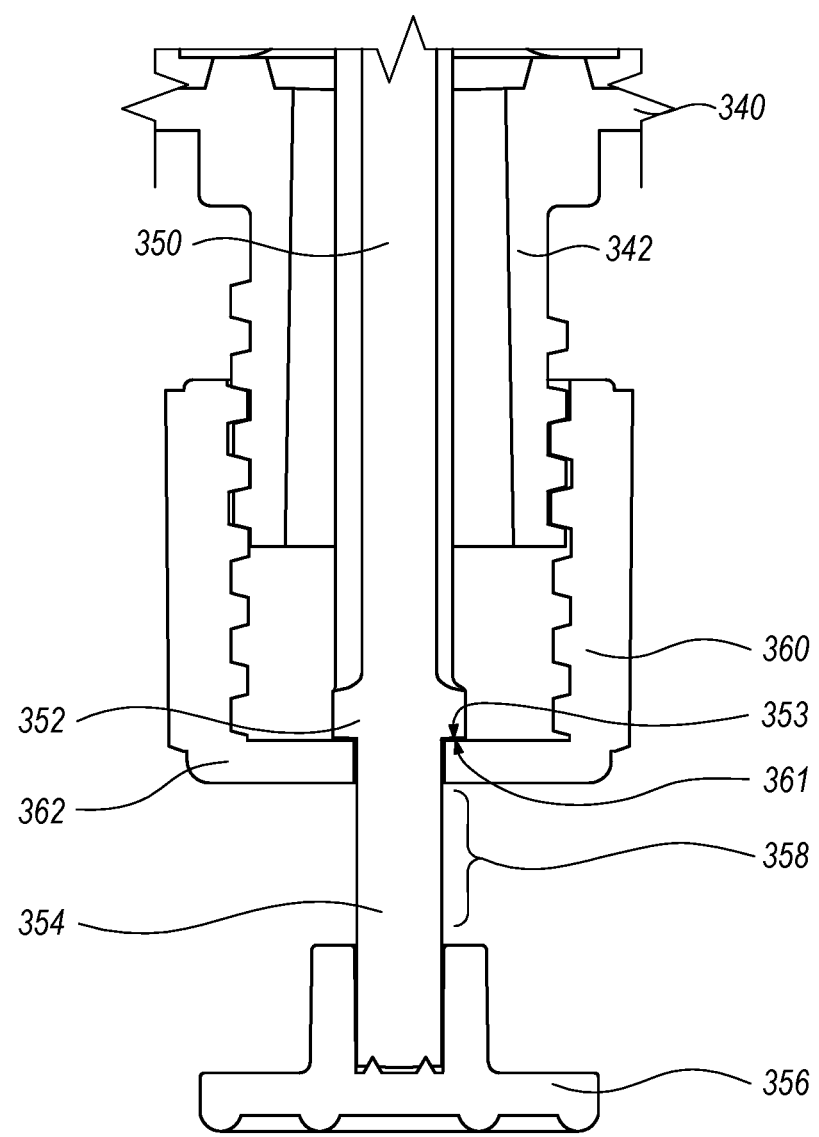

FIGS. 45-47 depict the next step in the injection process, which is removal of the plunger cap 370. By applying sufficient proximally directed force to the plunger cap 370, the elasticity of the retention members 374 (see FIG. 56) is overcome, and the plunger cap 370 can be moved proximally from the microdose adapter/rotatable member 360. Removal of the plunger cap 370 allows distal movement of the thumb pad/external stop 356 and the plunger member 350, thereby placing the microdose injection system 300 in a ready for injection state.

As shown in FIG. 47, the microdose adapter/rotatable member 360 includes a proximal flange 362. A narrow portion 354 of the plunger member 350 defines a gap 358 between a proximally facing surface of the proximal flange 362 and a distally facing surface of the thumb pad/external stop 356. The size of the gap 358 can be modified by modifying the plunger member 350 and/or the thumb pad/external stop 356. The size/axial length of the gap 358 determines the amount of axial movement of the stopper member 320 in the interior of the syringe body 310, and therefore the amount of fluid (e.g., medicine) injected by the microdose injection system 300.

Still referring to FIG. 47, the plunger member 350 also includes a shoulder/internal stop 352. The shoulder/internal stop 352 and the thumb pad/external stop 356 our sized such that neither of them can pass through the opening in the microdose adapter/rotatable member 360. Accordingly, the relative positions of the shoulder/internal stop 352 and the thumb pad/external stop 356 define the maximum travel of the plunger member 350 relative to the microdose adapter/rotatable member 360. This maximum travel of the plunger member 350 also corresponds to the size/axial length of the 358. The shoulder/internal stop 352 also prevents removal of the plunger member 350 from the microdose adapter/rotatable member 360.

Figure 50:
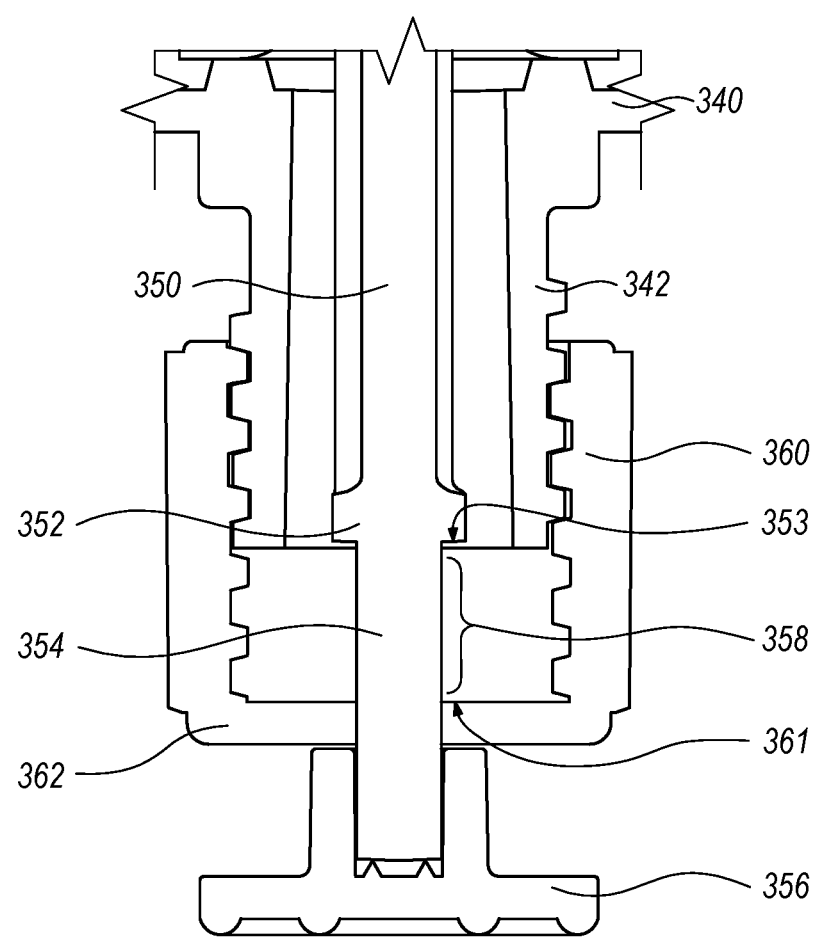

FIGS. 48-50 depict the next step in the injection process, which is giving the microdose injection. The distally directed force is applied to the thumb pad/external stop 356, thereby advancing the plunger member 350 and the stopper member 320 coupled thereto distally in an interior of the syringe body 310. The distally directed force can be applied manually by a user or automatically by an auto injector.

Comparing FIGS. 47 to 50 shows that application of the distally directed force to the thumb pad/external stop 356 collapses the gap 358 outside of the microdose adapter/rotatable member 360. This also moves the shoulder/internal stop 352 distally away from the distal facing surface 361 of the microdose adapter/rotatable member 360. In fact, and internal gap 358' is now formed inside of the microdose adapter/rotatable member 360. This internal gap 358' is the same size/axial length as the original gap 358 outside of the microdose adapter/rotatable member 360.

Comparing FIGS. 46 and 49 shows that distal movement of the stopper member 320 an interior of the syringe body 310 has ejected some fluid from the interior of the syringe body 310, resulting in an injection of a predetermined amount of fluid. In microdose applications, this predetermined amount of fluid can be from about 5 µL to about 250 µL. In one particular embodiment, this predetermined amount of fluid is about 50 µL.

Microdose Injection/Withdrawal Systems and Methods

In some embodiments, the microdose injection process does not stop with the injection (i.e., of a first volume of fluid/medicine). In such embodiments, the injection process includes one more step—the withdrawal of some fluid (i.e., of a second volume of fluid) from the injection site.

One clinical scenario were such a microdose injection/withdrawal system embodiment may be useful is intraocular injections in patients with elevated eye pressure. Such patients would benefit from intraocular injections of medicine, but the increased intraocular volume may exacerbate the elevated eye pressure and cause tissue (e.g., nerve) damage to the sensitive organ. Further, if the first volume injected and the second volume withdrawn are significantly dissimilar, other problems may arise. For instance, if the second volume withdrawn is significantly larger than the first volume injected, the eyeing me deform causing vision changes, or even collapse in extreme cases.

The microdose injection system 300 described above addresses these clinical issues by defining a gap 358 between the shoulder internal stop 352 and the thumb pad/external stop 356. Because the gap 358 controls the amount of fluid injected into a patient and withdrawn from a patient, the microdose injection system 300 allows for injection and withdrawal of substantially similar volumes.

For instance, after injecting a first fluid as depicted in FIGS. 48-50, the microdose injection system 300 can be returned to the state depicted in FIGS. 45-47 by applying a proximally directed force on a distally directed surface of the thumb pad/external stop 356. This proximally directed force would pull the plunger member 350 and the stopper member 320 attached thereto proximally in the interior of the syringe body 310, thereby withdrawing a second fluid from the patient. A period of time can be allowed to pass between injecting the first fluid and withdrawn the second fluid to allow the medicine in the first fluid to diffuse through the second fluid. Because the shoulder internal stop 352 and the thumb pad/external stop 356 limit the travel of the plunger member 350 to approximately the length of the gap 358, the distal travel of the plunger member 350 during injection is substantially the same as the proximal travel of the plunger member 350 during withdrawal.

Microdose Injection Systems Details

Figure 51:
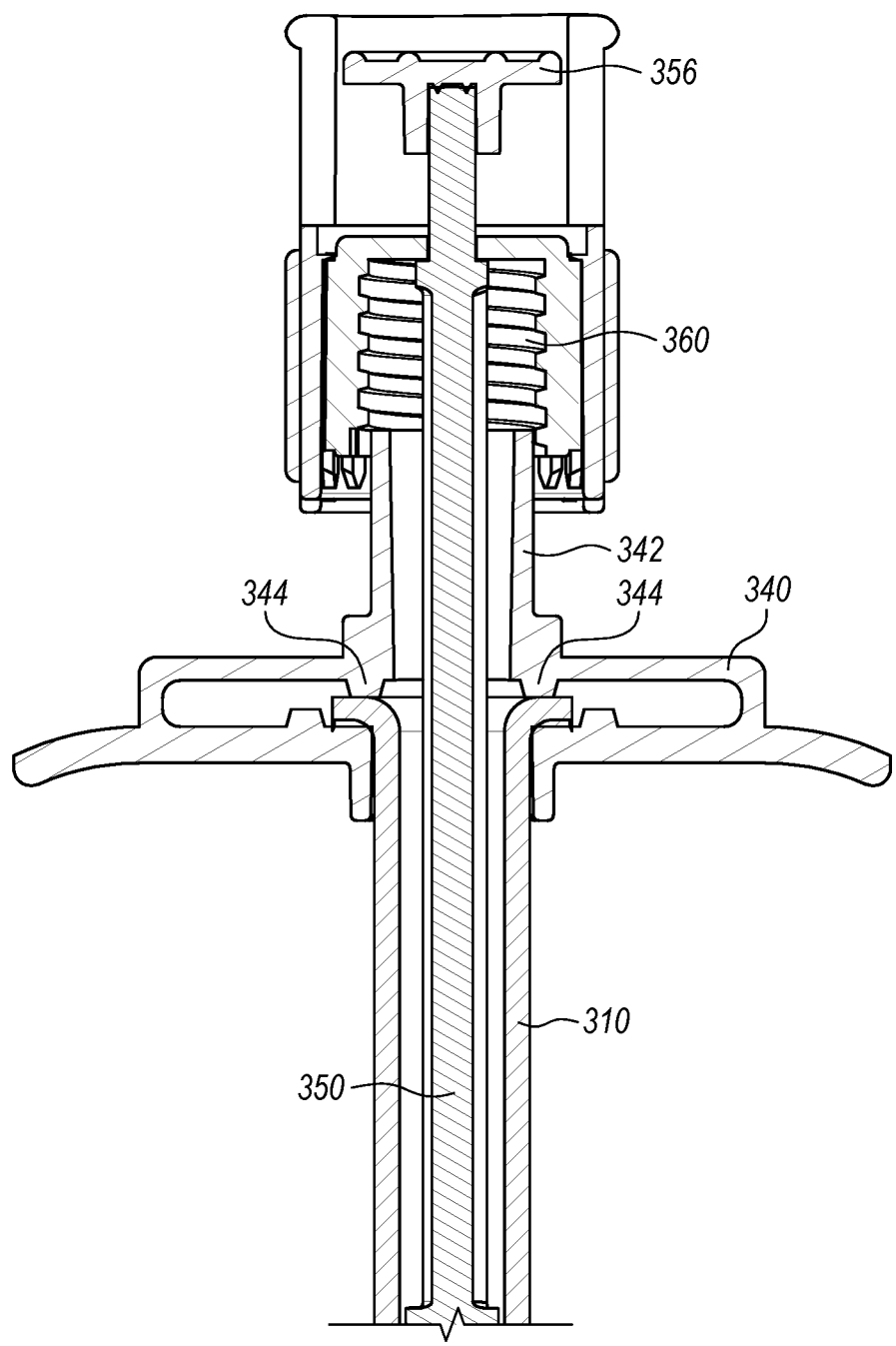
FIGS. 51-59 illustrate various detailed aspects of a microdose injection system according to one embodiment.
Figure 52:
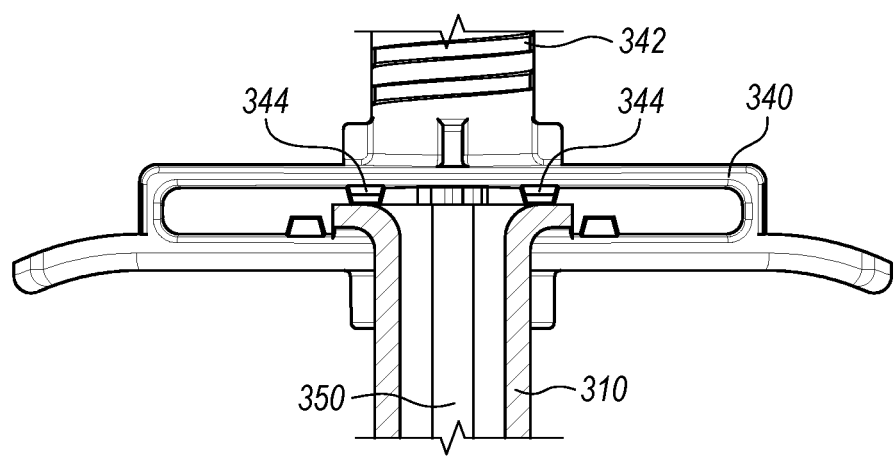

FIGS. 51 and 52 depict the finger flange 340 removably coupled to a syringe flange 312 of the syringe body 310. As shown in FIG. 52, the finger flange 340 includes a pair of internal surface projections/beams 344 projecting from a distally facing internal surface of the finger flange 340. The internal surface projections/beams 344 are configured to engage and form an interference fit with a proximally facing surface of the syringe flange 312. The finger flange 340 is formed of an elastically deformable material (e.g., a polymer), such that the finger flange 340 can elastically deformed to accommodate a range of thicknesses, geometries, etc. of the syringe flange 312. Within a range of thicknesses of the syringe flange 312, the finger flange 340 and its internal surface projections/beams 344 will form an interference fit with the syringe flange 312, thereby removably coupling the finger flange 340 to the syringe flange 312 and the syringe body 310.

The elasticity of the finger flange 340 facilitates a tight and secure interference fit between the finger flange 340 and a wide variety of syringe flange 312 thicknesses and geometries. This improves the accuracy and precision/repeatability of dosage delivery because the finger flange 340, including the male threaded portion 342 thereof, will be pressed tightly against the syringe flange 312, leaving no clearance between the finger flange 340 and the syringe flange 312. A tight interference fit improves accuracy and precision because any clearance may be added to the travel distance of the plunger member 350 in addition to the gap 358, thereby introducing an error in the volume of fluid/medicine delivered during the microdose injection.

However, minimizing the clearance between the finger flange 340 and the syringe flange 312 is complicated because the syringe flange 312 thickness has a sizable range (e.g., depending on the manufacturer, the batch, etc.) If the finger flange 340 simply had a non-deformable slot to accommodate the syringe flange 312, this slot must be large enough to accommodate the largest possible syringe flange 312. When a thinner syringe flange 312 is inserted into the slot, there would be a clearance that would increase the microdose volume resulting in a dosage error.

According to one embodiment, the slot in the finger flange 340 for the syringe flange 312 is elastically deformable/flexible and sized for the thinnest syringe flange 312. Consequently, even when the thinnest syringe flange 312 is removably coupled to the finger flange 340, there will be no clearance between the finger flange 340 and the syringe flange 312, and the dosage will be accurate and precise.

When a syringe body 310 with an average or even a thicker than average syringe flange 312 is removably coupled to the finger flange 340, the slot in the elastically deformable/flexible finger flange 340 will expand to accommodate the thicker syringe flange 312 leaving no clearance. Therefore, the elastically deformable/flexible finger flange 340 improves microdose injection system 300 accuracy and precision.

Figure 53:
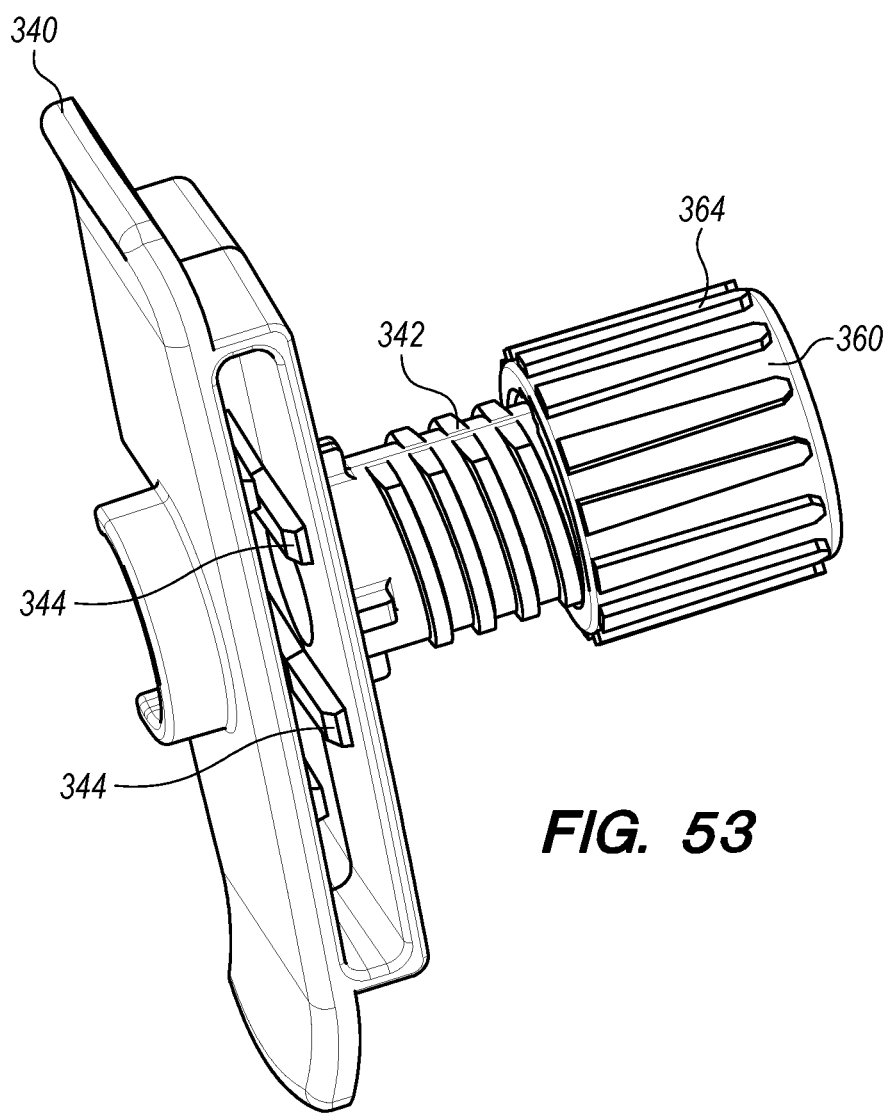
Figure 54:
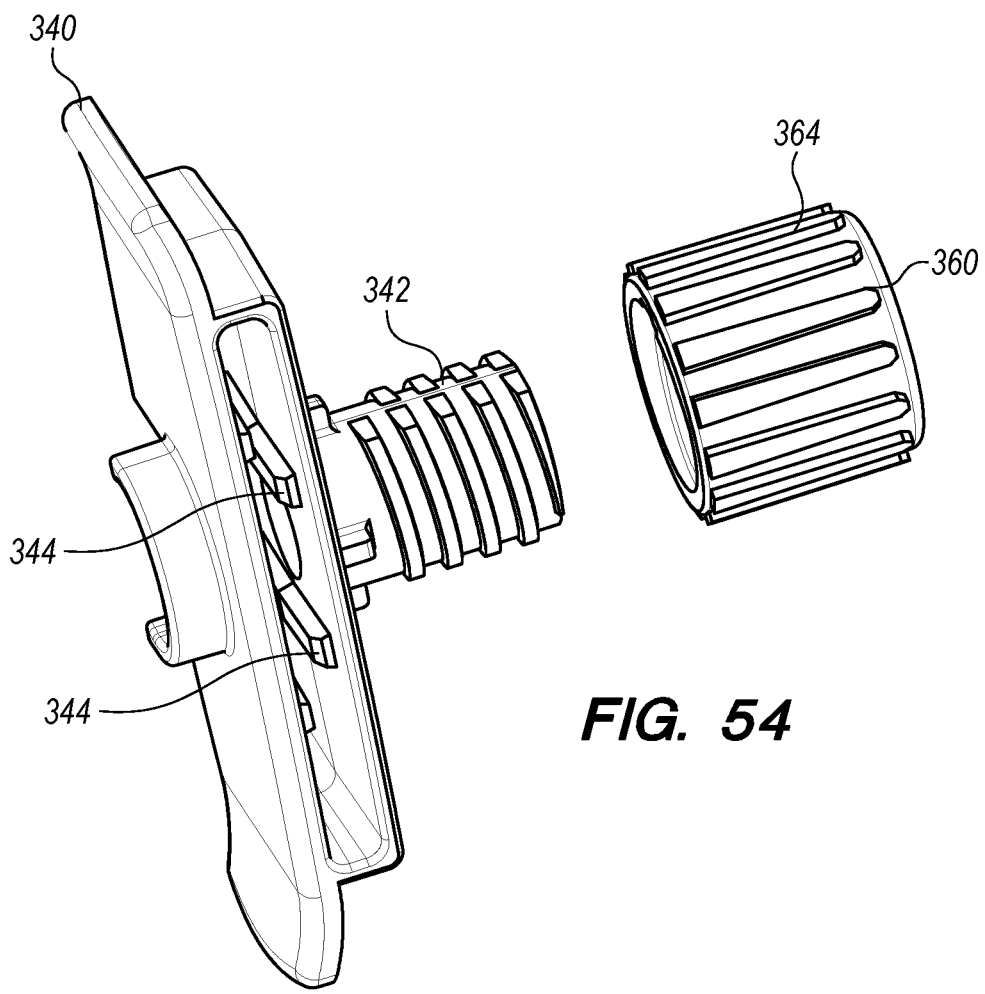

FIGS. 53 and 54 depict the male threaded proximal section 342 of the finger flange 340 and its interaction with the corresponding female threads on the inside surface of the microdose adapter/rotatable member 360. The male threads on the finger flange 340 and the female threads on the microdose adapter/rotatable member 360 are configured such that rotating microdose adapter/rotatable member 360 clockwise on the finger flange 340 moves the former distally on the latter. Using rotation along with a helical thread to generate axial movement allows finer control of the axial movement, which is useful during the de-bubbling process described above. In some embodiments, the finger flange 340 and/or the microdose adapter/rotatable member 360 may include a ratcheting mechanism to prevent backwards (e.g., counterclockwise) rotation of the microdose adapter/rotatable member 360 on the finger flange 340. This prevents the category of user error that can disable/damage a microdose injection system 300.

Figure 55:
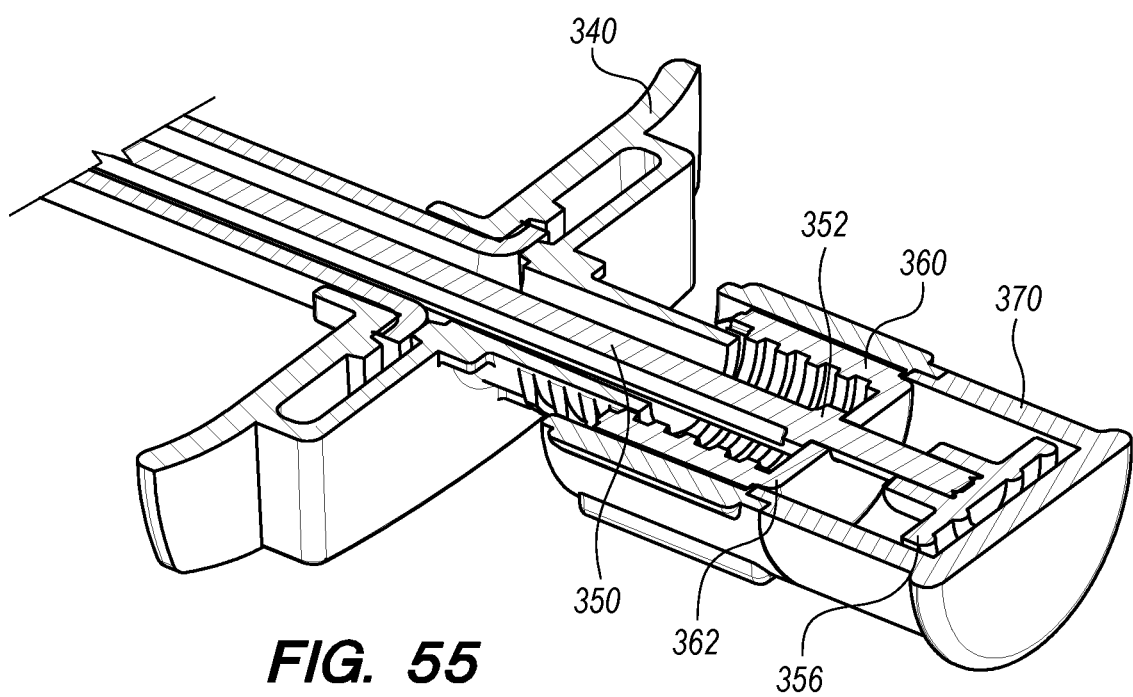

FIG. 55 depicts the interaction between the plunger cap 370 and the thumb pad/external stop 356 that couples distal movement of the microdose adapter/rotatable member 360 to distal movement of the plunger member 350 and the stopper member 320 coupled thereto.

FIGS. 56-59 depict the interaction between the plunger cap 370 and the microdose adapter/rotatable member 360, which has been described above. In brief, retention members 374 and splines stops 376 on the plunger cap 370 removably couple the plunger cap 370 to the microdose adapter/rotatable member 360 until a sufficiently large proximal forces applied to the plunger cap 370 to elastically deform the retention members 374. Also, the respective pluralities of internally and externally directed splines (372, 364) on the plunger cap 370 and the microdose adapter/rotatable member 360 rotationally couple the plunger cap 370 and the microdose adapter/rotatable member 360, as especially shown in FIG. 57.

Plunger Cap Embodiments

FIGS. 60-73 depict plunger caps 370 according to various embodiments. All of these plunger caps 370 prevent premature injection by preventing distal movement of the plunger member 350, while allowing the microdose adapter/rotatable member 360 to rotate to the de-bubble the microdose injection system 300. All of these plunger caps 370 also include a retention feature 374 configured to removably couple the plunger cap 370 to the microdose adapter/rotatable member 360. All of these plunger caps 370 further include a plurality of spline stops 376 configured to interfere with some (e.g., two) of the plurality of externally directed splines 364 on the microdose adapter/rotatable member 360 to prevent proximal movement of the plunger cap 370 relative to the microdose adapter/rotatable member 360. Moreover, all of these plunger caps 370 have respective knurled outer surfaces 378 to facilitate manual or automated rotation of the plunger caps 370.

Figure 60:
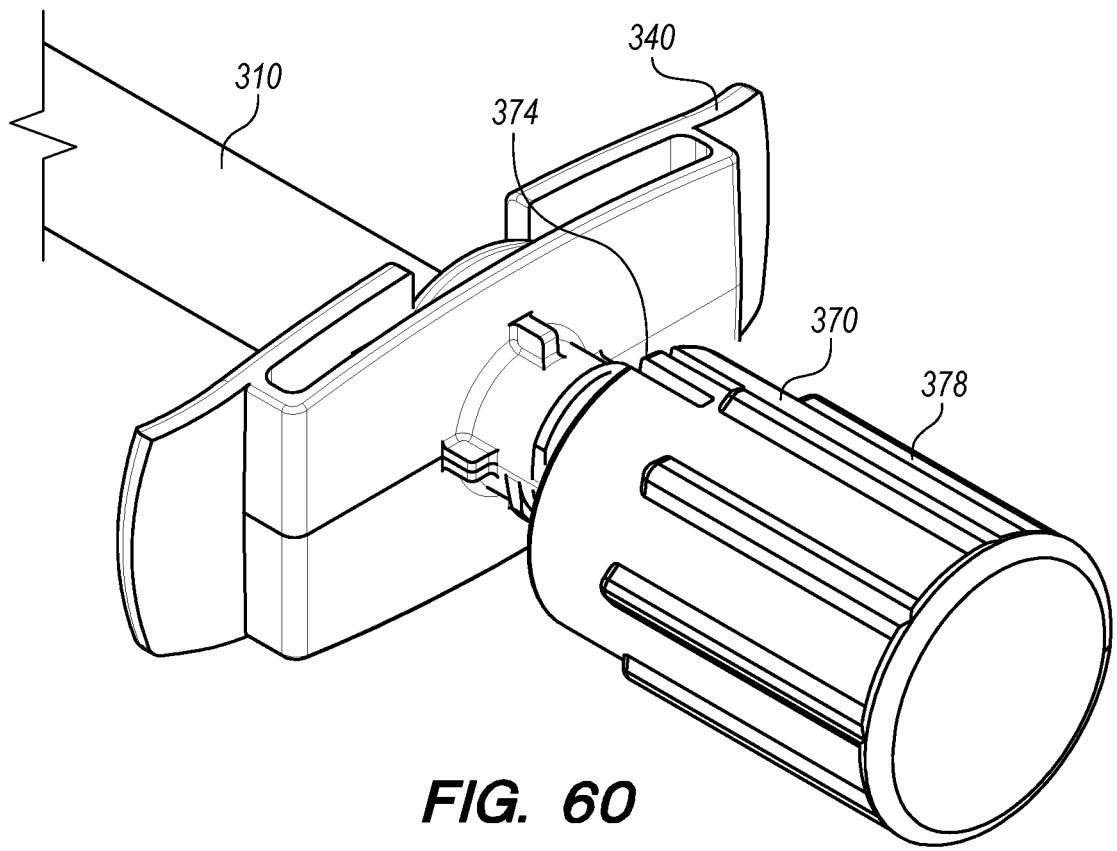
FIGS. 60-73 illustrate plunger caps according to various embodiments.
Figure 61:
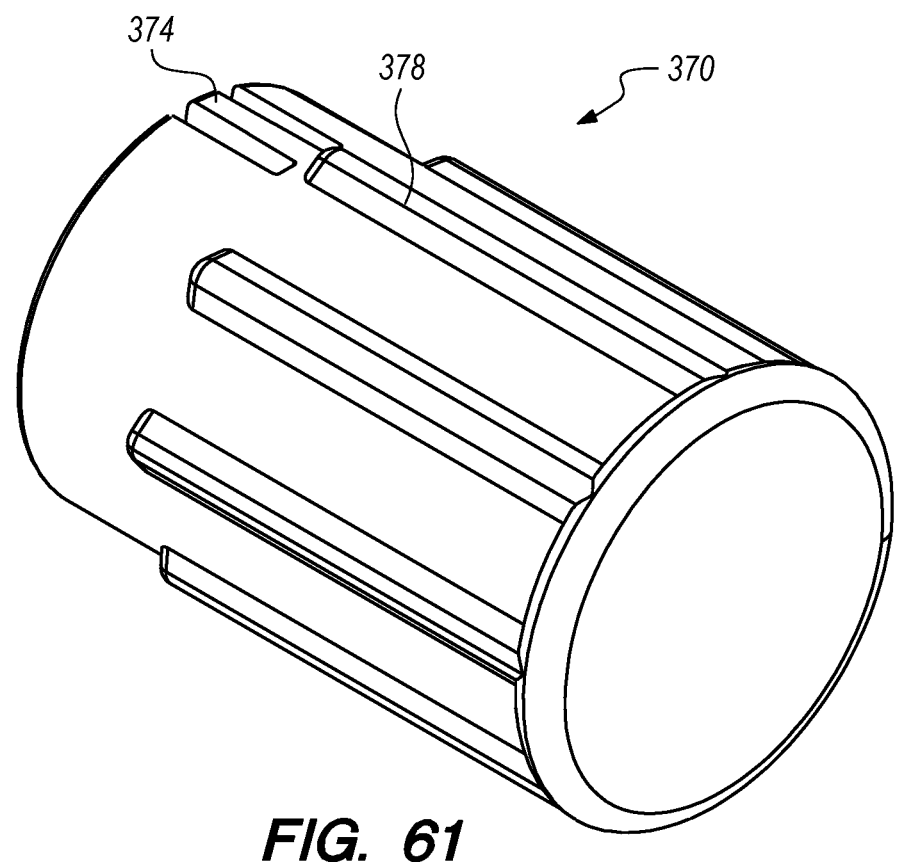

FIGS. 60 and 61 depict the plunger cap 370 according to the embodiment depicted in FIGS. 51, 55-57 and 59, and described above. The plunger cap 370 may be made of a different color material (e.g., polymer) than the plunger member 350 to distinguish the former from the latter.

Figure 62:
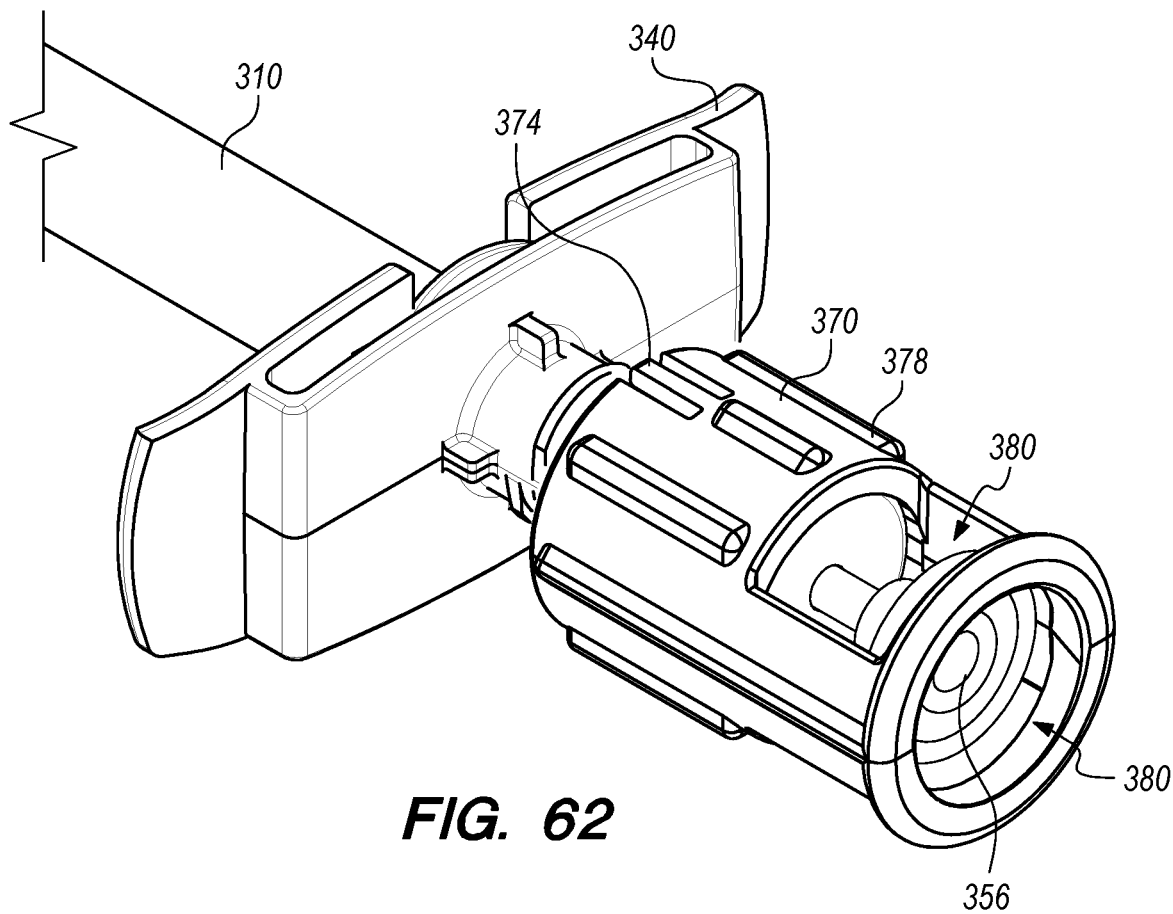
Figure 63:
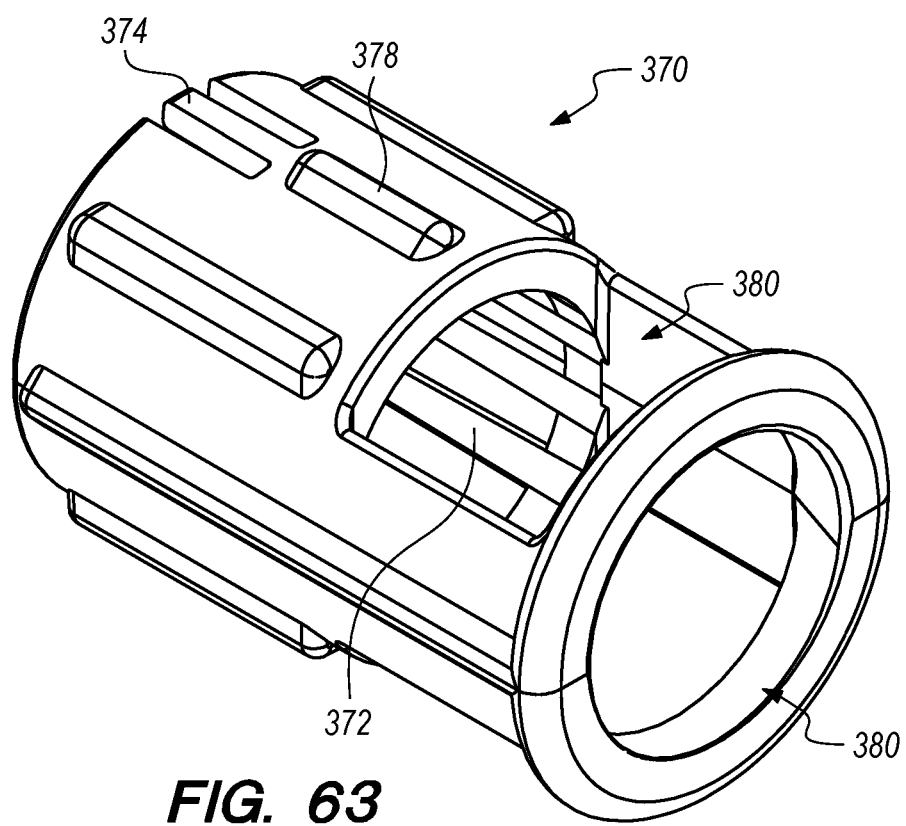

FIGS. 62 and 63 depict a plunger cap 370 according to another embodiment. One difference between this embodiment and the embodiment depicted in FIGS. 60 and 61 is the presence of a plurality of windows 380 that allow the thumb pad/external stop 356 to be seen through the plunger cap 370 even when it is removably coupled to the microdose adapter/rotatable member 360. By allowing the user to see the thumb pad/external stop 356, these windows 380 helped avoid the situation where a user believes that the plunger cap 370 is a thumb pad and applies distally directed force thereto. Although the spline stop 376 in the plunger cap 370 prevents the plunger cap 370 from pressing distally on the actual thumb pad/external stop 356, application of distally directed force to the plunger cap 370 may damage the plunger cap 370. The openings 380 include circumferential and axial openings, and are sized and shaped to prevent manual manipulation of the thumb pad/external stop 356 from outside of the plunger cap 370.

Figure 64:
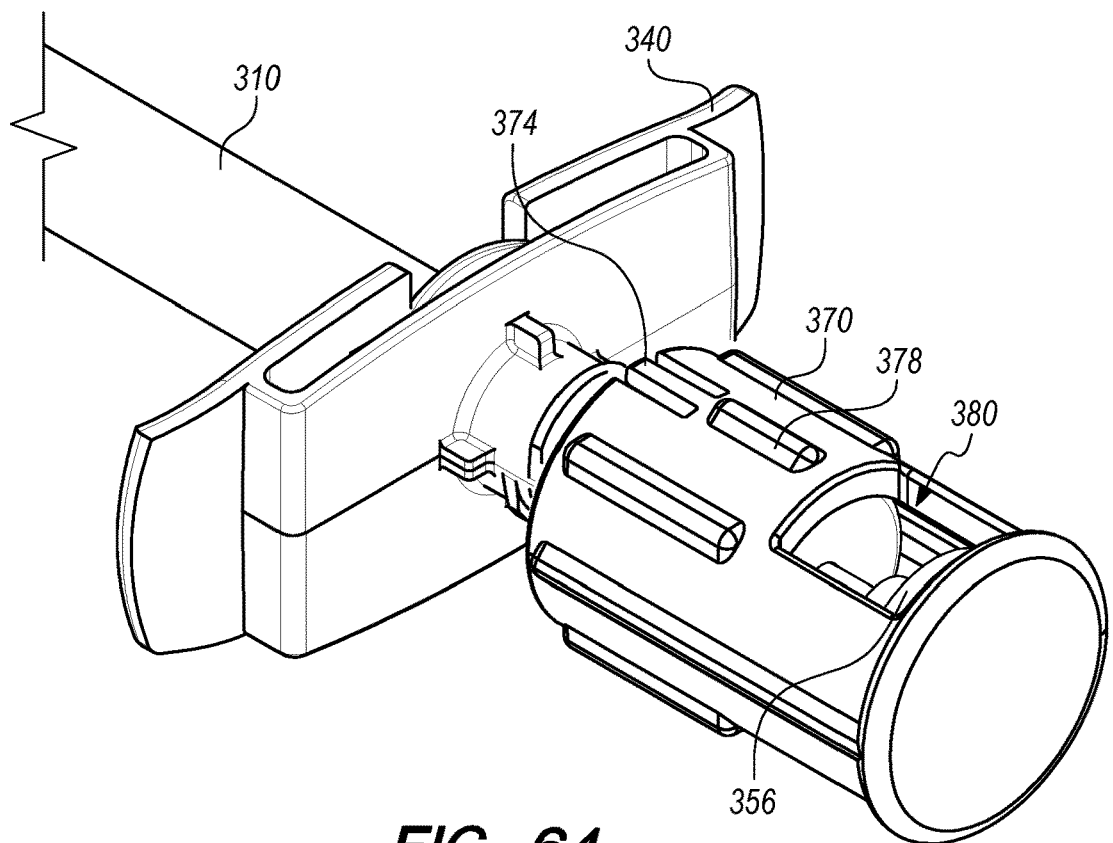
Figure 65:
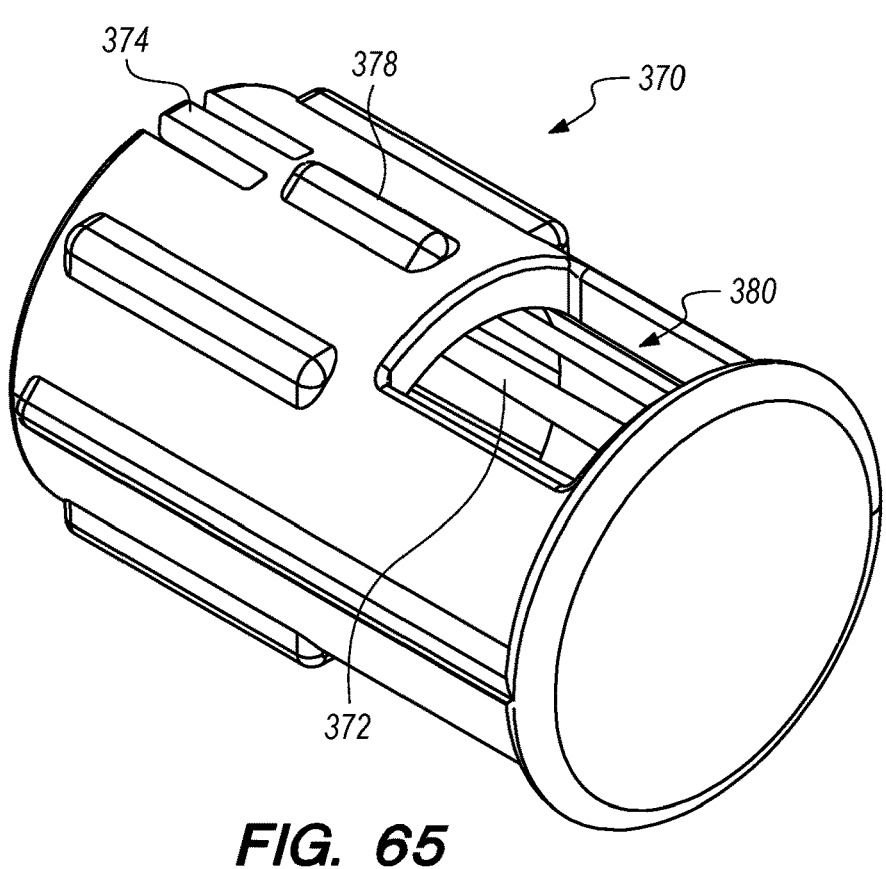

FIGS. 64 and 65 depict a plunger cap 370 according to still another embodiment. One difference between this embodiment and the embodiment depicted in FIGS. 62 and 63 is the presence of circumferential windows 380 that allow the thumb pad/external stop 356 to be seen through the plunger cap 370 even when it is removably coupled to the microdose adapter/rotatable member 360, but not an axial window 380 (see FIGS. 62 and 63). This minimizes the chances that a user with small fingers can manipulate the thumb pad/external stop 356 from outside of the plunger cap 370.

Figure 66:
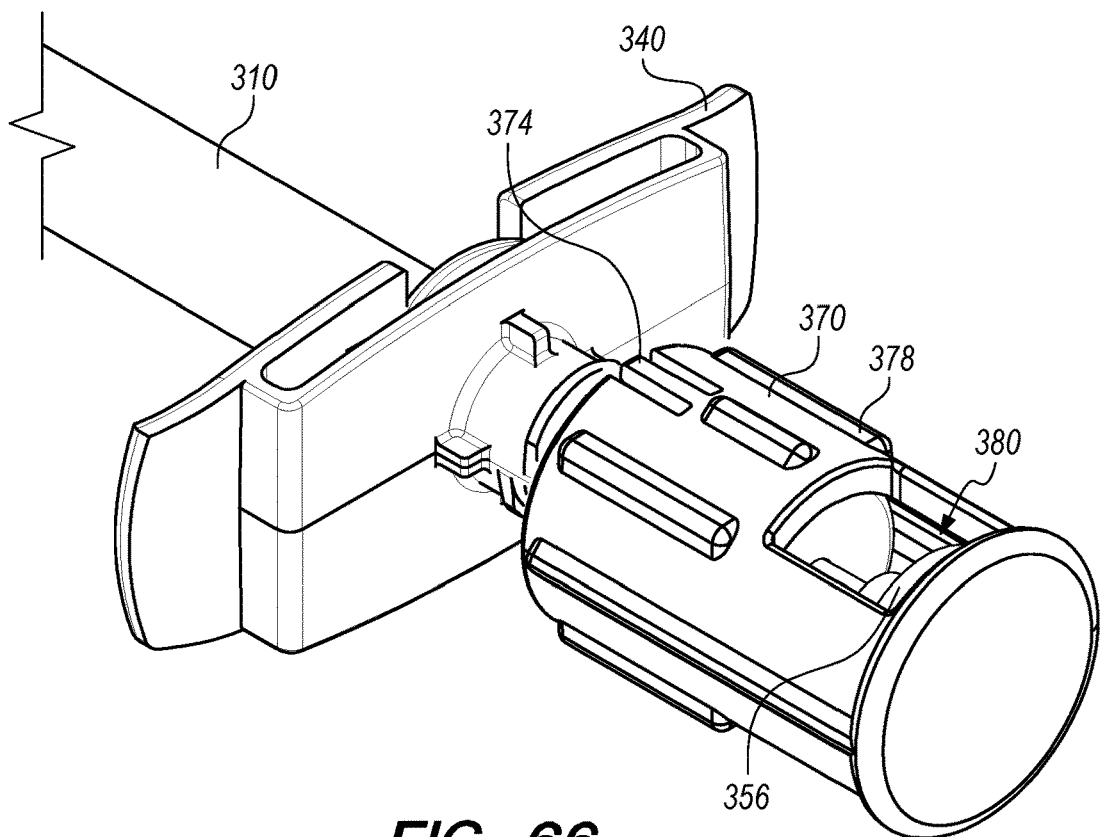
Figure 67:
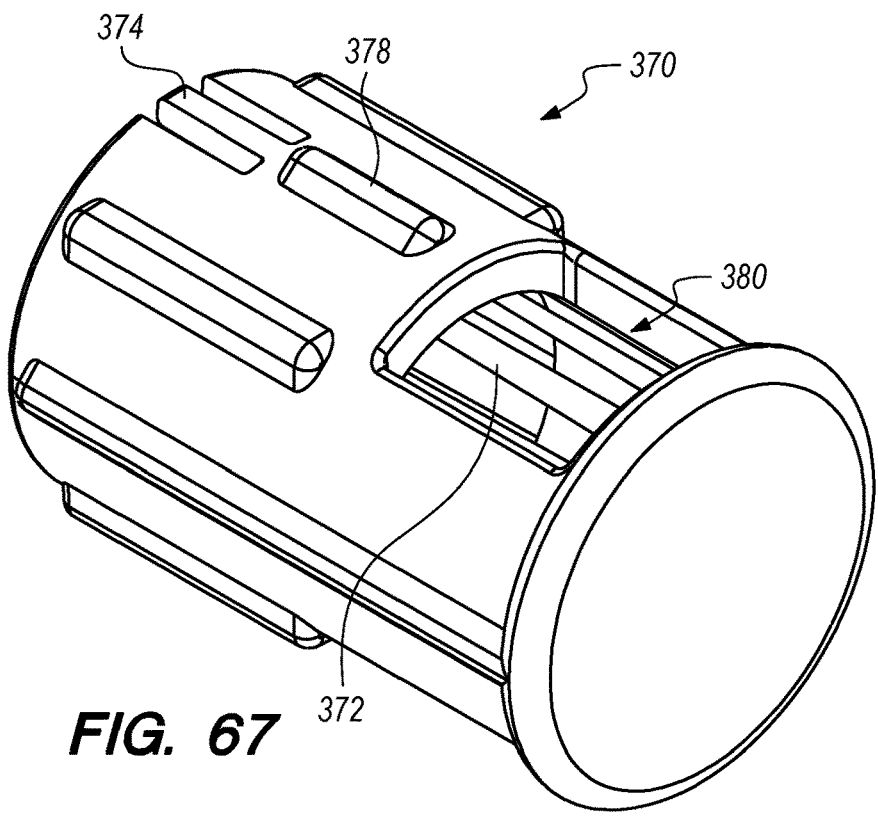

FIGS. 66 and 67 depict a plunger cap 370 according to yet another embodiment. One difference between this embodiment and the embodiment depicted in FIGS. 64 and 65 is that the circumferential windows 380 in this embodiment are smaller than the corresponding circumferential windows 380 in the embodiment depicted in FIGS. 64 and 65. This further minimizes the chances that a user with small fingers can manipulate the thumb pad/external stop 356 from outside of the plunger cap 370.

Figure 68:
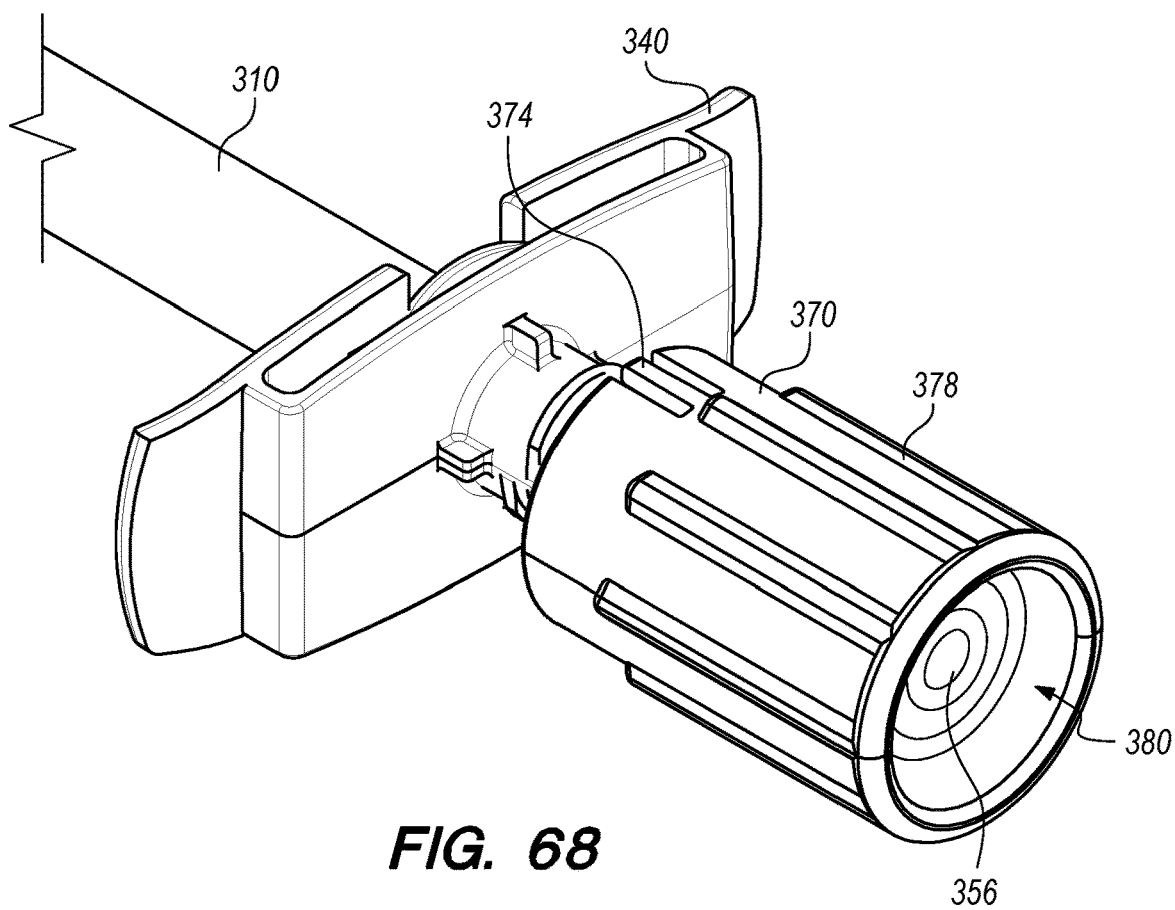
Figure 69:
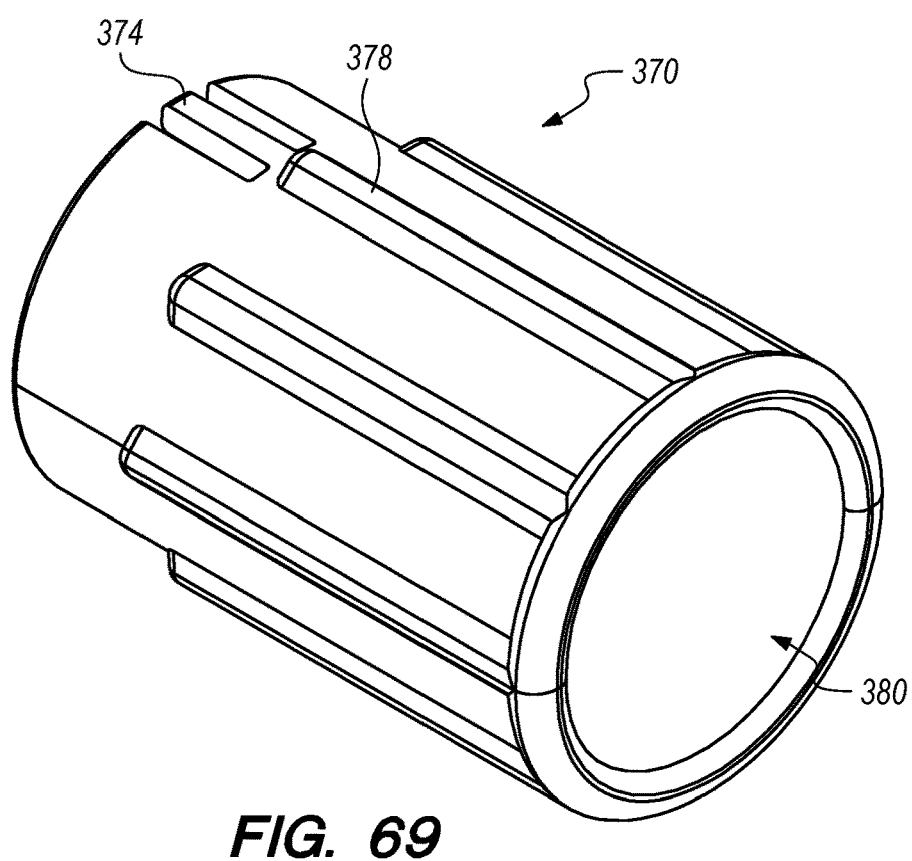

FIGS. 68 and 69 depict a plunger cap 370 according to another embodiment. One difference between this embodiment and the embodiment depicted in FIGS. 62 and 63 is the presence of an axial window 380 that allows the thumb pad/external stop 356 to be seen through the plunger cap 370 even when it is removably coupled to the microdose adapter/rotatable member 360, but not circumferential windows 380 (see FIGS. 62 and 63). This minimizes the chances that a user with small fingers can manipulate the thumb pad/external stop 356 from outside of the plunger cap 370.

Figure 70:
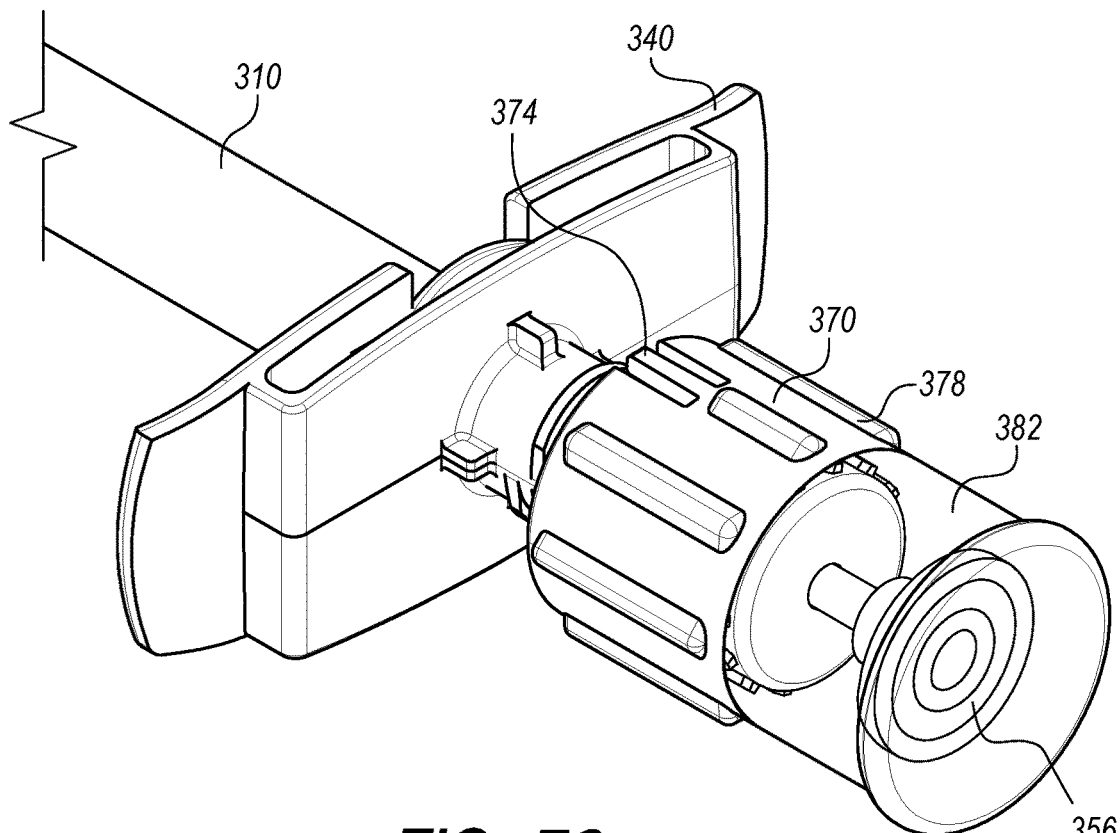
Figure 71:
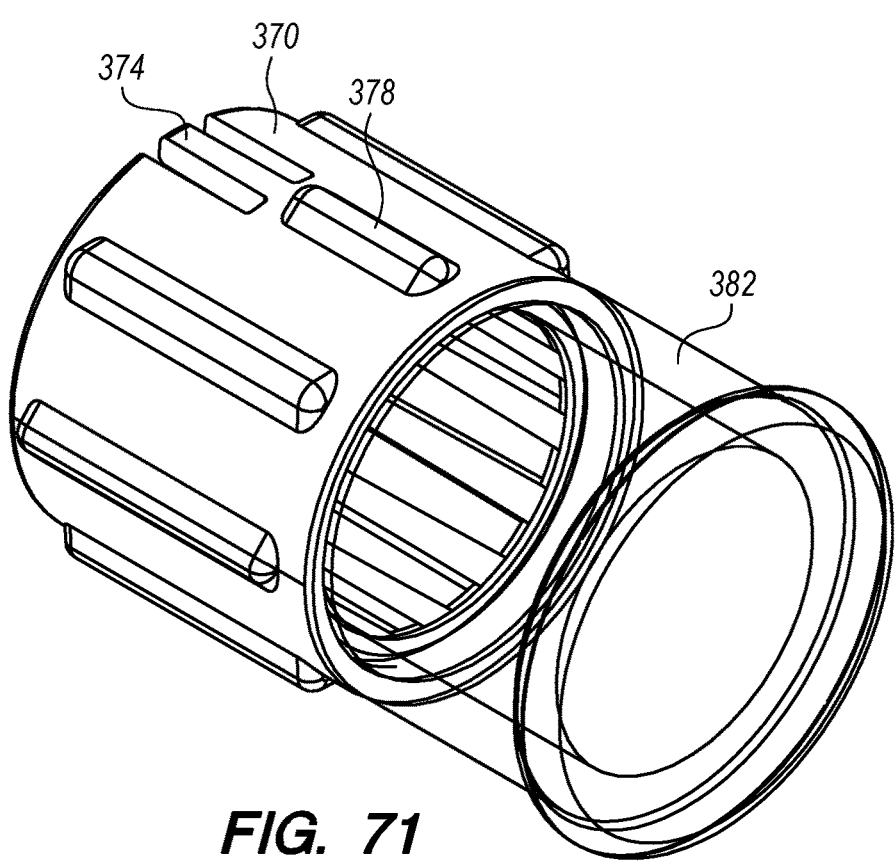

FIGS. 70 and 71 depict a plunger cap 370 according to still another embodiment. One difference between this embodiment and the embodiment depicted in FIGS. 60 and 61 is that the plunger cap 370 in FIGS. 70 and 71 includes a transparent portion 382 that allows the thumb pad/external stop 356 to be seen through the plunger cap 370 even when it is removably coupled to the microdose adapter/rotatable member 360. Unlike the embodiments depicted in FIGS. 52-69, the embodiment depicted in FIGS. 70 and 71 does not include any openings (see windows 380 in FIGS. 52-69). This eliminates the possibility that a user with small fingers can manipulate the thumb pad/external stop 356 from outside of the plunger cap 370.

Figure 72:
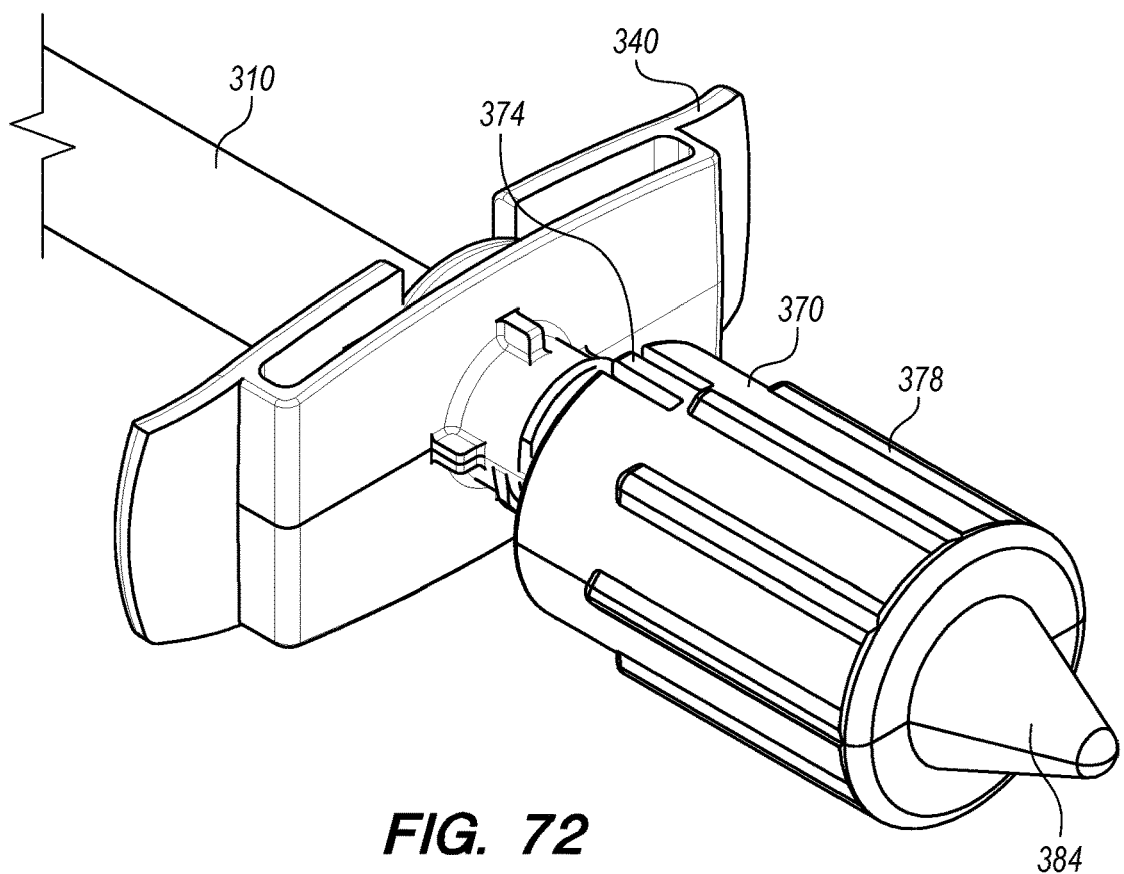
Figure 73:
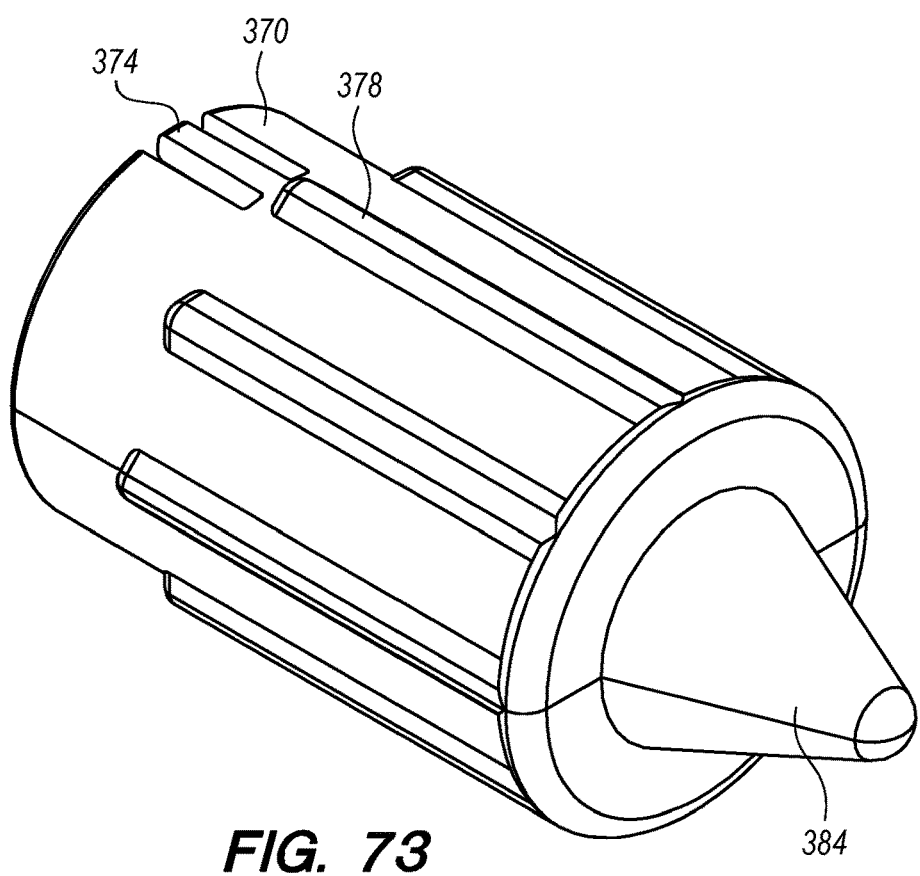

FIGS. 72 and 73 depict a plunger cap 370 according to another embodiment. One difference between this embodiment and the embodiment depicted in FIGS. 60 and 61 is the presence of a pointed feature 384 at the proximal end of the plunger cap 370 depicted in FIGS. 72 and 73. The pointed feature 384 discourages users from applying a distally directed force to plunger cap 370.

End of Microdose Issues and Solutions

In microdose embodiments, the end of the microdose injection occurs when the thumb pad/external stop 356 has been advanced to the proximal flange 362 of the microdose adapter/rotatable member 360, thereby eliminating the gap 358. In many microdose embodiments, some fluid/medicine remains in the interior of the syringe body 310 at the end of the microdose (see e.g., FIG. 49). This residual fluid/medicine may lead users to mistakenly conclude that a full dose has not been properly given. The following embodiments include various solutions to this end of microdose problem.

FIGS. 74-75 depict a microdose injection system 400 according to still another embodiment. The microdose injection system 400 is configured to address the end of microdose problem described above using a positive visual indicator. In the ready to inject state shown in FIG. 74, a gap portion 458 of the plunger member 450 has an eye-catching color (e.g., red) that is different compared to the rest of the microdose injection system 400. During injection, this gap portion 458 is pushed distally into the microdose adapter/rotatable member 460, thereby removing the eye-catching colored gap portion 458 from view of the user. This lack of the eye-catching color indicates that the microdose injection is complete in the injection finish state shown in FIG. 50. In some embodiments this microdose injection system 400 is marketed with materials that reinforce this message (e.g., "no red=dose delivered").

Figure 78:
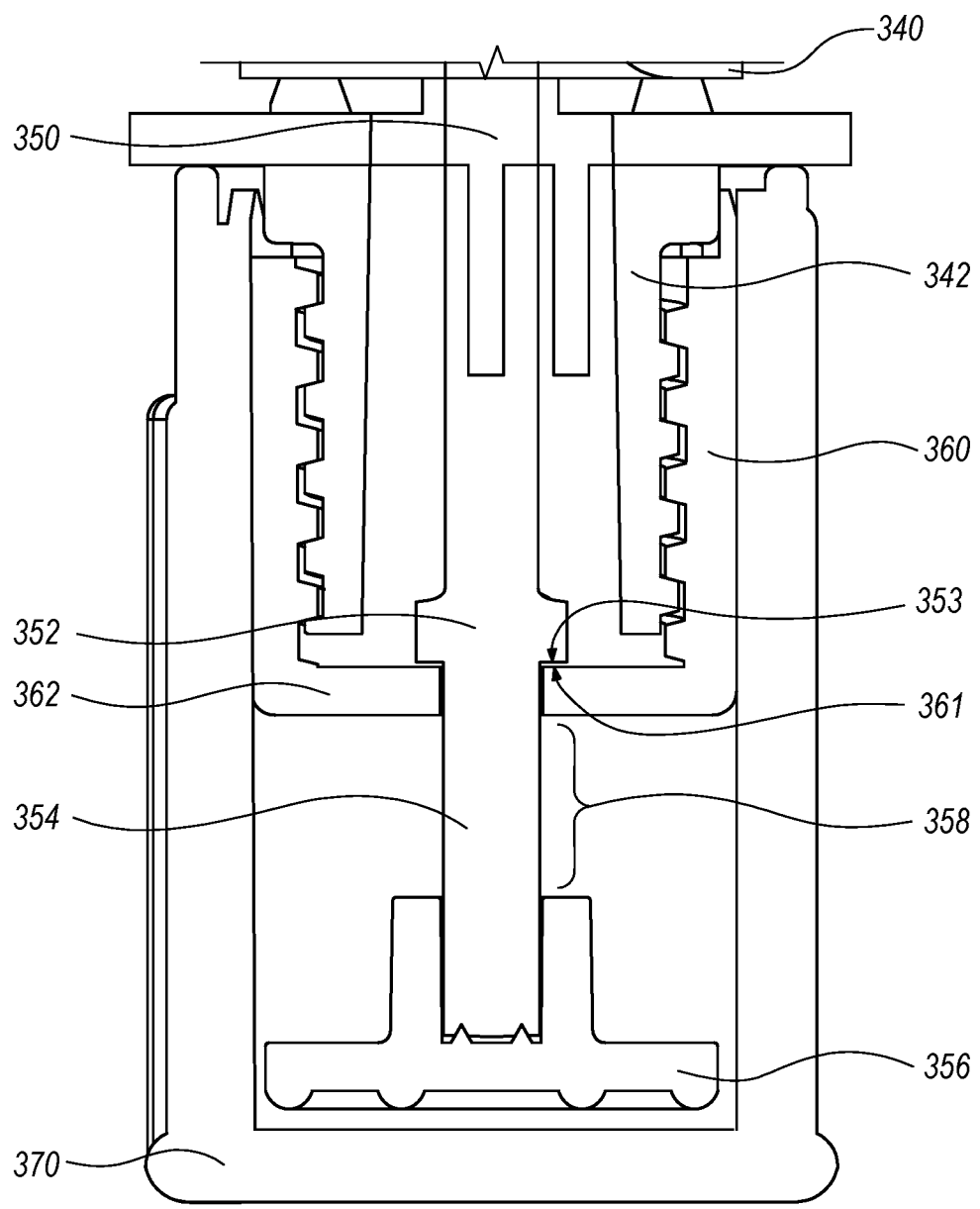

FIGS. 76-84 depict an alternative microdose injection method using the microdose injection system 300 depicted in FIGS. 36-50 to address the end of microdose problem according to another embodiment. The needle assembly and vertical positioning of the microdose injection system 300 depicted in FIGS. 36-41 are identical to the injection method depicted in FIGS. 76-84. The de-bubbling procedure is different as depicted in FIGS. 76-78 (compared to FIGS. 42-44). During this alternative de-bubbling procedure, the plunger cap 370 is rotated clockwise until the distal ends of the plunger cap 370 and the microdose adapter/rotatable member 360 abut respective proximally directed surfaces of the finger flange 340, as shown in FIG. 78. Moving the plunger cap 370 and the microdose adapter/rotatable member 360 more distal relative to the syringe body 310 moves the plunger member 350 and the stopper member 320 coupled thereto more distal relative to the syringe body 310. This is apparent by comparing FIGS. 43 and 77, which depict corresponding steps in the two related microdose injection methods.

Because the microdose injection system 300 is in a vertical position during de-bubbling, moving the stopper member 320 coupled thereto more distal relative to the syringe body 310 only ejects some of the fluid/medicine in the interior of the syringe body 310 out into the ambient environment. This alternative de-bubbling procedure can be performed with a needle cap on the needle to minimize contamination and inadvertent needle-stick risks, This alternative de-bubbling procedure can be performed with less visual confirmation and therefore in less time. Since the volume of fluid/medicine delivered during the microdose injection process is proportional to the gap 358, increasing the distance the stopper member 320 is moved during de-bubbling does not affect either the gap or the volume of fluid/medicine delivered.

Figure 79:
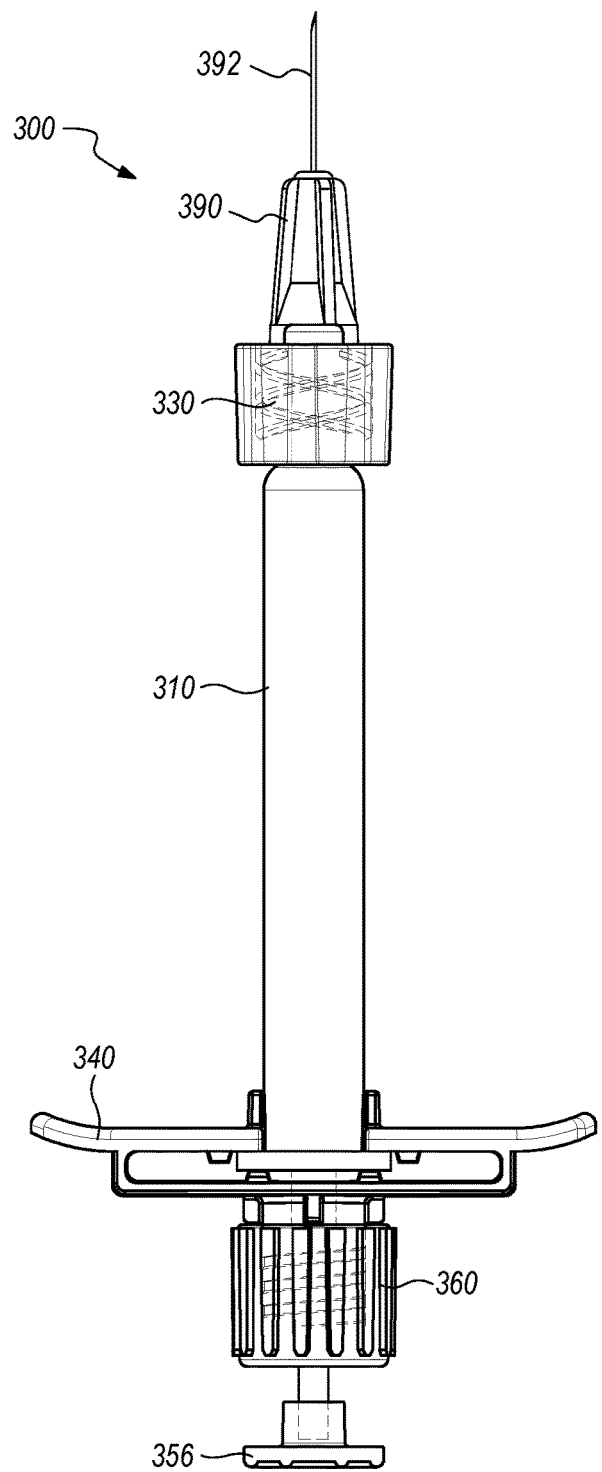
Figure 80:
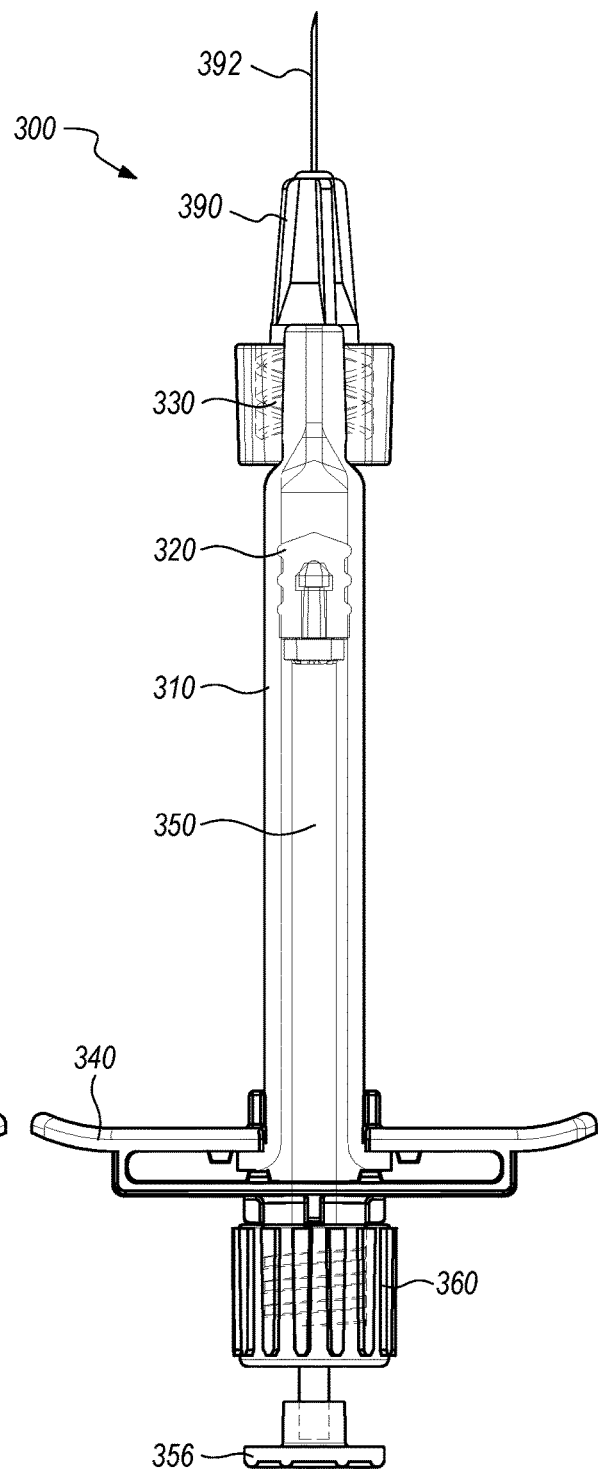
Figure 81:
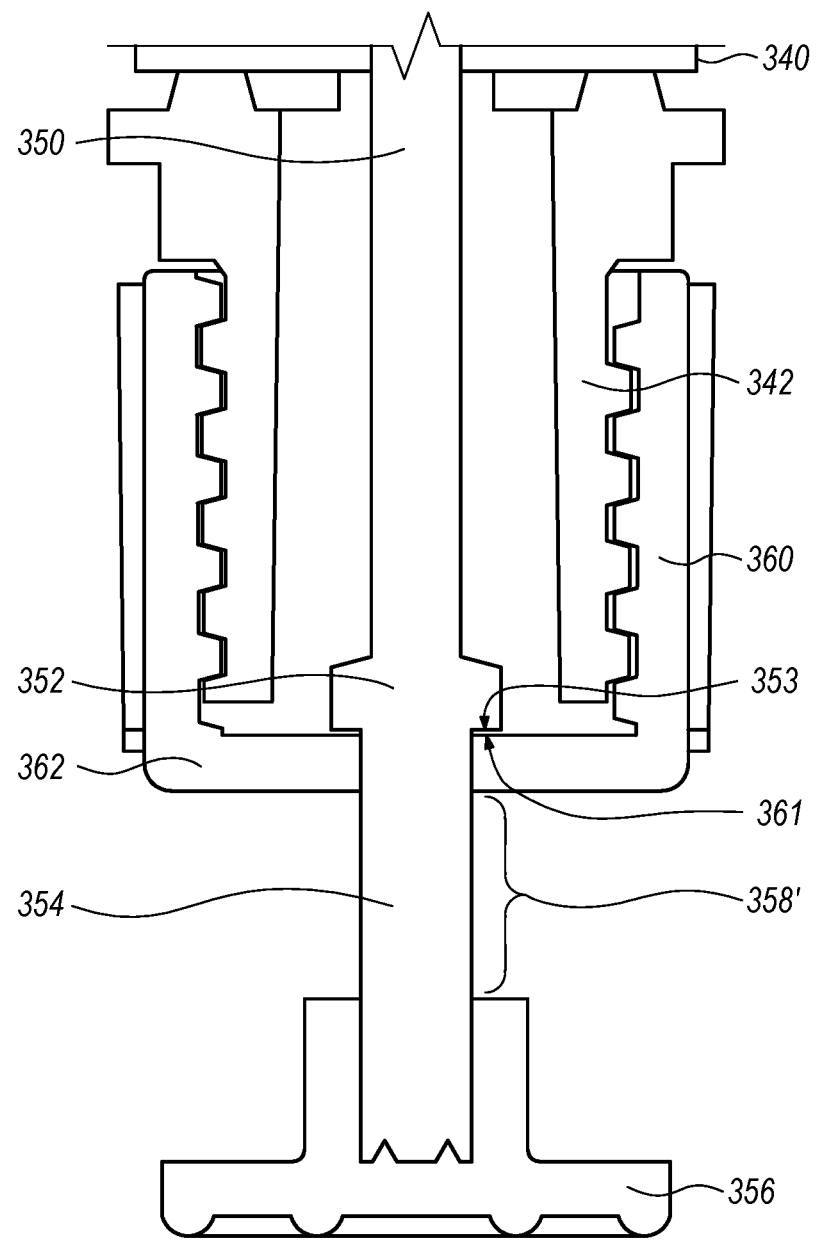
Figure 82:
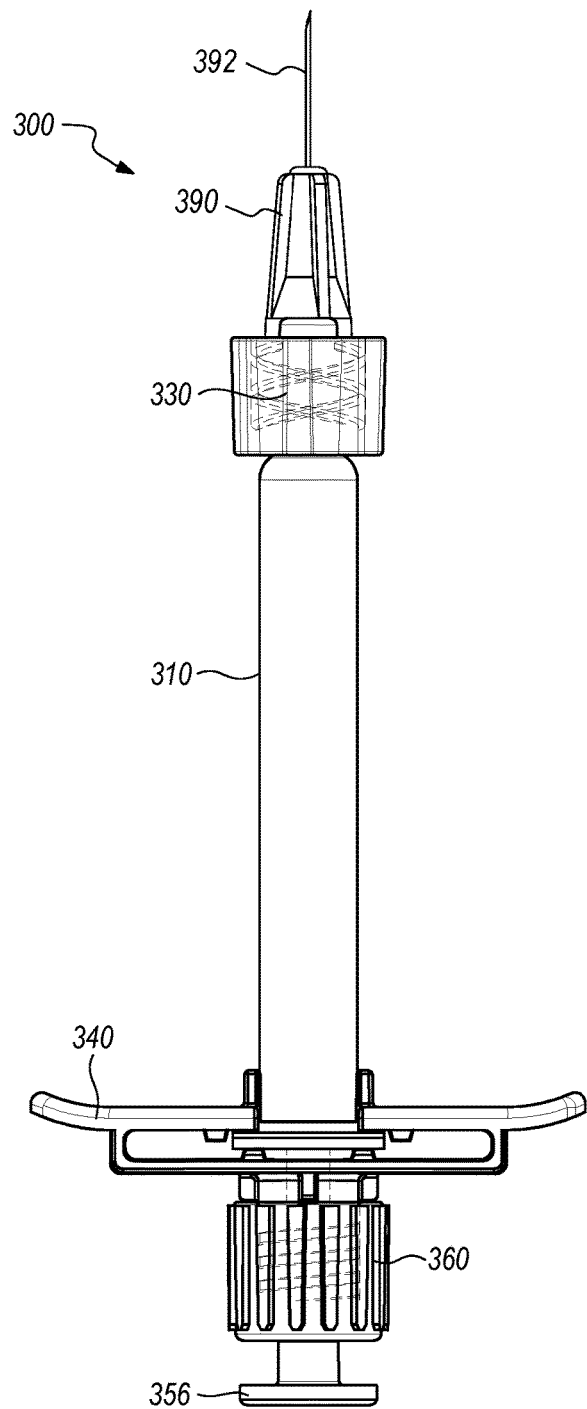
Figure 83:
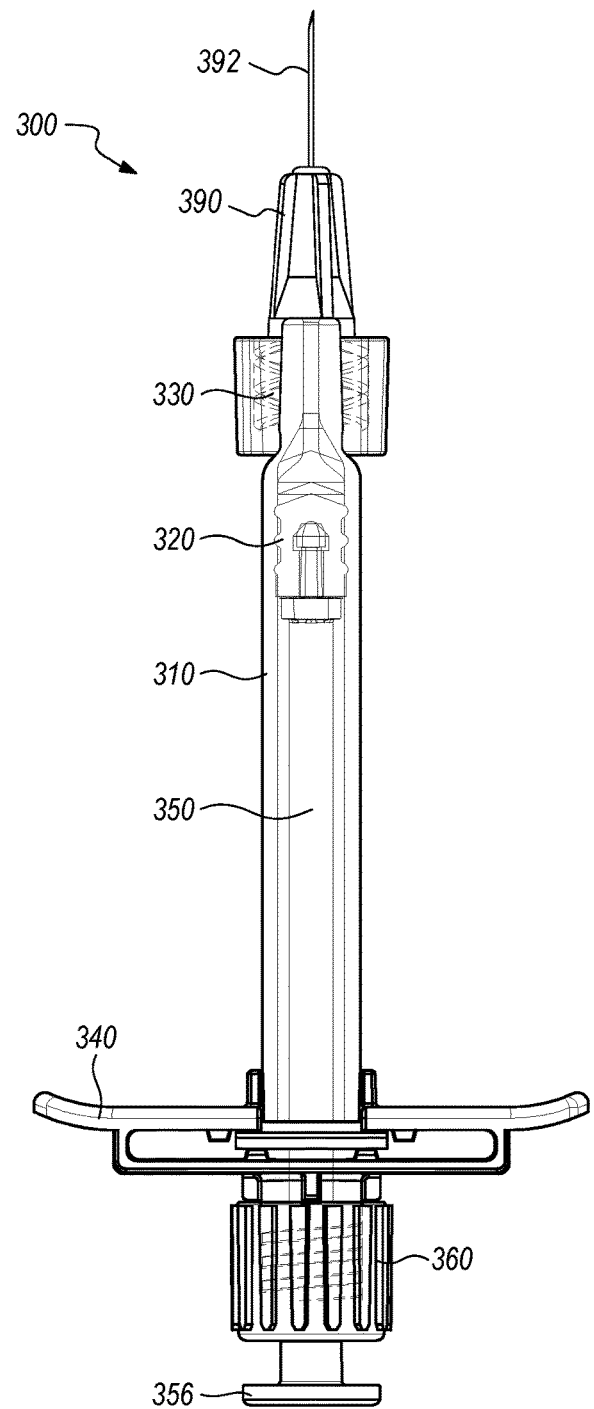
Figure 84:
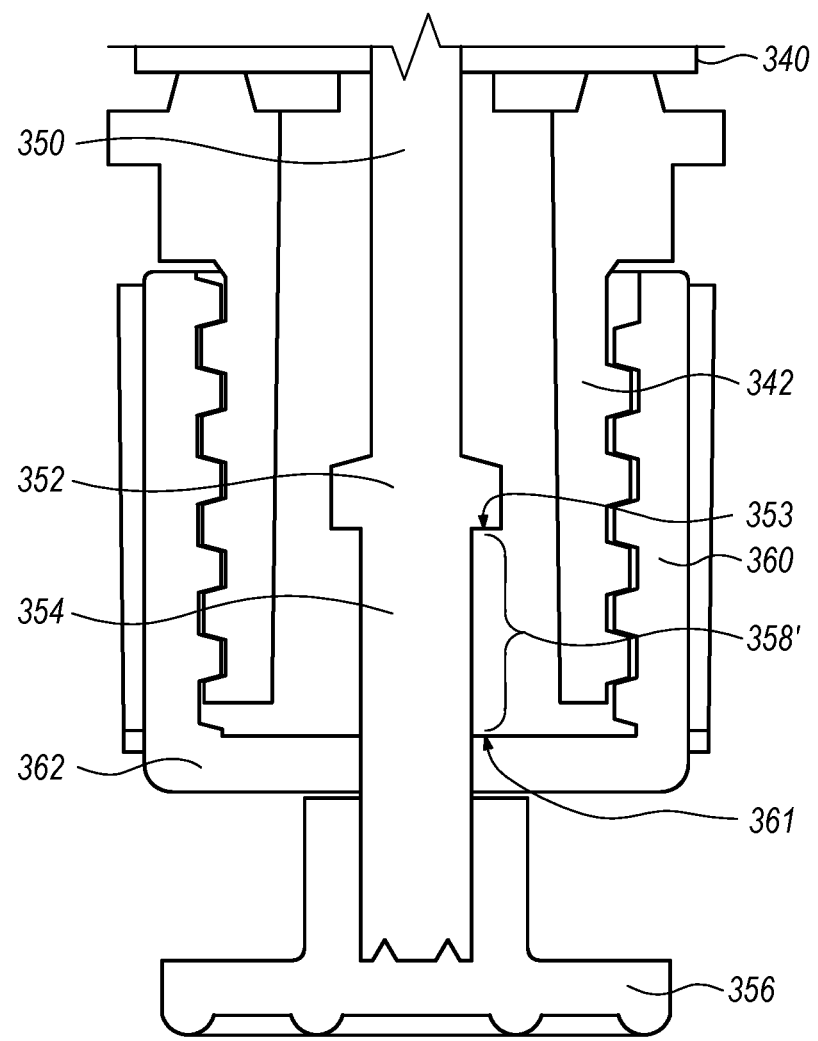

FIGS. 79-81 depict the microdose injection system 300 after the microdose injection system 300 has been de-bubbled, like FIGS. 45-47. FIGS. 82-84 depict the microdose injection system 300 after the injection has been given, like FIGS. 48-50. As shown in FIG. 83, after the injection, the stopper member 320 is very close (e.g., about 1 mm) from the distal end of the interior of the syringe body 310. Users will be less alarmed by this small amount of room left between the stopper member 320 and the distal end of the interior of the syringe body 310. Some may even see this as an indication of the end of the microdose injection. The difference between this alternative microdose injection method and the one depicted in FIGS. 36-50 and described above can be visualized by comparing FIGS. 49 and 83.

In another embodiment, the gap 358 between the proximally facing surface of the proximal flange 362 and the distally facing surface of the thumb pad/external stop 356 can be increased such that the stopper member 320 can be moved distally in an interior of the syringe body 310 until it hits bottom. This embodiment can be combined with the alternative de-bubbling mechanism depicted in FIGS. 76-84. In such a combined embodiment, the user will move all of the microdose injection system 300 components as far distally as possible, and thereby achieve instead of a complete dose injection. Embodiments where the gap 358 is increased so that the stopper member 320 can be inserted to the bottom of the interior of the syringe body 310 uncouple the injection/dose volume from the axial length of the gap 350. This embodiment sacrifices some microdose injection system accuracy for reducing user concerned about dose completion/end of dose.

Figure 85A:
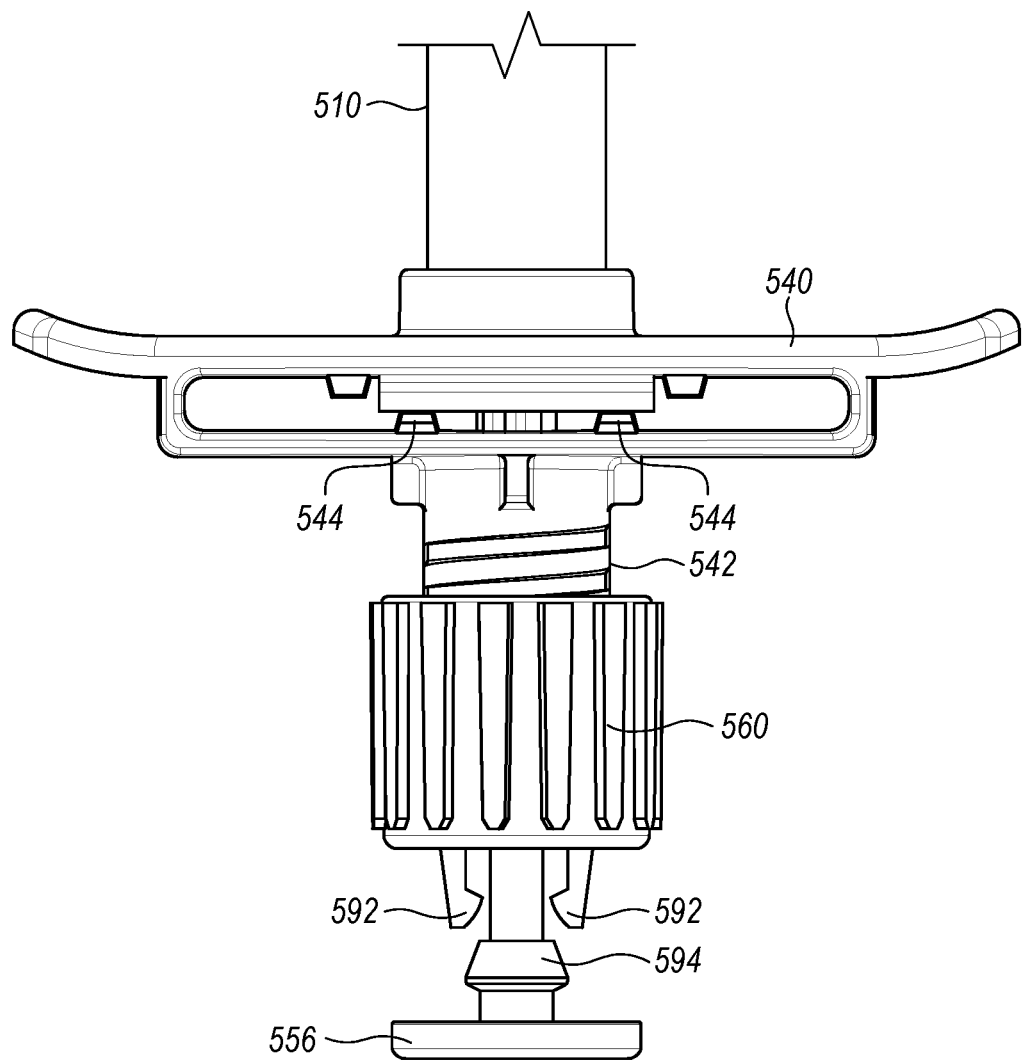
FIGS. 85A-85B illustrate various aspects of a microdose injection system according to one embodiment.
Figure 85B:
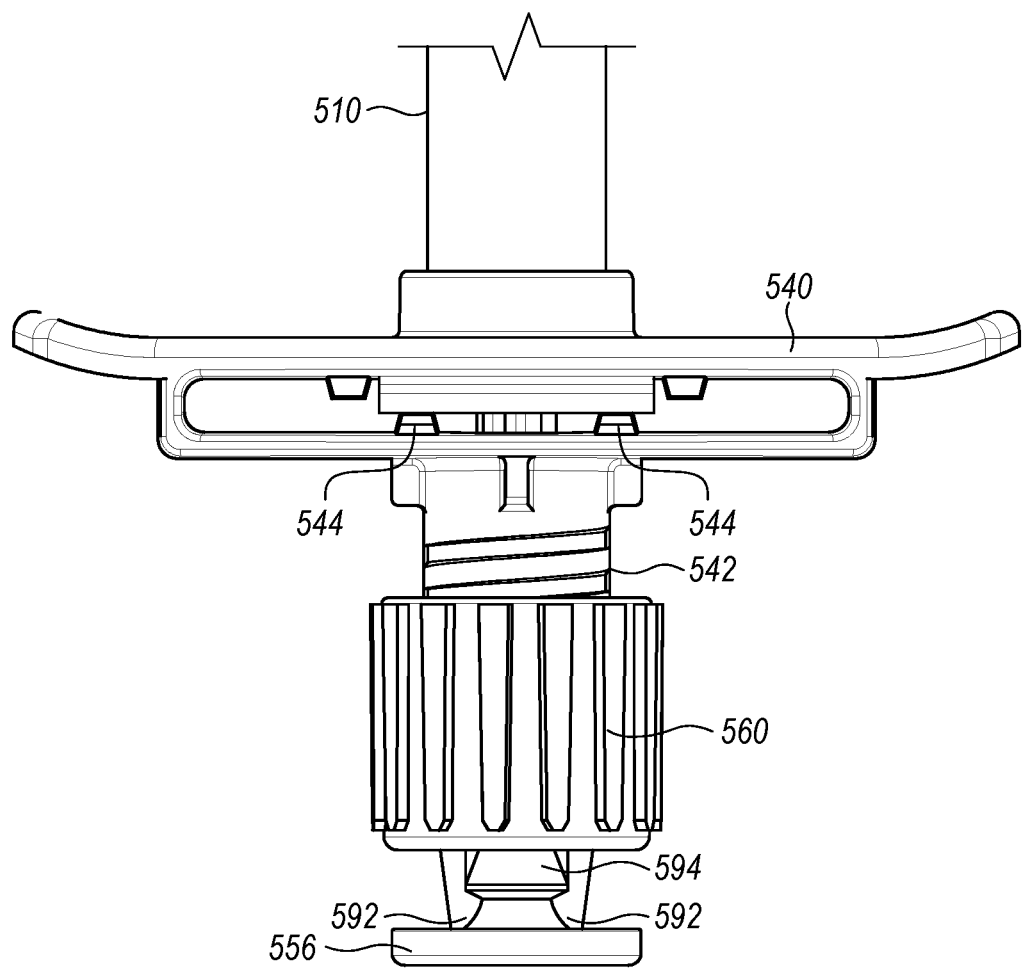

FIGS. 85A and 85B depict a microdose injection system 500 according to yet another embodiment. The microdose injection system 500 is configured to address the end of microdose problem described above using an audible/tactile indicator. In the microdose injection system 500 depicted in FIGS. 85A and 85B, the microdose adapter/rotatable member 560 includes a plurality (e.g., and two) of deflectable spring arms 592. After the complete microdose is given by full insertion of the plunger member 550, the deflectable spring arms 592 snap over a notch 594 formed on the plunger member 550. This mechanically generates a mechanical click that can be felt and/or heard by a user to provide end of dose tactile and/or audible feedback.

While various embodiments have been described with specific connectors (e.g., slip and Luer), these embodiment can be used with any known injection system connectors.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, PTFE, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed is:

1. A system for injecting, comprising:
   a syringe body having proximal and distal ends, a syringe interior, and a syringe flange at the proximal end thereof;
   a finger flange removably coupled to the syringe flange, the finger flange including proximally directed external threads;
   a stopper member disposed in the syringe interior; and
   a plunger member coupled to the stopper member;
   the plunger member comprising
      a rotatable member disposed on the proximally directed external threads and configured to insert the stopper member distally in the syringe interior relative to the syringe body with rotation of the rotatable member, and
      a portion located proximal of the rotatable member and configured to be moved distally to further insert the stopper member distally in the syringe interior relative to the syringe body.

2. The system of claim 1, wherein moving the portion distally to further insert the stopper member distally in the syringe interior relative to the syringe body ejects about 50 microliters of fluid from the syringe interior.

3. The system of claim 1, further comprising a safety member removably coupled to the portion of the plunger member to prevent distal movement thereof.

4. The system of claim 1, further comprising a finger flange coupled to the syringe flange.

5. A system for injecting, comprising:
   a syringe body having proximal and distal ends, a syringe interior, and a syringe flange at the proximal end thereof;
   a stopper member disposed in the syringe interior;
   a plunger member coupled to the stopper member;
   a finger flange removably coupled to the syringe flange, the finger flange including proximally directed external threads; and
   a rotatable member disposed on the proximally directed external threads, the rotatable member having an opening through which the plunger member is disposed,
   wherein the rotatable member is configured to insert the plunger member and the stopper member coupled thereto distally in the syringe interior relative to the syringe body with rotation of the rotatable member relative to the proximally directed external threads.

6. The system of claim 5, wherein the plunger member comprises an external stop proximal of the rotatable member configured to be moved distally relative to the rotatable member to further insert the plunger member and the stopper member coupled distally in the syringe interior relative to the syringe body.

7. The system of claim 5, wherein moving the external stop distally to further insert the stopper member distally in the syringe interior relative to the syringe body ejects about 50 microliters of fluid from the syringe interior.

8. The system of claim 5, further comprising a plunger cap removably coupled to the rotatable member and configured to prevent distal movement of the external stop relative to the rotatable member.

9. The system of claim 8, wherein the plunger cap defines an opening through which a proximal end of the plunger member is visible from outside of the plunger cap.

10. The system of claim 9, wherein the opening is sized and shaped to prevent manual manipulation of the proximal end of the plunger member from outside of the plunger cap.

11. The system of claim 8, wherein the plunger cap comprises a transparent material through which a proximal end of the plunger member is visible from outside of the plunger cap.

12. The system of claim 8, wherein the plunger cap comprises a proximal end pointed feature.

13. The system of claim 8, wherein the plunger cap comprises a retention feature to removably couple the plunger cap to the rotatable member.

14. The system of claim 8, wherein the plunger cap comprises a first plurality of splines configured to cooperate with a corresponding second plurality of spline on the rotatable member to rotate the rotatable member.

15. The system of claim 8, wherein the plunger cap comprises a knurled outer surface to facilitate manual rotation of the plunger cap and the rotatable member.

16. The system of claim 5, the finger flange comprising an internal surface projection configured to secure the finger flange on the syringe flange.

17. The system of claim 5, wherein the finger flange is elastically deformable to secure the finger flange on the syringe flange.

18. The system of claim 5,
   wherein the rotatable member is configured to insert the plunger member and the stopper member coupled thereto distally in the syringe interior relative to the syringe body with rotation of the rotatable member relative to the proximally directed external threads in a first direction, and
   wherein the rotatable member comprises a ratcheting mechanism to prevent rotation of the rotatable member relative to the proximally directed external threads in a second direction opposite to the first direction.

19. The system of claim 5, the plunger member comprising an internal stop disposed distal of the opening in the rotatable member and sized to prevent passage of the internal stop through the opening, such that the internal stop limits proximal movement of the plunger member.

20. The system of claim 5, the plunger member comprising a visual injection indicator.

* * * * *